(12) United States Patent
Krueger et al.

(10) Patent No.: US 12,217,223 B2
(45) Date of Patent: Feb. 4, 2025

(54) INSERTING A FURTHER DATA BLOCK INTO A FIRST LEDGER

(71) Applicant: Siemens Healthcare GmbH, Erlangen (DE)

(72) Inventors: Benedikt Krueger, Ebensfeld (DE); Thomas Friese, Munich (DE); Thomas Gossler, Erlangen (DE); Tilo Christ, Erlangen (DE); Michael Kelm, Erlangen (DE); Moritz Uebler, Obermichelbach (DE); Friedrich Hegendoerfer, Weilersbach (DE); Frank Steinmetz, Eggolsheim (DE); Markus Kirchner, Erlangen (DE); Tobias Hartmann, Zirndorf (DE); Michael Rommel, Erlangen (DE); Swen Campagna, Engelthal (DE); Xiang Sean Zhou, Exton, PA (US); Eric Albrecht, Nuremberg (DE); Robert Soellner, Bubenreuth (DE)

(73) Assignee: SIEMENS HEALTHINEERS AG, Forchheim (DE)

( * ) Notice: Subject to any disclaimer, the term of this patent is extended or adjusted under 35 U.S.C. 154(b) by 1122 days.

(21) Appl. No.: 16/970,693

(22) PCT Filed: Feb. 25, 2019

(86) PCT No.: PCT/EP2019/054623
§ 371 (c)(1),
(2) Date: Aug. 18, 2020

(87) PCT Pub. No.: WO2019/166376
PCT Pub. Date: Sep. 6, 2019

(65) Prior Publication Data
US 2020/0380475 A1  Dec. 3, 2020

(30) Foreign Application Priority Data

Feb. 28, 2018 (EP) .................................. 18159171

(51) Int. Cl.
*G16H 10/60* (2018.01)
*G06F 16/23* (2019.01)
(Continued)

(52) U.S. Cl.
CPC ....... *G06Q 20/065* (2013.01); *G06F 16/2379* (2019.01); *G06F 16/27* (2019.01);
(Continued)

(58) Field of Classification Search
None
See application file for complete search history.

(56) References Cited

U.S. PATENT DOCUMENTS

| | | | |
|---|---|---|---|
| 10,616,324 B1 * | 4/2020 | Kaddoura | H04L 69/329 |
| 2010/0094581 A1 * | 4/2010 | Cagle | B05B 11/108 |
| | | | 702/176 |

(Continued)

FOREIGN PATENT DOCUMENTS

| | | | | |
|---|---|---|---|---|
| CN | 107743632 A | 2/2018 | | |
| TW | 201732666 A | 9/2017 | | |
| WO | WO-2018036701 A1 * | 3/2018 | ......... | G06F 16/1824 |

OTHER PUBLICATIONS

Konstantinos, Christidis et al. "Blockchains and Smart Contracts for the Internet of Things" IEEE Access, vol. 4, pp. 2292-2303, 2016 // Doi: 10.1109/ACCESS.2016.2566339;.
(Continued)

*Primary Examiner* — Gregory Lultschik
(74) *Attorney, Agent, or Firm* — Harness, Dickey & Pierce, P.L.C.

(57) ABSTRACT

A method is for inserting a further data block into a first ledger, the first ledger including data blocks. In an embodi-
(Continued)

ment, the method includes receiving a further medical dataset via an interface; determining the further data block via a calculation unit. The further data block includes the further medical dataset and a further link information. The further link information includes a hash of at least one of the data blocks of the first ledger. Finally, in an embodiment the method includes inserting the further data block into the first ledger via the calculation unit.

20 Claims, 27 Drawing Sheets

(51) Int. Cl.
    *G06F 16/27*     (2019.01)
    *G06F 21/62*     (2013.01)
    *G06Q 20/06*     (2012.01)
    *H04L 9/06*     (2006.01)
    *H04L 9/32*     (2006.01)
    *H04L 9/00*     (2022.01)

(52) U.S. Cl.
    CPC ......... *G06F 21/6245* (2013.01); *G16H 10/60* (2018.01); *H04L 9/0637* (2013.01); *H04L 9/0643* (2013.01); *H04L 9/3247* (2013.01); *H04L 9/50* (2022.05); *H04L 2209/56* (2013.01)

(56) References Cited

U.S. PATENT DOCUMENTS

| | | | |
|---|---|---|---|
| 2015/0165118 A1* | 6/2015 | Lee | A61M 5/14228 |
| | | | 604/67 |
| 2016/0342978 A1 | 11/2016 | Davis et al. | |
| 2017/0163733 A1 | 6/2017 | Grefen et al. | |
| 2017/0177898 A1 | 6/2017 | Dillenberger | |
| 2018/0260212 A1* | 9/2018 | Wisnovsky | G06F 16/134 |
| 2019/0132131 A1* | 5/2019 | Clements | H04L 9/3239 |
| 2021/0176251 A1* | 6/2021 | Ozhigin | H04L 9/0618 |

OTHER PUBLICATIONS

Popov, Serguei "The Tangle" Version 1.4.2.; Feb. 9, 2018 (Feb. 9, 2018) // https://assets.ctfassets.nct/r1dr6vzfxhov/2t4uxvslqk0EUau6g2sw0g/45cac33637ca92185dd9f4a3a218c1cc/iota1_4_3.pdf.

International Search Report PCT/ISA/210 for International Application No. PCT/EP2019/054623 dated Jun. 7, 2019.

European Search Report for European Application No. 1815911.0 dated Aug. 28, 2018.

Written Opinion of the International Searching Authority PCT/ISA/237 for International Application No. PCT/EP2019/054623 dated Jun. 7, 2019.

* cited by examiner

INSERTING A FURTHER DATA BLOCK INTO A FIRST LEDGER

PRIORITY STATEMENT

This application is the national phase under 35 U.S.C. § 371 of PCT International Application No. PCT/EP2019/054623 which has an International filing date of Feb. 25, 2019, which designated the United States of America and which claims priority to European Application No. EP 18159171.0 filed Feb. 28, 2018, the entire contents of each of which are hereby incorporated by reference herein, in their entirety and for all purposes.

FIELD

Embodiments of the present invention generally relates to a device and method of inserting a further data block into a ledger.

BACKGROUND

A prerequisite for using data-driven applications, in particular for data-driven healthcare applications, is that a database can be stored at different entities in a synchronous and revision safety way. Examples for such data bases are an electronic patient record, log files for maintenance operations at medical apparatuses, or log files for the usage of medical apparatuses.

For storing databases in a synchronous way at different entities, it is known to operate a central agency or a central entity, which is trusted by the other non-central entities and which coordinates and initializes changes to the local databases of the entities, or which alternatively stores a centralized database which can be accessed by the non-central entities. If using such central entities, a failure of the central entity or a failure of the communication with the central entity leads to a breakdown of the synchronization, or even to a breakdown of the data accessibility. Furthermore, if the central entity is compromised, also all non-central entities have to be considered as compromised.

For storing databases in a revision safety way it is known to access these databases only with certified software programs, where these certified software programs do not allow a retroactive modification of the database. Also in this case a central certification entity is necessary, which might be compromised, furthermore during certification unintentional or intentional errors in the program code can be overlooked.

SUMMARY

At least one embodiment of the present invention is directed to creating synchronized and revising safe distributed medical databases.

Embodiments of the present application are directed to a method, a block creation unit, and a computer program product. Further possible solutions are described in the specification.

At least one embodiment of the invention is described with respect to systems, in particular with respect to the block creation unit embodiment, as well as with respect to the corresponding methods, in particular with respect to the method for inserting a further data block into a first ledger. Features, advantages or alternative embodiments herein can be assigned to the other objects, in particular to the other claimed objects, and vice versa. In other words, claims and embodiments for the systems can be improved with features described or claimed in the context of embodiments of the methods. In this case, the functional features of the methods are embodied by objective units of the systems.

At least one embodiment of the invention relates to a method for inserting a further data block into a first ledger, comprising the step of receiving a further medical dataset with an interface, furthermore comprising the step of determining the further data block with a calculation unit, wherein the further data block comprises the medical dataset and a link information, wherein the further link information comprises a hash of at least one of the data blocks of the first ledger, furthermore comprising the step of including the further data block into the first ledger with the calculation unit.

At least one embodiment of the invention is furthermore related to a method for verifying a further data block to be inserted into a second ledger, wherein the second ledger comprises data blocks, comprising the step of receiving the second ledger with an interface, the step of receiving the further data block with the interface, wherein the further data block comprises a further medical dataset and a further link information, wherein the further link information comprises a hash of at least one of the data blocks of the second ledger, the step of verifying the further link information based on the second ledger with the calculation unit, and, in the case of a positive verification, the step of inserting the further data block into the second ledger with the calculation unit. The inventors recognized that this method the second ledger can be synchronized with a first ledger, wherein the first ledger is stored in a block creation unit that determined the further data block, even if the block creation unit and the block verification unit are spatially separated.

In another embodiment the invention relates to a block creation unit for inserting a further data block into a first ledger, wherein the first ledger comprises data blocks, comprising the following units:
  interface, configured for receiving a further medical dataset,
  calculation unit, configured for determining the further data block, where in the further data block comprises the further medical dataset and a further link information, wherein the further link information comprises a hash of at least one of the data blocks of the first ledger, and furthermore configured for inserting the further data block into the first ledger.

In another embodiment, the invention relates to a medical apparatus comprising a block creation unit.

In another embodiment, the invention relates to a computer program product comprising a computer program, the computer program being loadable into a memory unit of a block creation unit, including program code sections to make the block creation unit execute the method for inserting a further data block in to a first ledger according to an embodiment of the invention when the computer program is executed in the block creation unit.

In another embodiment, the invention relates to a computer-readable medium, on which program code sections of a computer program are saved, the program code sections being loadable into and/or executable in a block creation unit to make the block creation unit execute the method for inserting a further data block into a first ledger according to an embodiment of the invention when the program code sections are executed in the block creation unit.

In another embodiment, the invention relates to a block verification unit for verifying a further data block to be inserted into a second ledger, wherein the second ledger comprises data blocks, comprising the following units:

interface, configured for receiving the second ledger,
furthermore configured for receiving the further data block, wherein the further data block comprises a further medical dataset and a further link information, wherein the further link information comprises a hash of at least one of the data blocks of the second ledger,
calculation unit, configured for verifying the further link information based on the second ledger,
furthermore configured for, in the case of a positive verification, inserting the further data block into the second ledger.

In another embodiment, the invention relates to a computer program product comprising a computer program, the computer program being loadable into a memory unit of a block verification unit, including program code sections to make the block verification unit execute the method for verifying a further data block to be inserted into a second ledger according to an embodiment of the invention when the computer program is executed in the block verification unit.

In another embodiment, the invention relates to a computer-readable medium, on which program code sections of a computer program are saved, the program code sections being loadable into and/or executable in a block verification unit to make the block verification unit execute the method for verifying a further data block to be inserted into a second ledger according to an embodiment of the invention when the program code sections are executed in the block verification unit.

In another embodiment, the invention relates to a ledger synchronization system for inserting a further data block into a first ledger and into a second ledger, comprising a block creation unit according to an embodiment of the invention, and comprising a block verification unit according an embodiment of the invention.

In another embodiment, the invention relates to a computer program product comprising a computer program, the computer program being loadable into a memory unit of a ledger synchronization system, including program code sections to make the ledger synchronization system execute the method for inserting a further data block into a first ledger and into a second ledger according to an embodiment of the invention when the computer program is executed in the ledger synchronization system.

In another embodiment, the invention relates to a computer-readable medium, on which program code sections of a computer program are saved, the program code sections being loadable into and/or executable in a ledger synchronization system to make the ledger synchronization system execute the for inserting a further data block into a first ledger and into a second ledger according to an embodiment of the invention when the program code sections are executed in ledger synchronization system.

In another embodiment the invention relates to a calculation unit for determining identical persons using a first ledger, wherein a further data block was included into the first ledger, configured for selecting a first medical dataset contained in the first ledger, wherein the first medical dataset comprises an identifier of a first per son, furthermore configured for selecting a second medical dataset contained in the first ledger, wherein the second medical dataset is different from the first medical dataset, and wherein the second medical dataset comprises an identifier of a second person, furthermore configured for determining whether the first person and the second person are identical based on the identifier of the first person and the identifier of the second person.

In another embodiment the invention relates to a computer program product comprising a computer program, the computer program being loadable into a memory unit of a calculation unit, including program code sections to make the calculation unit execute the method for determining identical persons using a first ledger according to an embodiment of the invention when the computer program is executed in the calculation unit.

In another embodiment the invention relates to a computer-readable medium, on which program code sections of a computer program are saved, the program code sections being loadable into and/or executable in a calculation unit to make the calculation unit execute the method for determining identical per sons using a first ledger according to an embodiment of the invention when the program code sections are executed in the calculation unit.

In another embodiment the invention relates to a calculation unit for determining identical persons using a first ledger, wherein a further data block was included into the first ledger, configured for selecting a first medical dataset contained in the first ledger, wherein the first medical dataset comprises an identifier of a first person, furthermore configured for selecting a second medical dataset contained in the first ledger, wherein the second medical dataset is different from the first medical dataset, and wherein the second medical dataset comprises an identifier of a second person, furthermore configured for determining whether the first person and the second person are identical based on the identifier of the first person and the identifier of the second person.

The invention relates in another embodiment to a method for using a first ledger for verifying the experience of a medical professional, comprising the steps of receiving the first ledger with an interface, the step of receiving an identifier of the medical professional with the interface, the step of receiving an identifier of an educational action with the interface, the step of determining the relevant data blocks of the first ledger with a calculation unit, wherein a relevant data block is a data block of the first ledger comprising a relevant medical dataset, and wherein a relevant medical dataset is a medical dataset comprising the identifier of the medical professional and the identifier of the educational action, and the step of determining an education parameter based on the relevant data blocks with the calculation unit. An alternative wording for the method for using a first ledger for verifying the experience of a medical professional is method for using a first ledger for determining an education parameter. The inventors have recognized that based on the first ledger the experience or the education parameter can be determined and/or verified being safe of forgery. The interface can be the interface of the block creation unit, and the calculation unit can be the calculation unit of the block creation unit. Alternatively, the interface can be the interface of the block verification unit, and the calculation unit can be the calculation unit of the block verification unit. Alternatively, the interface can be the interface of further computation node, and the calculation unit can be the calculation unit of the further computation node.

In another embodiment the invention relates to an experience verification unit for verifying the experience of a medical professional using a first ledger after inserting a further data block according to an embodiment of the invention, comprising:
interface, configured for receiving the first ledger,
furthermore configured for receiving an identifier of the medical professional, furthermore configured for receiving an identifier of an educational action, calculation unit, configured for determining the relevant data blocks of the first ledger, wherein a relevant data block is a data block of the first ledger comprising a relevant medical dataset, and wherein a relevant medical dataset is a medical dataset comprising the identifier of the medical professional and the identifier of the educational action, furthermore configured for determining an education parameter based on the relevant data blocks.

In one embodiment the invention relates to a block creation unit for inserting a further data block into a first ledger (LDG), wherein the first ledger comprises data blocks, comprising the following units:

interface, configured for receiving a further medical dataset, wherein the further medical dataset is a log of an access of an entity to a medical apparatus, wherein the further medical dataset comprises an identifier of the medical apparatus and an identifier of the entity accessing the medical apparatus, calculation unit, configured for determining the further data block, where in the further data block comprises the further medical dataset and a further link information, and wherein the further link information comprises a hash of at least one of the data blocks of the first ledger, furthermore configured for inserting the further data block into the first ledger.

BRIEF DESCRIPTION OF THE DRAWINGS

The properties, features and advantages of this invention, its embodiments and embodiments described above, as well as the manner they are achieved, become clearer and more understandable in the light of the following description and embodiments, which will be described in details in the context of the drawings. This following description does not limit the invention on the contained embodiments. Same components or parts can be labeled with the same reference signs in different figures. In general the figures are not for scale. In the following.

DETAILED DESCRIPTION OF EXAMPLE EMBODIMENTS

Figure 1:
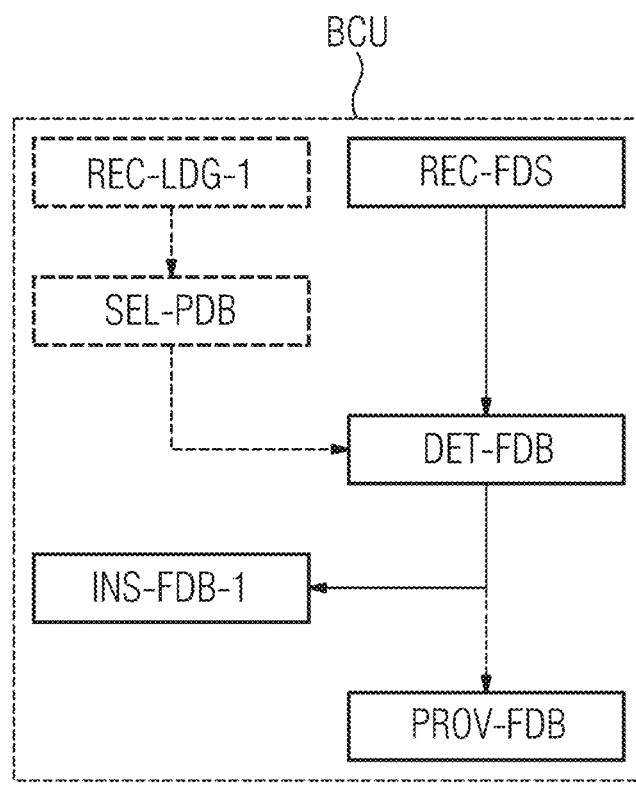
FIG. 1 displays a flowchart of a first embodiment of the method for inserting a further data block into a first ledger.

At least one embodiment of the invention relates to a method for inserting a further data block into a first ledger, comprising the step of receiving a further medical dataset with an interface, furthermore comprising the step of determining the further data block with a calculation unit, wherein the further data block comprises the medical dataset and a link information, wherein the further link information comprises a hash of at least one of the data blocks of the first ledger, furthermore comprising the step of including the further data block into the first ledger with the calculation unit.

The inventors have recognized that using the described methods a medical dataset can revision-safely be stored in a ledger database. In particular, by using a link information comprising a hash value of at least one of the data blocks of the first ledger a manipulation of the at least one of the data blocks can be detected by inspecting the link information of the first data block. This increases the revision-safety of the first ledger, because in or der to manipulate the at least one of the data blocks, also the further data block and all other possible successors of the further data block being included at a later stage have to be manipulated.

In particular, the interface is an interface of a block creation unit. In particular, the calculation unit is a calculation unit of the block creation unit. In particular, the first ledger can be stored within a memory unit, in particular within a memory unit of the block creation unit.

In general a ledger is a certain type of database. In particular, the ledger is a distributed ledger, which is a certain type of a decentralized database. In particular, the ledger is distributed in the sense that there are several copies of (at least parts of) the ledger in different memory units, wherein the memory units are spatially distributed. The ledger comprises multiple records, wherein the multiple records can be identified with database entries. In particular, the multiple records are organized as data blocks. In particular, the records are created by different entities, in particular different nodes of a network, and stored with the different entities, in particular within the different nodes if the records. In other words, the construction and maintenance of the records is typically not performed by a central authority, but independently by nodes of the network. In typical cases, all nodes of the network maintain one copy of the ledger.

In general, updating the ledger is typically based on a consensus mechanism, wherein a consensus mechanism ensures that the different copies of the distributed ledger match, also in the cases of a delayed communication between the entities storing the copies of the distributed ledger.

In general the data blocks are the elementary data records of the ledger. In particular, a data block is an immutable data structure, which means that a data block cannot be changed or modified. This implies that changes to the ledger can only be performed by adding or removing data blocks.

In particular the immutability of a data block can be ensured by storing a hash value of the data block within the data block or outside the data block.

In particular, a first data block of the ledger and a second data block of the ledger can be linked. This link can be an undirected or a directed link. In particular, a link of the first data block and the second data block is present, if the first data block comprises a link information related to the second data block and/or if the second data block comprises a link information related to the first data block.

In particular, the further data block is a data block of the first ledger.

The medical dataset may comprise data corresponding to a medical entity, wherein a medical entity can be a patient, a group of patients, a population of patients, a medical professional, a group of medical professionals, a medical institution, a group of medical institutions, and/or similar entities.

In general a medical professional can be a person performing or training di agnostic or therapeutic actions related to patients, or assisting in diagnostic or therapeutic actions related to patients. Furthermore, a medical professional may also be a person involved in maintenance or operation of a medical apparatus, of medical equipment or a medical facility. In particular, a medical professional can be a physician, a technologist, a radiologist, a nurse, a hygienist, or a technician.

A medical institution may be a hospital, a medical research facility, a medical practice, a outpatient department, a certain part of a hospital, a company developing and/or producing medical apparatuses and/or parts of medical apparatuses, or any group comprising one or several of the mentioned examples. A medical institution may also be any other institution in the medical context.

The medical dataset can comprise a medical data record or can be identical with the medical data record. The medical data record can comprise a medical image dataset. Such medical image dataset is acquired from the patient using a medical imaging apparatus, e.g. a magnetic resonance apparatus, a single photon emission tomography (SPECT) apparatus, a positron emission tomography (PET) apparatus, a computed tomography apparatus, an ultrasound apparatus, an X-ray apparatus, a C-arm apparatus or a combined medical imaging apparatuses formed by any combination composed of the aforementioned imaging modalities. The medical image dataset can also comprise automatically, semi-automatically or manually generated processing information, such as segmented organs, con tour information, registration information, etc.

The medical data record can also comprise medical data acquired or derived from other medical apparatuses which are not medical imaging apparatuses.

Such other medical apparatuses can e.g. be a treatment apparatus, e.g. a radiotherapy device, a lithotripsy device, a laser treatment device, an infusion pump or an interventional treatment device. The medical data can also stem from an apparatus for intensive medicine, a mobile monitoring device, a respiratory device, an anesthetic machine, an ECG device, an EEG device, a blood pressure measurement device, an infusion device or a dialysis device. The medical data record can also comprise laboratory diagnostics or genetic information.

The medical data record can also comprise a complete or part of an electronic health record of a patient. Therefore, the medical data record can comprise information about a disease history of the patient. The medical data record can also contain annotation information, which describes automatically, semi-automatically or manually generated diagnostic findings in the medical dataset. The medical data record can also comprise demographic metadata related to the patient, such as gender, age, weight, size, etc.

Other medical data which can be considered by those skilled in the art can also be part of the medical data record.

Further examples for medical datasets and medical data records may also be found in the different embodiments of the invention, which are described in the following description.

A further medical dataset is a medical dataset. In particular a further medical dataset is a medical dataset not already comprised by a data block of the first ledger.

The data block comprises the medical dataset if the data block comprises data related to the medical dataset. In particular, the data related to the medical dataset can be a link to the medical dataset, wherein the medical dataset is stored not in the data block, but at another location. In particular, the another location can be a Webserver or a cloud storage. In particular, the data related to the medical dataset is the medical data set. In particular, the data related to the medical dataset is a hash value of the medical dataset.

The further data block comprises the further medical dataset if the further data block comprises data related to the further medical data set.

It is not essential for embodiments of the invention that the further link information comprises a hash of at least one of the data blocks of the first ledger. The usage of the hash of at least one of the data blocks allows verifying that the at least one of the data blocks was not altered after the determining of the link information, in particular after determining the hash. In other words, the term "hash of at least one of the data blocks" can be replaced with the term "data integrity information of at least one of the data blocks" within the claims and within the whole application. In particular, by the data integrity information of at least one of the data blocks a manipulation and/or altering of the at least one of the data blocks can be recognized or determined. For the same reasons, the term "hash of at least one of the data blocks" can be replaced with the term "data integrity information of at least one of the data blocks" within the claims and within the whole application also for a link information different from the further link information.

The term "hash value based on a data block of the first ledger" can be used as synonym for "hash of a data block of the first ledger". In particular, the hash of a data block of the first ledger can be a hash only of a subset of information contained in the data block of the first ledger. In particular, the hash of another data block of the first ledger contained in the further data block can be a hash of a subset of information contained in the another data block combined with a subset of information contained in the further data block.

By comprising a hash of at least one of the data blocks of the first ledger the further link information or another link information is related to the at least one of the data blocks of the first ledger. So the term "the further link information is related to a data block" can be used as a synonym for "the further link information comprises a hash information of a data block".

It is also possible that the further data block comprises several further link informations, each of the several further link informations comprising a hash of another data block of the first ledger; it is also possible that a further link information comprises hashes of several other data blocks of the ledger. Equivalently, it is also possible that a data block of the first ledger comprises several further link informations, each of the several further link informations comprising a hash of another data block of the first ledger, it is also possible that a link information of a data block of the first ledger comprises hashes of several other data blocks of the ledger. It is possible that a link information contained in a data block of the first ledger comprises a hash of the data block.

In particular, if a link information comprises a hash, the link information can be identical with the hash. In particular, of the further link information comprises a hash, the further link information can be identical with the hash.

In general a hash of a data block is the result of a hash function being applied to the data block, the result of a hash function being applied to a subset of information contained in the data block, or the result of a hash function being applied to a combination of a first subset of information contained in the data block and a second subset of information, wherein the second subset of information is a subset of information of the data block that contains or will contain the hash.

In general a hash function is a function that maps data of arbitrary size to data of a fixed size. In particular, the hash function is a cryptographic hash function. In particular, a cryptographic hash function is a deterministic function; in particular the output of the hash function does only depend on the input of the hash function. In particular, a cryptographic hash function can be calculated in a fast manner for all input values. In particular, a cryptographic hash function is only brute-force invertible, i.e. given the output of a cryptographic hash function it is only possible to calculate the corresponding input of the cryptographic hash function by calculating the cryptographic hash function for a large amount of input values (i.e. a brute-force attack). In other words, finding the input value corresponding to the output value of a cryptographic hash function is an intractable problem. In particular, finding a first input value and a second input value of a cryptographic hash function that lead to an identical output value is an in tractable problem. In particular, a cryptographic hash function is scattering; i.e. even correlated inputs of the cryptographic hash function lead to uncorrelated outputs of the cryptographic hash function.

In particular, a hash function can calculate a Merkle root of the input data, in particular by computing hashes within a Merkle tree.

In particular, a first data block is denoted as parent data block or parent of a second data block, if the second data block comprises link information related to the first data block. In this case, the second data block is de noted as child data block or child of the first data block. Another term for parent data block is "directly preceding data block" or "direct predecessor". Another term for child data block is "directly succeeding data block" or "direct successor".

In particular, a first data block is denoted as preceding data block or predecessor of a second data block, if there is a third data block so that the first data block is a parent data block or a predecessor data block of the third data block, and so that the third data block is a parent data block or a predecessor data block of the second data block. In this case, the second data block is denoted as succeeding data block or successor of the first data block. In other words, a first data block is a predecessor of the second data block (or equivalently, a second data block is a successor of the first data block) if there is an uninterrupted chain of link informations relating from the second data block to the first data block, possibly involving other data blocks.

In particular, a ledger can incorporate the structure of a mathematical graph. In this case, each data block of the data blocks corresponds to a graph node, and a link information contained by the second data block related to the first data block corresponds to a directed graph edge from a second graph node to a second graph node, wherein the first graph node corresponds to the first data block, and wherein the second graph node corresponds to the second data block.

In general, inserting the further data block into the first ledger means storing the further data block as additional data block of the first ledger. In particular, the further data block is stored in the same memory location where at least one of the data blocks of the first ledger is already stored.

According to a further embodiment of the invention, the first ledger comprises data blocks, wherein each of the data blocks comprises a medical dataset and a link information, wherein the link information comprises a hash of at least one of the data blocks of the first ledger. The inventors recognized that linking data blocks of the first ledger using hashes of data blocks allows detecting modifications of the first ledger, and renders the first ledger re vision-safe.

According to a further embodiment of the invention, the method for inserting a further data block into a first ledger comprises the step of receiving the first ledger with the interface. The inventors have recognized that by receiving the first ledger when executing the method the first ledger need not to be stored in a memory unit permanently.

In particular, the calculation unit is the calculation unit of the block creation unit. In particular, the step of receiving the first ledger can be executed before or after the step of receiving the further medical dataset. In particular, the step of receiving the first ledger can also be executed in parallel to the step of receiving the further medical dataset. In other words, the steps of receiving the first ledger and of receiving the further medical datasets are independent.

According to a further embodiment of the invention, the method for inserting a further data block into a first ledger comprises the step of selecting a parent data block from the data blocks of the first ledger with the calculation unit; wherein the further link information comprises a hash of the parent data block. The inventors have recognized that by selecting the parent data block the structure of the ledger can be determined flexibly, in particular by selecting a parent data block it can be selected the contents of which data block should be verified by the further link information of the further data block.

In particular, the calculation unit is the calculation unit of the block creation unit. In particular, the step of selecting the parent data block can be executed before or after the step of receiving the further medical dataset.

In particular, the step of selecting the parent data block can also be executed in parallel with the step of receiving the further medical dataset. In other words, the steps of selecting the parent data block and of receiving the further medical dataset are independent.

According to a further embodiment of the invention there is no successor data block of the parent data block. In other words, the parent data block is selected from a subset of data blocks of the first ledger, wherein for each data block of the subset of each data block there is no successor data block. The inventors have recognized that by selecting the parent data block from the data blocks without successor longer chains of data blocks are generated within the first ledger, which makes it harder for an attacker to manipulate the ledger.

According to a further embodiment of the invention, the first ledger comprises an origin data block, and wherein the parent data block is selected based on its distance from the origin data block. In particular, the probability for selecting a data block of the first ledger as parent data block decreases with increasing distance from the origin data block. The inventors have recognized that by selecting the parent data block based on its distance from an origin data block longer chains of data blocks are generated within the first ledger, which makes it harder for an attacker to manipulate the ledger.

In particular, an origin data block of the data blocks of the first ledger which does not comprise a link information, or that comprise a link information related to itself. In other words, the origin data block is not the successor of another data block in the first ledger. In other words, there is no parent data block of an origin data block in the first ledger.

In particular, the distance between a first data block and a second data block of the first ledger is the minimal number of link informations that need to be followed for getting from the first data block to the second data block. Another term for distance between a first data block and a second data block is the number of generations between the first data block and the second data block.

In particular, the distance between the first data block and the first data block is 0. In particular, the distance between the first data block and the second data block is 1, if the first data block is the parent or the child of the second data block. In particular, the distance between the first data block and the second data block different from the first data block is infinite, if the first data block is neither the predecessor nor the successor of the second data block. It is also possible to use a constant offset for calculating the distance between all data blocks in a ledger.

If the distributed ledger incorporates the structure of a directed mathematical graph, the distance between a first data block and a second data block is the graph distance between a first graph node and a second graph node, where in the first graph node corresponds to the first data block, and the second graph node corresponds to the second data block.

According to a further embodiment of the invention, the first ledger comprises exactly one origin data block. The inventors have recognized that by using a first ledger with exactly one origin data block longer chains of data blocks are generated within the first ledger, which makes it harder for an attacker to manipulate the ledger.

According to a further embodiment of the invention, the parent data block is a data block with a maximal distance from the origin data block. In particular, if a there are more than one origin data blocks in the first ledger, the parent data block is a data block with a maximal distance from one of the origin data blocks. In particular, if there are more than one origin data blocks in the first ledger, the parent data block is a data block with a maximal sum of distances to all of the origin data blocks. The inventors have recognized by maximizing the distance to one or several origin data blocks, longer chains of data blocks are generated within the first ledger, which makes it harder for an attacker to manipulate the ledger.

According to a further embodiment of the invention, each of the data blocks of the first ledger comprises a weight parameter, wherein the parent data block is selected based on its weight parameter. The inventors have recognized that using weight parameters for selecting a parent data block a prioritization of data blocks to get one or more successors can be achieved. Since having one or several successor data blocks means that the parent data block is harder to manipulate, also a prioritization of revision-safety can be achieved.

In general the weight parameter can correspond to the importance and/or reliability of the data block that contains the weight parameter. In particular, a weight parameter can be an integer or a float number, which can optionally be restricted to values within an open, a semi-open or a closed interval. In particular, the weight parameter of a data block can be based on the calculations done to execute the consensus mechanism.

In particular the data block can comprise a weight parameter if the step of determining a link information is based on a consensus algorithm. In particular, if the consensus mechanism is a proof of work, the weight parameter can be based on the mathematical riddle to be solved. In particular, if the consensus mechanism is a proof of stake, the weight parameter can be based on the stake used for determining the link information. In particular, if the consensus mechanism is a proof of storage, the weight parameter can be based on the amount of storage utilized for determining the link information.

According to a further embodiment of the invention, the weight parameter of a data block in the first ledger is based on a weight parameter of a preceding data block of the data block. The inventors have recognized that using cascading weights the prioritization of data blocks to get one or more successors can also take place for next generation successors, which also contributes to a prioritization of revision-safety.

According to a further embodiment of the invention, the step of selecting the parent data block is based on a Markov chain Monte Carlo algorithm, and wherein the Markov chain Monte Carlo algorithm samples the data blocks of the first ledger based on their weights. The inventors have recognized that using a Markov chain Monte Carlo algorithm a selection of the parent data block is possible based on its weight, without accessing the weights of all or of a majority of data blocks of the first ledger.

In general, a Markov chain Monte Carlo algorithm generates a series of data blocks (possibly containing repetitions) by choosing a next data block of the series according to a transition probability. In particular, the transition probability is based only on the last data block in the series of data blocks and the next data block of the series of data blocks. In particular, the transition probability is chosen so that the probability for a data block to occur in the series of data blocks corresponds to a given probability distribution, in particular a probability distribution in terms of the weights of the data blocks. In particular, the transition probability is chosen to fulfill the detailed balance conditions.

According to a further embodiment of the invention, the data blocks of the first ledger form a directed acyclic graph. The inventors have recognized that by using a directed acyclic graph a unique temporal and/or causal relationship between the data blocks can be formed.

A directed acyclic graph is a finite, directed graph with no direct cycles.

In other words, a directed acyclic graph consists of finitely many vertices and edges, with each edge directed from a first vertex to a second vertex, such that there is no way to start at one of the vertices of the graph and follow a consistently-directed sequence of edges that loops back to the vertex. In other words, a directed acyclic graph is a directed graph that has a topological ordering.

A first ledger or the blocks of a first ledger can be interpreted as graph, if the blocks of the first ledger are interpreted as the nodes of the graphs. An edge is present directed from a second data block to a first data block, if the link information contained in the second data block is related to the first data block. In this case, the second data block is a successor of the first data block, and the first data block is a parent data block of the second data block.

According to a further embodiment of the invention, the further link information is based on the further medical dataset. In particular, the link information of a data block of the data blocks of the first ledger is based on the medical dataset comprised by the data block. The inventors have recognized that a (further) link information based on the (further) medical dataset makes a manipulation of the (further) data block more difficult.

According to a further embodiment of the invention, the further link information comprises a hash of the further medical dataset. In particular, the link in formation of a data block of the data blocks of the first ledger comprises a hash of the medical dataset comprised by the data block. The inventors have recognized that a (further) link information comprising a hash of the (further) medical dataset makes a manipulation of the (further) data block more difficult.

According to a further embodiment of the invention, the further data block comprises a Merkle root of the parent data block and/or of the further medical dataset. The inventors recognized that using a hash function based Merkle root allows a faster verification of the data the Merkle root hash is based on.

In general, a Merkle root is based on a Merkle tree, in particular, the Merkle root is based on the root of a Merkle tree. In general, a Merkle tree is a tree in which every leaf node comprises a hash of a data item and every non leaf node is comprises a hash of the hashes of its child nodes. An alternative name of Merkle tree is hash tree. According to a further embodiment of the invention determining the further link information comprises the execution of a consensus algorithm. The inventors recognized that by using a consensus algorithm a synchronization of the first ledger with another ledger can be guaranteed, wherein the another ledger is stored within a device spatially separates from the block creation unit.

According to a further embodiment of the invention determining the consensus algorithm comprises a proof of work, a proof of storage, a proof of stake and/or a proof of elapsed time. In particular, the consensus algorithm is equivalent to a proof of work, a proof of storage, a proof of stake or a proof of elapsed time. The inventors recognized that by using such determining step one the one hand side a consensus between several units storing copies of the first ledger can be reached, and on the other hand side the revision-safety of the first ledger can be improved.

In general, a proof of work is a measure required by an entity to perform an action in a system, in particular by a computer to perform an action within a network, to reduce the possible number of actions in a certain time interval. In general, proof of work can also be interpreted as an economic measure to deter denial of service attacks and other service abuses such as spam on a network by requiring some work from a system using a service. In general the action to be performed is an asymmetric action, meaning that the resources needed for performing the action are higher than resources needed for verifying that the action actually has been performed. In particular, a proof of work can be a challenge-response proof of work or a solution-verification proof of work.

In particular, a proof of work is a CPU-bound proof of work, a memory-bound proof of work or a network-bound proof of work. In particular, for a CPU-bound proof of work more calculation steps have to be executed by a calculation unit, in particular a processor, in particular a central processing unit (an acronym is "CPU"), to perform the action than to verify that the action actually has been performed. In particular, for a memory-bound proof of work the size of the memory, in particular the size of a random access memory (an acronym is "RAM") or of the hard disk (an acronym is "HD"), needed for per forming the action is higher than the size of the memory needed for verifying that the action actually has been performed. In particular, for a network-bound proof of work more communication actions or communications actions with a higher latency have to be performed for performing the action than for verifying that the action actually has been performed.

In particular, the action to be performed for a proof of work, in particular for a CPU bound proof of work, is calculating the inverse of a one-way function, in particularly by calculating the one-way function multiple times and checking whether the result of the one-way function has a desired property or equals a desired value. In general, a one-way function is a function that can computed by a polynomial time algorithm, but any polynomial time randomized algorithm that attempts to compute a pseudo-inverse for the one-time functions succeeds with negligible probability. Examples for one-way functions is the multiplication of prime numbers (the inverse is the factorization of integer numbers), the Rabin function, the discrete exponential (calculating an exponential modulo an integer, in particular a prime number, the inverse function is the discrete logarithm), cryptographic hash functions, integer multiplication of points on elliptic curves over finite fields, or one-way functions based random linear codes or based on the subset sum problem.

In particular, the action to be performed for a memory-bound proof of work includes the computation of a memory bound function. In particular, the action to be performed for a memory bound proof of work can comprise finding a subgraph or a cycle of a given length in a given random graph or random structure. In particular, the graph can be given by giving an initial seed being the input to a function, in particular a hash function, in order to efficiently define the graph, without storing or communicating the whole graph.

In particular, a network-bound proof of work can comprise communication with several network nodes, wherein the access of one or more network nodes is delayed by network latency or by the accessed networks. In particular, a network-bound proof of work can comprise downloading certain data stored on different network nodes.

In particular, a proof of work can be based on one of the following methods, problems or functions: calculating integer square root modulo a large prime, Weaken Fiat-Shamir signatures, Ong-Schnorr-Shamir signatures, partial hash inversion, hash sequences, Diffie-Hellman-based puzzles, moderate, mbound, Hokkaido, Cuckoo Cycle, Merkle tree based and/or guided tour puzzle protocol.

A subtype of a proof of work is proof of research, wherein a proof of research is a proof of work which results can be used for research purpose, in particular in the field of mathematics, computer science and physics. In particular, a proof of research can comprise finding a prime number with certain properties. In particular, a proof of research can also comprise working on tasks within a scientific computing grid, like the CERN grid or within BOINC.

In general proof of storage means that the ability to create the further block by the block creation unit, or the ability to determine the further link information by the calculation unit, is based on an amount of data storage provided by the block creation unit. Another name for proof of storage is "proof of capacity".

In particular, a proof of storage may utilize a proof of work mechanism by storing precalculated results of the proof of work mechanism on a storage medium, wherein for determining the further link information it is necessary to access the storage medium, and wherein the ability for determining the further link information is based on the amount of precalculated results stored within the storage medium.

In general, proof of stake means that only one block creation unit or a small amount of block creation units from a plurality of block creation units can determine a link information or create a block that is accepted as valid from other nodes of the network. The selection of the one block creation unit or the small amount of block creation units can depend on a random selection, an amount of digital items assigned to the block creation units (in other words, an account balance assigned to or associated with a block creation unit), or an age of digital items assigned to the block creation units. In particular, a digital item can be a token or a unit of a cryptocurrency, and an account can comprise several such tokens or units. Another word for the amount of such tokens or cryptocurrency units is size of stake.

Furthermore, there can also be other protocols for selection the one block creation unit or the small block creation units, for example by defining certain master block creation units, or by introducing checkpoints.

In particular, the one block creation unit or the small amount of block creation units can be selected in a random way based on the hash value of the size of stake, e.g. by only accepting a further data block from the one block creation unit with the smallest the hash value, or by only accepting a further data block from the small amount of block creation units with the n smallest the hash values, wherein n is an integer number. Alternatively, a proof of stake can also be based on the size of stake and/or on the time a certain token or cryptocurrency unit was assigned to or associated with a block creation unit. In particular, the proof of stake can be based on the "Slasher" protocol or the "Casper" protocol. In general the ownership of a token or a cryptocurrency unit can be proven by having access to a private key of an asymmetrical encryption key pair comprising the private key and a public key. To proof the possession of the private key without publishing the private key, the private key can be used for generating signatures, which then can be published. In particular, a token or a cryptocurrency unit is assigned to or associated with a block creation unit if the block creation unit stores the private key.

The usage of a proof of stake consensus has the advantage there the costs for the hardware executing the proof of stake can be reduced significantly with respect to a proof of work consensus, which allows to have a hardware being distributed broadly, an thus increasing the robustness against attacks based on hardware distribution. Furthermore, for the use of a proof of stake consensus the total power consumption of the hardware executing the proof of stake consensus is significantly reduced compared to a proof of work consensus. Furthermore, but depending on the actual implementation of the proof of stake protocol, the time intervals between including further blocks into the distributed ledger can be reduced compared to a proof of work protocol.

In general, a proof of elapsed time means that the creation of a new block by a block creation unit, in particular the determination of the further link information, is based on elapsed time in the block creation unit or in the calculation unit. In particular, a proof of elapsed time may be based on se cure instruction execution. In particular, the secure instruction execution can be done my using a secure environment and utilizing trustworthy functions, in particular a secure hardware environment. Another name for the se cure environment is "trusted execution environment"; an example for a trusted executed environment is the product feature "Software Guard Extensions". In particular, a trusted execution environment comprises central processing unit (an acronym is "CPU") instruction codes that allows user-level code to allocate private regions of memory (sometimes called enclaves) that are protected from processes running at higher privilege levels. In particular, the proof of elapsed time can be based on a timer or time counting function executed in such an enclave, so that it is not possible for any other process to manipulate the timer. In particular, the probability for creating a new block or determining the further link information can be proportional to the elapsed time.

According to a further embodiment of the invention the further data block comprises a nonce, and wherein the consensus algorithm is based on the nonce. In particular, each of the data blocks of the first ledger comprises a nonce.

The inventors recognized that using a consensus algorithm based on a nonce, the execution of the consensus algorithm can be verified efficiently.

In general, a nonce is a data item that can be chosen arbitrarily by the creator of the further data block without affecting the actual content of the further data block. In particular, the usage and/or the content of the further medical dataset are not affected by the choice of the nonce. In general, changing the nonce also changes a hash of the further data block.

In particular, a consensus algorithm is based on a nonce if in order to exe cute the consensus algorithm a nonce has to be selected by the creator of the further data block so that the further data block fulfills a certain requirement, in particular so that the hash of the further data block fulfills a certain requirement.

According to a further embodiment of the invention, the method for inserting a further data block into a first ledger furthermore comprises the step of a receiving a requirement for a hash of the further data block with the inter face, and the step of determining the nonce of the further data block with the calculation unit, wherein the hash of the further data block fulfills the requirement. The inventors recognized that by having to determine a nonce so that a hash of the further data block fulfills the requirement is an efficient consensus algorithm, in particular an efficient proof of work. Since a hash function is a one-way function, the only way to determine the nonce is to try different nonces, possibly a huge number of nonces, but a verification of the execution of the consensus algorithm can be done by calculating the hash function only once.

According to a further embodiment of the invention, wherein the hash of the further data block is a number, wherein the requirement for the hash of the further data block is that hash of the further data block is smaller than a predefined number. In particular, each hash that can be stored in a digital memory unit can be interpreted as binary number. In particular, the requirement can be that the number in a given representation, in particular in the binary representation or the hexadecimal representation, has a certain amount of leading zeros. The inventors recognized that this requirement is a requirement easy and fast to check.

According to a further embodiment of the invention the first ledger is a block-chain, a blocktree and/or a tangle. The inventors have recognized that by using such a ledger software specially designed for these types of ledgers can be used, leading to a faster implementation of the method.

In particular, the first ledger is a tangle if the first ledger is a directed acyclic graph. In particular, the first ledger is a blocktree, if for each data block in the first ledger (except a single origin data block) there is exactly one parent of the data block. In particular, the first ledger is a blockchain if for each data block in the first ledger (except a single origin data block) there is exactly one successor of the data block in the first ledger; and for each data block in the first ledger (except one block data block) there is exactly one parent of the data block in the first ledger.

According to a further embodiment of the invention, the determining of the further link information comprises a proof of work, and the first ledger is a blockchain. The inventors recognized that by using a blockchain the parent data block can be determined fast and efficient, and that using a proof of work consensus makes it particularly difficult for an attacker to fudge the distributed ledger.

According to a further embodiment of the invention, the determining of the further link information comprises a proof of work, and the first ledger is a blocktree. The inventors recognized that by using a blocktree hierarchical relations between medical data sets contained in the data blocks can be mapped more efficiently, and that using a proof of work consensus makes it particularly difficult for an attacker to fudge the distributed ledger.

According to a further embodiment of the invention, the determining of the further link information comprises a proof of work, and the first ledger is a tangle. The inventors recognized that by using a tangle the proof of work can be executed in parallel for different data blocks as parent data blocks (in particular if including several data blocks from different block creation units), making the method more efficient, and that using a proof of work consensus makes it particularly difficult for an attacker to fudge the distributed ledger.

According to a further embodiment of the invention, the determining of the further link information comprises a proof of stake, and the first ledger is a blockchain. The inventors recognized that by using a blockchain the parent data block can be determined fast and efficient, and that using a proof of stake consensus expedites the calculation of the link information, rendering the method faster and more efficient. According to a further embodiment of the invention the step of determining the further link information comprises a proof of stake, and the first ledger is a blocktree. The inventors recognized that by using a blocktree hierarchical relations between medical data sets contained in the data blocks can be mapped more efficiently, and that using a proof of stake consensus expedites the calculation of the link information, rendering the method faster and more efficient.

According to a further embodiment of the invention, the determining of the further link information comprises a proof of stake, and the first ledger is a tangle. The inventors recognized that by using a tangle the proof of stake or the determination of the link information can be executed in parallel for different data blocks as parent data blocks (in particular if including several data blocks from different block creation units), making the method more efficient, and that using a proof of stake consensus expedites the calculation of the link information, rendering the method faster and more efficient.

According to a further embodiment of the invention, the determining of the further link information comprises a proof of elapsed time, and the first ledger is a blockchain. The inventors recognized that by using a blockchain the parent data block can be determined fast and efficient, and that by using a proof of elapsed time consensus the energy consumption for the consensus algorithm can be reduced.

According to a further embodiment of the invention, the determining of the further link information comprises a proof of elapsed time, and the first ledger is a blocktree. The inventors recognized that by using a blocktree hierarchical relations between medical data sets contained in the data blocks can be mapped more efficiently, and that by using a proof of elapsed time consensus the energy consumption for the consensus algorithm can be reduced.

According to a further embodiment of the invention, the determining of the further link information comprises a proof of elapsed time, and the first ledger is a tangle. The inventors recognized that by using a tangle the proof of stake or the determination of the link information can be executed in parallel for different data blocks as parent data blocks (in particular if including several data blocks from different block creation units), making the method more efficient, and that by using a proof of elapsed time consensus the energy consumption for the consensus algorithm can be reduced.

According to a further embodiment of the invention, the first ledger comprises a sidechain, wherein the sidechain is a blockchain, a blocktree and/or a tangle. The inventors have recognized that by using sidechains multiple data blocks can be included into the ledger before without executing a possible consensus mechanism.

According to a further embodiment of the invention, the first ledger is only accessible from within a trusted network. The inventors recognized that allowing access only from within a trusted network improves the data protection. Furthermore fraudulent manipulations of first ledger are made more difficult, because a manipulating entity must have access to the trusted network.

In general, a trusted network comprises entities or network nodes that authorized by a central authority to access the first ledger and/or to include further data blocks into the first ledger. All other entities or network nodes not contained in the trusted network are not authorized by the central authority to access the first ledger and/or to include further data blocks into the first ledger. A common name for a first ledger accessible only from within a trusted network is "consortium ledger". In the case the first ledger is a blockchain, a common name for the first ledger accessible only from within a trusted network is "consortium blockchain". Other known terms are "permissionless ledger" or "permissionless blockchain", which are used in contrast to the terms "permissioned ledger" or "permissioned blockchain".

According to a further embodiment of the invention the further data block and/or the further medical dataset comprise a smart contract.

In general, a smart contract comprises program elements which can be executed by the block creation unit, in particular the calculation unit of the block creation unit, or any other device. In particular, the program elements can comprise source code, scripting language and/or compiled machine code. In particular, a smart contract can be executed. In particular, a smart contract is documented in a distributed ledger, by the further data block and/or the further medical dataset being documented in the distributed ledger. In particular, a smart contract can comprise conditions in terms of program logic, and consequences in terms of program logic, wherein the consequences are activated or executed if certain conditions are fulfilled.

According to a further embodiment of the invention the method of including the further data block into the first ledger comprises the step of transferring cryptocurrency from a first account to a second account by the calculation unit. According to a further embodiment of the invention transferring cryptocurrency comprises including a transaction log into the further medical dataset. In particular, the calculation unit is the calculation unit of the block creation unit. The inventors have recognized that by such an automatical transfer of cryptocurrency a payment process related to the medical dataset can be initiated efficiently.

In general a cryptocurrency is a digital asset or a digital medium which can be exchanged between different entities, wherein methods of cryptography are used for transferring cryptocurrencies from a first entity to a second entity, for the creation of a new amount of cryptocurrency and/or for verifying transfers of cryptocurrency from a first entity to a second entity. In particular, a cryptocurrency is a digital currency. Cryptocurrency can be stored in accounts (another term is "wallet"), in particular, an account corresponds to a asymmetric key pair comprising a private key and a public key, wherein the private key must be known to transfer cryptocurrency from the account to another account, and wherein the public key must be known to transfer crypto currency from another account to the account.

In general, transferring a certain amount of cryptocurrency from a first account to a second account comprises creating a transaction log, wherein the first account corresponds to a asymmetric key pair comprising a first private key and a first public key, and wherein the second account corresponds to an asymmetric key pair comprising a second private key and a second public key, and wherein the transaction log comprises the second public key and at least one key of the first private key and the first public key, and wherein the transaction log furthermore comprises the amount of cryptocurrency being transferred. In particular, a transaction log can also comprise a signature based on the amount of cryptocurrency being transferred and the second public key, signed with the first private key.

In particular, transferring a certain amount of cryptocurrency is executed by including the transaction log into a data block of the first ledger. In particular, for trusting such a transfer of a certain amount of cryptocurrency, there must be multiple other data blocks being child of the data block comprising the transaction log.

According to a further embodiment of the invention, the method for including the further data block into the first ledger comprises the step inducing the transfer of cryptocurrency by means of a smart contract with the calculation unit. In particular, the calculation unit is the calculation unit of the block creation unit. The inventors recognized that inducing the transfer of cryptocurrency by means of a smart contract the cryptocurrency can be transferred automatically, without the possibility for an attacker to e.g. consume a service without payment.

According to a further embodiment of the invention, the method for inserting a further data block into a first ledger comprises the step of receiving a second ledger with a block verification unit, wherein the second ledger comprises data blocks, the step of transmitting the further data block with the interface to the block verification unit, the step of verifying the further link information based on the second ledger with the block verification unit, and, in the case of a positive verification, the step of inserting the further data block into the second ledger with the calculation unit. The inventors recognized that by these additional steps the first ledger and the second ledger can be synchronized, even if the block creation unit and the block verification unit are spatially separated.

In particular, the receiving of a second ledger is executed with an interface of the block verification unit. In particular, the step of transmitting the further data block is executed with the interface of the block creation unit and with the interface of the block verification unit. In particular, the step of verifying the further link information is executed with a calculation unit of the block verification unit. In particular, the step of inserting the further data block into the second ledger is executed with the calculation unit of the block verification unit.

According to a further embodiment of the invention, each of the data blocks of the second ledger comprises a medical dataset and a link information, wherein the link information comprises a hash of at least one of data block of the second ledger. The inventors recognized that by these properties of the second ledger the integrity of the second ledger can be ensured.

According to a further embodiment of the invention, the second ledger comprises the at least one parent data block of the further data block, wherein the step of verifying the further link information is based on the at least one parent data block of the further data block. The inventors recognized that by using a verification based on the at least one parent data block of the further data block ensures that a correct link between the further data block and the data blocks in the second ledger can be established, which ensures the integrity of the second ledger after the insertion of the further data block.

According to a further embodiment of the invention in the step of verifying the further link information the hash of the at least one parent data block is compared with the hash contained in the further link information. The inventors have recognized that by such a comparison of the hashes the integrity of the second ledger after inserting the further data block can be guaranteed.

According to a further embodiment of the invention, determining the further link information comprises the execution of a consensus algorithm, wherein verifying the further link information comprises verifying the actual execution of the consensus algorithm. The inventors have recognized that by verifying the actual execution of the consensus algorithm fraudulent attacks, in particular trying to destroy the synchronization of the first and the second ledger, can be complicated or made impossible.

According to a further embodiment of the invention, the method for inserting a further data block into a first ledger comprises the step of receiving a requirement for a hash of the further data block with the block verification unit, wherein verifying the further link information comprises verifying that the hash of the further data block fulfills the requirement. In particular, the step of receiving the requirement is executed by the interface of the block verification unit. The inventors that a verification based on the requirement can be executed fast and with only low computational effort.

According to a further embodiment of the invention, the hash of the further data block is a number, wherein the requirement for the hash of the further data block is that hash of the further data block is smaller than a predefined number. The inventors that a verification based on the smaller than a predefined number requirement can be executed fast and with only low computational effort.

At least one embodiment of the invention is furthermore related to a method for verifying a further data block to be inserted into a second ledger, wherein the second ledger comprises data blocks, comprising the step of receiving the second ledger with an interface, the step of receiving the further data block with the interface, wherein the further data block comprises a further medical dataset and a further link information, wherein the further link information comprises a hash of at least one of the data blocks of the second ledger, the step of verifying the further link information based on the second ledger with the calculation unit, and, in the case of a positive verification, the step of inserting the further data block into the second ledger with the calculation unit. The inventors recognized that this method the second ledger can be synchronized with a first ledger, wherein the first ledger is stored in a block creation unit that determined the further data block, even if the block creation unit and the block verification unit are spatially separated.

In particular, the interface is an interface of a block verification unit. In particular, the calculation unit is a calculation unit of a block verification unit.

According to a further embodiment of the invention, each of the data blocks of the second ledger comprises a medical dataset and a link information, wherein the link information comprises the hash of at least one data block of the second ledger. The inventors recognized that by these properties of the second ledger the integrity of the second ledger can be ensured.

According to a further embodiment of the invention, the second ledger comprises the at least one parent data block of the further data block, and wherein the step of verifying the further link information is based on the at least one parent data block of the further data block. The inventors recognized that by using a verification based on the at least one parent data block of the further data block ensures that a correct link between the further data block and the data blocks in the second ledger can be established, which ensures the integrity of the second ledger after the insertion of the further data block.

According to a further embodiment of the invention the step of verifying the further link information the hash of the at least one parent data block is compared with the hash contained in the further link information. The inventors have recognized that by such a comparison of the hashes the integrity of the second ledger after inserting the further data block can be guaranteed.

According to a further embodiment of the invention, the further link information is based on a consensus algorithm, wherein verifying the further link information comprises verifying the actual execution of the consensus algorithm. The inventors have recognized that by verifying the actual execution of the consensus algorithm fraudulent attacks, in particular trying to destroy the synchronization of the first and the second ledger, can be complicated or made impossible.

According to a further embodiment of the invention, the method for verifying a further data block to be inserted into a second ledger furthermore comprises the step of receiving a requirement for a hash of the further data block with the interface, wherein verifying the further link information comprises verifying that the hash of the further data block fulfills the requirement. In particular, the step of receiving the requirement is executed by the inter face of the block verification unit. The inventors that a verification based on the requirement can be executed fast and with only low computational effort.

According to a further embodiment of the invention, the hash of the further data block is a number, wherein the requirement for the hash of the further data block is that hash of the further data block is smaller than a predefined number. The inventors that a verification based on the smaller than a predefined number requirement can be executed fast and with only low computational effort.

In another embodiment the invention relates to a block creation unit for inserting a further data block into a first ledger, wherein the first ledger comprises data blocks, comprising the following units:
  interface, configured for receiving a further medical dataset,
  calculation unit, configured for determining the further data block, where in the further data block comprises the further medical dataset and a further link information, wherein the further link information comprises a hash of at least one of the data blocks of the first ledger, and furthermore configured for inserting the further data block into the first ledger.

In particular the block creation unit for inserting a further data block into a first ledger can be configured to execute the method for inserting a further data block into a first ledger according to the invention and its embodiments. The block creation unit is configured to execute the method and its embodiments by the interface and the calculating unit being configured to execute the respective method steps.

The block creation unit can be realized as a data processing system or as a part of a data processing system. Such a data processing system can, for ex ample, comprise a cloud-computing system, a computer network, a computer, a tablet computer, a smartphone or the like. The block creation unit can comprise hardware and/or software. The hardware can be, for example, a processor system, a memory system and combinations thereof. The hardware can be configurable by the software and/or be operable by the software.

In another embodiment, the invention relates to a medical apparatus comprising a block creation unit.

In another embodiment, the invention relates to a computer program product comprising a computer program, the computer program being loadable into a memory unit of a block creation unit, including program code sections to make the block creation unit execute the method for inserting a further data block in to a first ledger according to an embodiment of the invention when the computer program is executed in the block creation unit.

In another embodiment, the invention relates to a computer-readable medium, on which program code sections of a computer program are saved, the program code sections being loadable into and/or executable in a block creation unit to make the block creation unit execute the method for inserting a further data block into a first ledger according to an embodiment of the invention when the program code sections are executed in the block creation unit.

The realization of the invention by a computer program product and/or a computer-readable medium has the advantage that already existing block creation units can be easily adopted by software updates in order to work as proposed by the invention. The computer program product can be, for example, a computer program or comprise another element apart from the computer program. This other element can be hardware, for example a memory device, on which the computer program is stored, a hardware key for using the computer program and the like, and/or software, for example a documentation or a software key for using the computer program.

In another embodiment, the invention relates to a block verification unit for verifying a further data block to be inserted into a second ledger, wherein the second ledger comprises data blocks, comprising the following units:
  interface, configured for receiving the second ledger,
  furthermore configured for receiving the further data block, wherein the further data block comprises a further medical dataset and a further link information, wherein the further link information comprises a hash of at least one of the data blocks of the second ledger,
  calculation unit, configured for verifying the further link information based on the second ledger,
  furthermore configured for, in the case of a positive verification, inserting the further data block into the second ledger.

In particular the block verification unit for verifying a further data block to be inserted into a second ledger can be configured to execute the method for verifying a further data block to be inserted into a second ledger according to an embodiment of the invention and its embodiments. The block verification unit is configured to execute the method and its embodiments by the interface and the calculating unit being configured to execute the respective method steps.

The block verification unit can be realized as a data processing system or as a part of a data processing system. Such a data processing system can, for example, comprise a cloud-computing system, a computer network, a computer, a tablet computer, a smartphone or the like. The block verification unit can comprise hardware and/or software. The hardware can be, for example, a processor system, a memory system and combinations thereof. The hardware can be configurable by the software and/or be operable by the software.

In another embodiment, the invention relates to a computer program product comprising a computer program, the computer program being loadable into a memory unit of a block verification unit, including program code sections to make the block verification unit execute the method for verifying a further data block to be inserted into a second ledger according to an embodiment of the invention when the computer program is executed in the block verification unit.

In another embodiment, the invention relates to a computer-readable medium, on which program code sections of a computer program are saved, the program code sections being loadable into and/or executable in a block verification unit to make the block verification unit execute the method for verifying a further data block to be inserted into a second ledger according to an embodiment of the invention when the program code sections are executed in the block verification unit.

The realization of the invention by a computer program product and/or a computer-readable medium has the advantage that already existing block verification units can be easily adopted by software updates in order to work as proposed by the invention.

The computer program product can be, for example, a computer program or comprise another element apart from the computer program. This other element can be hardware, for example a memory device, on which the computer program is stored, a hardware key for using the computer program and the like, and/or software, for example a documentation or a software key for using the computer program.

In another embodiment, the invention relates to a ledger synchronization system for inserting a further data block into a first ledger and into a second ledger, comprising a block creation unit according to an embodiment of the invention, and comprising a block verification unit according an embodiment of the invention.

In particular the ledger synchronization system for inserting a further data block into a first ledger and into a second ledger can be configured to exe cute the method for inserting a further data block into a first ledger and into a second ledger according to the invention and its embodiments. The block verification unit is configured to execute the method and its embodiments by the block creation unit, in particular the interface and the calculation unit of the block creation unit, and the block verification unit, in particular the interface and the calculation unit of the block creation unit, being configured to execute the respective method steps.

The ledger synchronization system can be realized as a data processing system or as a part of a data processing system. Such a data processing system can, for example, comprise a cloud-computing system, a computer network, a computer, a tablet computer, a smartphone or the like. The ledger synchronization system can comprise hardware and/or software. The hardware can be, for example, a processor system, a memory system and combinations thereof. The hard ware can be configurable by the software and/or be operable by the software.

In another embodiment, the invention relates to a computer program product comprising a computer program, the computer program being loadable into a memory unit of a ledger synchronization system, including program code sections to make the ledger synchronization system execute the method for inserting a further data block into a first ledger and into a second ledger according to an embodiment of the invention when the computer program is executed in the ledger synchronization system.

In another embodiment, the invention relates to a computer-readable medium, on which program code sections of a computer program are saved, the program code sections being loadable into and/or executable in a ledger synchronization system to make the ledger synchronization system execute the for inserting a further data block into a first ledger and into a second ledger according to an embodiment of the invention when the program code sections are executed in ledger synchronization system.

The realization of an embodiment of the invention by a computer program product and/or a computer-readable medium has the advantage that already existing ledger synchronization systems can be easily adopted by software updates in order to work as proposed by a embodiment of the invention.

The computer program product can be, for example, a computer program or comprise another element apart from the computer program. This other element can be hardware, for example a memory device, on which the computer program is stored, a hardware key for using the computer program and the like, and/or software, for example a documentation or a software key for using the computer program.

In the following embodiments of the invention are described which can be used for logging the access of entities to medical data records, in particular for creating a revision-safety audit trail of accesses to medical data records within the first ledger. In other words, the first ledger is then a cumulative log of the access of entities to medical data records. Such a revision-safety audit trail or log can in particularly be used to prove that a certain entity has accessed a certain medical data record, an in cases of an unauthorized and/or abusive access, to sanction the entity having accessed the medical data record unauthorized or abusively. In particular, such information can be used to proof a violation of privacy rules, e.g. if a person abusively accessed medical data not in the interest of the patient (e.g. because he is in a personal relationship with the patient, or if the patient is a public figure). Furthermore, such an access log can be valuable for insurance cases, for example to proof that a certain entity (in particular a physician) in fact accessed a certain medical data record, but negligently did not recognize a diagnosis in the certain medical data record, or did not initiate a correct treatment.

In particular, in the described embodiments the further data block and/or the data blocks contained in the first ledger can have the same structure. In other words, features and advantageous embodiments described for the further data block can also be applied for the data blocks contained in the first ledger, and vice versa.

According to a further embodiment of the invention the further medical is a log of an access of an entity to a medical data record, wherein the further medical dataset comprises an identifier of the medical data record and an identifier of the entity accessing the medical data record. The inventors have recognized that this embodiment of the invention allows to revision-safely log access to medical data records. Such a method can be used for checking whether a medical professional only accessed medical data records which are necessary for him to perform his professional work. Furthermore such a method can be used to proof that a certain entity has actually accessed the medical data record, within an insurance case to proof that the entity has overlooked a finding within the medical data record.

An identifier of the medical data record can generally be used to unambiguously identify the medical data record. In particular, the identifier of the medical data record can be equal to the medical data record. Alternatively, the identifier of the medical data record can be a hash of the medical data record. It is also possible that an identifier of the medical data record comprises other data which allows an unambiguous identification of a medical data record, comprising e.g. the time of the creation of the medical data record, the place of the creation of the medical data record, and/or an identifier of the patient related to the medical data record.

In general an entity can directly or indirectly access a data record, in particular a medical data record. So an entity can be a person, a group of per son, a legal entity (such as a company), a group of legal entities, or an object, in particular an information technology object as a server, a client, a storage medium, or a computer. In particular, an entity can be a medical professional like an employee of a hospital, a physician, a nurse or technical staff of a hospital, or any group thereof. In particular, an entity can be a hospital, a medical practice, or any group thereof.

An identifier of the entity accessing the medical data record can generally be used to unambiguously identify the entity accessing the medical data record. In particular, if the entity is a person accessing the medical data record, the identifier of the entity can comprise the name of the person accessing the medical data record, the data of birth of the person accessing the medical data record, an ID of the person accessing the medical data record (e.g. the social insurance number, the ID number, a driving license number, or a passport number) and/or the employer of the person accessing the medical data record. In particular, if the entity is a company (e.g. a hospital), the identifier of the identity can comprise the company name. In particular, the identifier of the entity accessing the medical data record can comprise the IP address of a computer used by the entity accessing the medical data record. In particular, the identifier of the entity accessing the medical data record can be based on a public key or on a private key related with the entity accessing the medical data record.

According to a further embodiment of the invention the identifier of the medical data record is a hash value of the medical data record. The inventors have recognized that the memory requirement of a hash value of the medical data record is smaller than the memory requirement for the medical data record itself, which leads to a reduced memory requirement for the further data block. Furthermore a hash of the medical data record is sensitive even to small changes in the medical data record, which complicates counterfeiting and/or manipulating the medical data record.

According to a further embodiment of the invention the further medical dataset furthermore comprises a timestamp corresponding to the time of the access of the entity to the medical data record. The inventors recognized that by including the timestamp the traceability of the access log can be increased.

According to a further embodiment of the invention the identifier of the entity is based on a private key assigned to the entity. In general, the private key assigned to the entity is not included into the identifier itself, into the further data block or into the further medical dataset. The inventors recognized that in general the private key assigned to an entity is only known to the entity, and not to another entity. So an identifier based on the private key assigned to the entity can only be generated by the entity itself, a person authorized by the entity or a technical device belonging to the entity, and cannot be manipulated by another entity.

According to a further embodiment of the invention the identifier of the entity comprises a signature signed with the private key assigned to the entity.

The inventors recognized that using a signature signed with the private key allows other entities to verify the identifier of the person using the public key associated with the private key assigned to the entity. Furthermore, including a signature signed with the private key assigned to the entity does not expose the private key to another entity.

In particular, the signature is a digital signature. In general a signature relies on an asymmetric key pair comprising a private key and a public key, originating from an asymmetrical cryptography system. A public key is corresponding with a private key or vice versa, if the private key and the public key form an asymmetric key pair.

In particular, a signature is the output of a signing algorithm, wherein the signing algorithm takes as first input the data to be signed (also denoted as "message") and as second input a private key. In particular, a signature is signed with a private key, if the private key was used as second input for the signing algorithm when creating the signature. In particular, a signature is based on certain data, if the certain data was used as first input for the signing algorithm when creating the signature.

In particular, for a signing algorithm there exists a signature verifying algorithm, wherein the signature verifying algorithm takes as input a dataset, a signature and a public key, and wherein the output of the signature verifying algorithm determines whether the given signature is the output of the signing algorithm applied to the dataset with a private key corresponding to the given public key.

In particular, the signature verifying algorithm can verify the validity of a signature without the knowledge of the private key corresponding to the public key. In particular, a private key used to sign a signature cannot be deduced from the signature. In particular, a private key is assigned to an entity if the entity has access to the private key and/or if the entity stores the private key in one of its memory units.

According to a further embodiment of the invention the signature is based on the medical data record, in particular on a hash value of the medical data record. In particular, the signature equals the medical data record or the hash of the medical data record signed with the private key assigned to the entity. The inventors recognized that by using a signature based on the medical data record both the entity accessing the medical data record can be identified, and the actual value of the medical data record accessed by the entity can be recorded. So a signature based on the medical data set undoubtedly documents that that a certain medical data record was accessed by a certain entity.

According to a further embodiment of the invention the medical dataset further more comprises a timestamp corresponding to the time of the access of the entity to the medical data record, and wherein the signature is based on the timestamp. The inventors recognized that using a signature based on the timestamp undoubtedly documents that the access by a certain entity has been performed at the time corresponding to the timestamp.

According to a further embodiment of the invention the step of receiving the further medical dataset comprises the substep of receiving an access request to the medical data record with the interface from the entity, and the substep of determining the further medical dataset based on the access request and based on the data record with the calculation unit. In particular, the calculation unit is the calculation unit of the block creation unit. In particular, the interface is the interface of the block creation unit.

According to a further embodiment of the invention the method for inserting a further data block into a first ledger comprises the step of performing a check of the authorization of the entity to access the medical data record, furthermore in the case of a positive check, the method comprises the step of granting access to the entity. In particular, the method comprises the step of denying access to the entity in the case of a negative check.

The inventors recognized that by combining the check for authorization of an entity to access a medical data record and the logging of the access of the entity to the medical data record the security of the data access increases.

According to a further embodiment of the invention, in the case of a negative check, the method comprises the step of denying access to the entity, wherein the medical dataset comprises a denial record. In particular, a denial record documents that access was denied to a certain entity. The inventors recognized that by including a denial record into the medical dataset unsuccessful access attempts can be documented, which can be used for tracking willful at tacks on the system comprising the medical data records.

In the following embodiments of the invention are described which can be used for revision-safely logging the access of entities to medical apparatuses, comprising the local and/or remote access of service technicians to a certain medical apparatus. In other words, an audit trail of the access of entities to medical apparatuses can be created.

Such an audit trail can be used for example to document the status of a medical apparatus for certain timestamps, e.g. to track which subcomponents or which software version have been used in the medical apparatus. Documentation of this type may be used to fulfill legal requirements, and to store data relevant to regulatory processes and/or for contract fulfillment. Furthermore, such an audit trail can be used to prove that certain service actions have actually been performed, or to log modifications to the medical apparatus to reconstruct possible sources of errors within the medical apparatus.

The following embodiments of the inventions for revision-safely logging the access of entities to medical apparatuses can be executed by the medical apparatus or by a block creation unit supervising the medical apparatus. In other words, the medical apparatus can be identical with the block creation unit, the medical apparatus can comprise the block creation unit, or the medical apparatus can be distinct from the block creation unit.

In particular, in the described embodiments the further data block and/or the data blocks contained in the first ledger can have the same structure. In other words, features and advantageous embodiments described for the further data block can also be applied for the data blocks contained in the first ledger, and vice versa.

According to a further embodiment to the invention the further medical dataset logs an access of an entity to a medical apparatus, wherein the further medical dataset comprises an identifier of the medical apparatus and an identifier of the entity accessing the medical apparatus.

An access of an entity to the medical apparatus is an interaction of the entity with the medical apparatus which possibly or actually changes a status, prerequisites and/or parameters of the medical apparatus. In particular, the access of the entity to the medical apparatus is a service access to the medical apparatus. In particular, the access of the entity to the medical apparatus is not a regular use of the medical apparatus.

The further medical dataset logs the access of the entity to the medical apparatus by comprising data corresponding to the access, which can be used track or reconstruct the access to the medical apparatus.

In particular, a subset of the medical records contained in the data blocks of the first ledger log accesses of a plurality of entities to a plurality medical apparatuses, each medical record of the subset of medical records logging the access of one entity of the plurality of entities to one medical apparatus from the plurality of medical apparatuses, the medical record comprising an identifier of the one medical apparatus from the plurality of medical apparatuses and an identifier of the one entity from the plurality of entities.

The inventors recognized that using a further medical dataset that logs access of an entity to a medical apparatus these accesses can be documented in a revision-safe way. In particular, the first ledger can then be used as an audit trail access to one or several medical apparatuses in order to track changes to the one or several medical apparatuses.

According to a further embodiment of the invention the identifier of the medical apparatus is based on a model number of the medical apparatus and/or on a serial number of the medical apparatus. The inventors recognized that a medical apparatus can be identified efficiently by referring to its model and/or serial number.

According to a further embodiment of the invention the further medical dataset furthermore comprises a timestamp corresponding to the time of the access of the entity to the medical apparatus. The inventors recognized that by including the timestamp the traceability of the access log can be increased.

According to a further embodiment of the invention the identifier of the entity is based on a private key assigned to the entity. The inventors recognized that in general the private key assigned to an entity is only known to the entity, and not to another entity. So an identifier based on the private key assigned to the entity can only be generated by the entity itself, a person authorized by the entity or a technical device belonging to the entity, and cannot be manipulated by another entity.

According to a further embodiment of the invention the identifier of the entity comprises a signature signed with the private key assigned to the entity. The inventors recognized that using a signature signed with the private key al lows other entities to verify the identifier of the person using the public key associated with the private key assigned to the entity. Furthermore, including a signature signed with the private key assigned to the entity does not expose the private key to another entity.

According to a further embodiment of the invention the signature is based on the identifier of the medical apparatus. The inventors recognized that by using a signature based on the identifier of the medical apparatus both the entity accessing the medical apparatus can be identified, and the actual medical apparatus accessed by the entity can be recorded. So a signature based on the identifier of the medical apparatus undoubtedly documents that that a certain medical apparatus was accessed by a certain entity.

According to a further embodiment of the invention the further medical dataset furthermore comprises a timestamp corresponding to the time of the access of the entity to the medical apparatus and/or corresponding to the time of the egress of the entity from the medical apparatus, wherein the signature is based on the timestamp. The inventors recognized that using a signature based on the timestamp undoubtedly documents that the access and/or egress by a certain entity has been performed at the time corresponding to the timestamp.

According to a further embodiment of the invention the access to the medical apparatus is a remote access.

In particular, a remote access to the medical apparatus is a connection to the medical apparatus from a remote location, for example, through a remote access service or virtual private network, wherein a remote access service comprises a host part installed on the medical apparatus and a remote part installed on a device of the entity accessing the medical apparatus. In particular, a remote access service can comprise a remote desktop application.

The inventors recognized that remote accesses to a medical apparatus can be efficiently tracked by the method according to this embodiment of the invention.

According to a further embodiment of the invention the medical dataset comprises the time of access of the entity to the medical apparatus, wherein the time of access corresponds to the time establishing the remote access to the medical apparatus. In particular the establishing of the remote access takes place after receiving an access request and after granting the access re quest. The inventors have recognized that the time establishing the remote access to the medical apparatus is the earliest time for changes to the medical apparatus from remote and thus particularly relevant for tracking changes to the medical apparatus.

According to a further embodiment of the invention the medical dataset comprises the time of egress of the entity from the medical apparatus, wherein the time of egress corresponds to the time terminating the remote access to the medical apparatus. The inventors have recognized that the time terminating the remote access to the medical apparatus is the latest time for changes to the medical apparatus from remote and thus particularly relevant for tracking changes to the medical apparatus.

According to a further embodiment of the invention the method comprises the step of sending a notification message to the owner of the medical apparatus with the interface, wherein the notification message is based on the identifier of the medical apparatus and the identifier of the person accessing the medical apparatus. In particular, the notification message is an electronic message, e.g. an electronic mail or a pop-up window displayed on a display unit of the owner of the medical apparatus.

In particular, an owner of the medical apparatus can be the entity being the legal proprietor of the medical apparatus, or an entity delegated by the legal proprietor of the medical apparatus. In particular, the owner of the medical apparatus can also be an employee or a contractor of the legal proprietor of the medical apparatus.

The inventors recognized that by sending a notification message to the owner of the medical apparatus the owner can recognize remote accesses to its medical apparatus and take counter-measures in case of a malicious access.

According to a further embodiment of the invention the step of sending the notification message is induced by means of a smart contract. In particular, the smart contract is executed by inserting the further data block into the first ledger. In particular, the smart contract regulates that sending the notification message is executed before granting access to the entity or before establishing the remote connection. The inventors recognized that by sending the message by means of a smart contract ensures the actual sending of the message, also in cases of a malicious access.

According to the further embodiment of the invention the access of the entity to the medical apparatus comprises a modification of the medical apparatus, wherein the further medical dataset comprises a record of the modification. The inventors have recognized that by the further medical dataset comprising records of modification a history of the status of the medical apparatus can be documented revision-safely, and can be used for reconstructing the status of the medical apparatus at a certain point in time.

According to a further embodiment of the invention the modification comprises the installation of a hardware component and/or a software component within the medical apparatus, and wherein the medical dataset comprises an identifier of the hardware component and/or software component. In particular, the identifier of the hardware component can be a model number and/or a serial number of the hardware component. In particular, the identifier of a software component can be a version number, a hash value of the source code of the software component and/or a hash value of the machine code of the software component. In particular, a software component can comprise source code or binary or executable code (another term is "machine code"). The inventors recognized that by tracking identifiers of hardware and/or software components being installed modifications of the medical apparatus can be tracked particularly efficient.

According to a further embodiment of the invention the modification comprises the removal of a hardware component and/or a software component within the medical apparatus, and wherein the medical dataset comprises an identifier of the hardware component and/or software component. The inventors recognized that by tracking identifiers of hardware and/or software components being removed modifications of the medical apparatus can be tracked particularly efficient.

According to a further embodiment of the invention the modification comprises an exchange of a first hardware component with a second hardware component and wherein the medical dataset comprises an identifier of the first hardware component and an identifier of the second hardware component, and/or wherein the modification comprises an exchange of a first software component with a second software component and wherein the medical dataset comprises an identifier of the first software component and an identifier of the second software component. The inventors recognized that by tracking identifiers of hardware and/or software components being exchanged modifications of the medical apparatus can be tracked particularly efficient.

According to a further embodiment of the invention the software component is security update for the medical apparatus. In particular, a security update is a set of changes for the medical apparatus fixing security vulnerabilities and/or bugs. Other terms for "security updates" are "patch" or "bugfix". The inventors recognized that there is a special need in recording audit trails of security updates, because the non-appliance of security updates can lead to an imminent threat for the medical apparatus.

According to a further embodiment of the invention the identifier of the software component comprises a software version number. In particular, the identifier of the first software component comprises a software version number of the first software component and the identifier of the second software component comprises a software version number of the second software component. The inventors recognized that a software version number allows an efficient identification of the software component.

According to a further embodiment of the invention the identifier of the hardware component comprises a model number and/or a serial number of the hardware component. In particular, the identifier of the first hardware component comprises a model number and/or a serial number of the first hardware component and the identifier of the second hardware component comprises a model number and/or a serial number of the second hardware component. The inventors recognized that a model number and/or a serial number allow an efficient identification of the hardware component.

According to a further embodiment of the invention the identifier of the hardware component is stored related to the hardware component. In particular, the identifier of the hardware component is stored on a memory unit of the hardware component. The inventors recognized that storing the identifier of the hardware component related to the hardware component enables a fast and simple read-out of the identifier of the hardware component by the medical apparatus.

According to a further embodiment of the invention the hardware component comprises an RFID-Chip, and wherein the identifier of the hardware component is stored on the RFID-Chip. The inventors have recognized that an RFID-Chip can be read without a direct connection between the hardware component and the read out device.

According to a further embodiment of the invention the hardware component comprises a one-dimensional or two-dimensional optical code, and wherein the identifier of the hardware component is stored in the one-dimensional or two-dimensional optical code. According to a further embodiment of the invention the optical code is a barcode. According to a further embodiment of the invention the optical code is a QR-Code or an Aztec-Code. The inventors recognized that an optical code can be read without using electromagnetic radiation, which is advantageously if the optical code is contained in a shielding, wherein the shielding blocks electromagnetic radiation.

According to a further possible embodiment of the invention the modification of the medical apparatus is the use of a consumable material within the medical apparatus and/or the refill of the consumable material at the medical apparatus. The refill of the consumable material can also comprise a replacement of the consumable material.

In general, a consumable material of the medical apparatus is a material that is consumed during at least one of the procedures executed by the medical apparatus. The consumable material can be consumed completely during one procedure, alternatively the consumable material can be consumed only partially during one procedure, so that the consumable material needs to be replaced or refilled only after a certain number of procedures.

Examples for consumable materials are contrast agents for an imaging medical apparatus, reagents for a laboratory medical apparatus, or material which is in direct contact with a patient during the procedure with the medical apparatus and needs to be replaced for hygienic reasons.

In particular in the case of a refill, the consumable material can be identified as described for a hardware replacement part before. In particular, an identifier of the consumable material can be included into the further medical dataset. This can be of use in particular to track the usage of consumable material and to prevent the use of non-authorized consumable material.

The inventors recognized that by storing the use and/or the refill of the consumable material in a distributed ledger, this data can be used to detect the need for additional consumable material at the medical apparatus, and to automatically initiate the refill of the consumable material, to avoid running out of supplies for the consumable material. In particular, automatically initiating the refill of the consumable material can be executed by means of a smart contract. The data can additionally be used for reimbursing the use of the consumable material, without the possibility for manipulating the stock of consumable material, or its amount used.

According to a further possible embodiment of the invention the further medical dataset does not comprise the identifier of the entity accessing the medical apparatus. In other words, it is not essential that the further medical dataset comprises the identifier of the entity accessing the medical apparatus, in particular in the case where the modification of the medical apparatus is the use of a consumable material within the medical apparatus and/or the re fill of the consumable material at the medical apparatus. In other words, all features relating to the identifier of the entity accessing the medical apparatus could be deleted, in particular in the case where the modification of the medical apparatus is the use of a consumable material within the medical apparatus and/or the refill of the consumable material at the medical apparatus. These features are in particular not necessary, because in the case tracking consumable materials it might be not important and/or not possible to detect which entity performed the action to the consumable material.

According to a further possible embodiment of the invention the further medical dataset comprises the amount of consumable material used during a medical procedure with the medical apparatus, and/or wherein the further medical dataset comprises the amount of consumable material refilled at the medical apparatus.

In particular, the amount of the consumable material used and/or refilled can be expressed in terms of units of consumable materials, in terms of volume and/or in terms of mass of the consumable material.

The inventors recognized that by including the amount of the consumable material the need for additional consumable material can be tracked more easily. Furthermore, an exact reimbursement of the medical material used is possible.

According to a further embodiment of the invention the step of receiving the further medical dataset comprises the step of receiving the identifier of the medical apparatus with the interface, the step of receiving the identifier of the person accessing the medical apparatus with the interface, and the step of determining the further medical dataset based on the identifier of the medical apparatus and based on the identifier of the person accessing the medical apparatus. In particular, the interface is the interface of the block creation unit. In particular, the calculation unit is the calculation unit of the block creation unit. According to a further embodiment of the invention the entity performs a modification of the medical apparatus, wherein a record of the modification is created, and wherein the step of receiving the further medical dataset comprises the step of receiving the record of the modification with the interface. Furthermore the step of determining the further medical dataset is based on the record of the modification.

According to a further embodiment of the invention the first ledger documents the number of accesses of the entity to the medical apparatus for implementing a pay-per-use model. The inventors recognized that by the first ledger documenting the number of accesses, this number of accesses can be documented in a revision-safe way. In particular, the entity accessing the medical apparatus cannot deny its access to the medical apparatus, being a prerequisite for implementing a pay-per-use model based on the number of accesses to the medical apparatus.

According to a further embodiment of the invention the first ledger documents the actions the entity executed with the medical apparatus for implementing the pay-per-use model. The inventors recognized that by the first ledger documenting the actions the entity executed, these actions can be documented in a revision-safe way. In particular, the entity performing actions with the medical apparatus cannot deny the performance of these actions with the medical apparatus, being a prerequisite for implementing a pay-per-use model based on the actions performed with the medical apparatus.

According to a further embodiment of the invention, the method furthermore comprises the step of performing a check whether a further access of the entity to the medical apparatus and/or a further action of the entity executed with the medical apparatus is covered by the pay-per-use-model, and, in the case of a positive check, granting access to the medical apparatus to the entity accessing the medical apparatus with the calculation unit. The inventors recognized that by granting access to the medical apparatus only in the case when the pay per use model allows a further access or a further action, a by-pass of the pay-per-use model can.

According to a further embodiment of the invention the method for inserting a further data block comprises the step of granting access to the medical apparatus to the entity accessing the medical apparatus with the calculation unit. In particular, the step of granting access to the medical apparatus can comprise a check of the authentication and/or the authorization of the entity accessing the medical apparatus, wherein the access is only granted if the check has a positive result. In particular, the step of granting access can comprise establishing a remote connection between the medical apparatus and the entity accessing the medical apparatus or a device of the entity accessing the medical apparatus. The inventors recognized that granting access within the method of inserting a further data block into the first ledger leads to a non-disputable log of accesses, also in the case of malfunction of certain network components.

According to a further embodiment of the invention the method for inserting a further data block into a first ledger comprises the step of transferring cryptocurrency from a first account to a second account by the calculation unit, wherein the first account is an account of an owner of the medical apparatus, and wherein the second account is an account of the entity accessing the medical apparatus. In particular, the calculation unit is the calculation unit of the block creation unit. The inventors have recognized that by such an automatic transfer of cryptocurrency a payment process for the remote process can be initiated efficiently.

In the following embodiments of the invention are described which can be used for logging the transfer of medical data records from a first to a second entity, in particular for creating a revision-safety audit trail of transfers of medical data records within the first ledger. In other words, the first ledger is then a cumulative log of the transfers of medical data records from certain entities to certain other entities.

In particular, such a cumulative log can be used to detect and proof unauthorized transfer of medical data. Furthermore, also the consent of for example the patient being the subject of the medical data can be included into the cumulative log, so that one the one hand side the consent can also be stored in a revision-save way, and on the other hand transfers without consent can be tracked.

In particular, in the described embodiments the further data block and/or the data blocks contained in the first ledger can have the same structure. In other words, features and advantageous embodiments described for the further data block can also be applied for the data blocks contained in the first ledger, and vice versa.

According to a further embodiment of the invention the further medical dataset is a log of a transfer of a medical data record from a first entity to a second entity, wherein the further medical dataset comprises an identifier of the medical data record and an identifier of the first entity and the second entity. The inventors recognized that by using this method the transfer of medical data records can be logged in a revision-safety way.

According to a further embodiment of the invention the identifier of the medical data record is a hash value of the medical data record. The inventors have recognized that the memory requirement of a hash value of the medical data record is smaller than the memory requirement for the medical data record itself, which leads to a reduced memory requirement for the further data block. Furthermore a hash of the medical data record is sensitive even to small changes in the medical data record, which complicates counterfeiting and/or manipulating the medical data record.

According to a further embodiment of the invention the further medical dataset furthermore comprises a timestamp corresponding to the time of the transfer of the medical data record. The inventors recognized that by including the timestamp the traceability of the transfer log can be increased.

According to a further embodiment of the invention the identifier of the first entity is based on a private key assigned to the first entity, and/or wherein the identifier of the second entity is based on a private key assigned to the second entity. In general, the private key assigned to the first entity is not included into the first identifier itself, into the further data block or into the further medical dataset. In general, the private key assigned to the second entity is not included into the second identifier itself, into the further data block or into the further medical dataset. The inventors recognized that in general the private key assigned to the first or to the second entity is only known to the first or second entity, and not to another entity. So an identifier based on the private key assigned to the first or second entity can only be generated by the entity itself, a person authorized by the first or second entity or a technical device belonging to the first or second entity, and cannot be manipulated by another entity.

According to a further embodiment of the invention the identifier of the first entity comprises a first signature signed with the private key assigned to the first entity, and/or the identifier of the second entity comprises a second signature signed with the private key assigned to the second entity. The inventors recognized that using a signature signed with the private key al lows other entities to verify the identifier of the first and/or second entity using the public key associated with the private key assigned to the first and/or second entity. Furthermore, including a signature signed with the private key assigned to the first and/or second entity does not expose the private key to another entity.

According to a further embodiment of the invention the first signature and/or the second signature are based on the medical data record, in particular on a hash value of the medical data record. In particular, the first signature and/or the second signature equals the medical data record or the hash of the medical data record signed with the private key assigned to the first entity and/or with the private key assigned to the second entity. The inventors recognized that by using a signature based on the medical data record both entities involved in the transfer of the medical data record can be identified, and the actual value of the medical data record transferred from the first entity to the second entity can be recorded. So a signature based on the medical data set undoubtedly documents that that a certain medical data record was transferred from a first entity to a second entity.

According to a further embodiment of the invention the log dataset furthermore comprises a timestamp corresponding to the time of the transfer of the medical data record, wherein the first signature and/or the second signature are based on the timestamp. The inventors recognized that using a first signature and/or a second signature based on the timestamp undoubtedly documents that the transfer of the medical data record from the first entity to the second entity has been performed at the time corresponding to the timestamp.

According to a further embodiment of the invention the medical data record is a medical data record of a patient, and wherein the medical dataset comprises consent information issued by the patient. In particular, the consent information issued by the patient describes the consent of the patient that the medical data record is transferred from the first entity to the second entity. The consent information may be a signature signed with a private key of the patient. In particular, the signature can be a signature of the identifier of the medical data record and the identifier of the second entity. In particular, the signature can be a signature of the identifier of the medical data record, the identifier of the first entity and the identifier of the second entity. The inventors have recognized that by storing a consent information in the further dataset a consent of a patient for sharing his medical data record can be recorded in a revision-safety way.

According to a further embodiment of the invention the step of receiving the further medical dataset comprises the step of receiving a transfer request from the second entity related to the medical data record by the interface; and wherein the step of receiving the further medical dataset comprises the step of determining the further medical dataset based on the transfer request and based on the medical data record with the calculation unit.

In particular, the step of determining the further medical dataset based on the medical data record is executed after the step of receiving the transfer request. In particular, the interface is the interface of the block creation unit. In particular, the calculation unit is the calculation unit of the block creation unit.

In particular, the medical data record can be stored in a memory unit of the block creation unit. In this case the first entity is equivalent with the block creation unit, or the block creation unit is a subset of the first entity or in possession of the first entity. Alternatively, the medical data record can be stored in a memory unit outside of the block creation unit. In this case, the first entity is not equivalent to the block creation unit.

In general a transfer request can be issued by the second entity and sent to the first entity in order to initiate a transfer of the medical data record from the first entity to the second entity. In particular, the transfer re quest can comprise an identifier of the medical data record to be transferred; in particular the transfer request can comprise an URL associated with the medical data record to be transferred. In particular, the transfer request can also comprise a proof of identity of the second entity, e.g. a signature signed with a private key related to the second entity. Furthermore, the transfer request can also comprise a proof of authorization of the second entity, e.g. a shared secret or a token needed for accessing the medical data record.

According to a further embodiment of the invention the method for inserting a further data block into a first ledger furthermore comprises the step of providing the medical data record to the second entity with the interface. In particular, the interface is the interface of the block creation unit.

According to a further embodiment of the invention the method for inserting a further data block into a first ledger comprises the step of performing a check of the authorization of the second entity to access the medical data record with the calculation unit, wherein the step of providing the medical data record is executed only if the result of the check is positive.

The inventors recognized that by combining the check for authorization of an entity to receive the medical data record and the logging of the transfer of the medical data record from the first entity to the second entity the security of the data transfer increases.

According to further embodiment of the invention the method for inserting a further data block into a first ledger furthermore comprises the step of determining a modified medical data record based on the medical data record with the calculation unit, wherein the modified medical data record comprises the identifier of the second entity, and the step of providing the modified medical data record with the interface.

In particular, the modified medical data record comprises the identifier of the second entity such that the identifier of the second entity is not separate from the actual data of the modified medical data record, but such that the identifier of the second entity is combined with the actual data of the modified medical data record. In particular, the modified medical data record can be the result of a function taking as an input the medical data record and the identifier of the second entity, and giving as an output the modified medical data record. In particular, the modified medical data record can be used in the same way as the medical data record; in particular, a method, an apparatus or an entity working on the medical data record can also work on the modified medical data record without changing its procedures.

The inventors have recognized that by providing a modified medical data record which incorporates the identifier of the second entity a misuse of the modified medical data record can be detected. For example if the second entity shares the modified medical data record without permission, by inspecting the modified medical data record one can determine the origin of the share without permission.

According to a further embodiment of the invention the medical data record comprises a medical image, wherein the modified medical data record comprises the medical image equipped with a watermark, and wherein the watermark comprises the identifier of the second entity. In other words, the modified data record comprises a modified medical image, wherein the modified medical image is the medical image equipped with a watermark. In other words, the modified medical image comprises information of the medical image and in formation of the watermark.

In particular, a watermark is a digital watermark. In general a watermark is a kind of marker covertly embedded in a noise-tolerant signal such as image data. It is also possible to use a watermark in audio or video data. In other words, the watermark comprises hidden information. In particular, watermarks may be used to verify the authenticity or integrity of the image they are embedded in or to show the identity of its owners. In general, watermarks are only perceptible under certain conditions, i.e. after using some algorithm on the image they are contained in. An image may carry several different water marks at the same time. In particular, unlike metadata that is added to the image, a watermark does not change the size of the carrier signal.

The inventors have recognized that using a watermark it is possible to encode the identifier of the second entity into the medical data record in a hidden way, furthermore an image comprising a watermark can be treated with the same algorithms as an image without watermark.

According to a further embodiment of the invention wherein the medical image comprises a background region and a foreground region, and wherein the watermark is located only in the background region of the medical image. In particular, if the modified medical data record comprises a modified medical image, the modified medical image comprises the foreground region of the medical image and a modified background region, wherein the modified background region is the background region of the medical image equipped with the watermark.

A background region of a medical image is the region which is not the image of the patient itself, but of the patient's surrounding. A foreground region of a medical image is the region which is the image of the patient itself. In particular, the background region can be the image of the air surrounding the patient or a patient positioning device like a patient table.

The inventors recognized that equipping only the background region of a medical image with a watermark does not influence the relevant information contained in the foreground region, in particular, the relevant information of the modified medical image is identical to the relevant information of the medical image.

In the following embodiments of the invention are described which can be used for documenting the admission process of a medical apparatus, in particular for creating a revision-safety documentation of the admission process of the medical apparatus within the first ledger. In other words, the first ledger is then a cumulative documentation of the admission process of the medical apparatus.

A first usage example is to track the training process of an artificial intelligence algorithm used for diagnostic or therapeutic purposes, in order to prevent or at least document an over-fitting of the artificial intelligence algorithm. A second usage example is to track study data corresponding to the admission process of a medical device, in particular to exclude that certain subjects of the studies have been used twice in the same study or in similar studies. However, the following embodiments of the invention are not limited to such examples.

In particular, in the described embodiments the further data block and/or the data blocks contained in the first ledger can have the same structure. In other words, features and advantageous embodiments described for the further data block can also be applied for the data blocks contained in the first ledger, and vice versa.

According to a further embodiment of the invention the further medical dataset corresponds to the admission process of a medical apparatus. In particular, the admission process of a medical apparatus can be the admission process of a certain type of medical apparatuses.

In particular, the medical dataset corresponds to the admission process of the medical apparatus if the medical dataset comprises information and/or da- to necessary for the admission process of the medical apparatus. In general, the information and/or data necessary for the admission process of a medical apparatus are regulated by national and/or governmental authorities.

The admission process of a medical apparatus corresponds to all data items and/or actions necessary for receiving an admission of the medical apparatus by a national authority, for maintaining the admission of the medical apparatus, and/or for fulfilling requirements set by a national authority. It is also possible to consider other actions and/or data items which are related to the admission of the medical apparatus as part of the admission process of the medical apparatus.

A medical apparatus may comprise a physical apparatus configured for performing and/or supporting therapeutic and/or diagnostic steps. A medical apparatus may also comprise a non-physical entity, e.g. a software or a computer program product configured for performing or supporting therapeutic or diagnostic steps. In particular, an artificial intelligence algorithm configured for performing and/or supporting therapeutic and/or diagnostic steps can be considered as a medical apparatus or as a part of a medical apparatus. In particular, a medical apparatus may be comprise artificial intelligence algorithm configured for processing medical images. If the medical apparatus comprises an artificial intelligence algorithm, the information and/or data necessary for the admission process of the medical apparatus may comprise training data for the artificial intelligence algorithm.

In general, an artificial intelligence algorithm is a function that maps input data to output data, wherein internal parameters of the function are determined based on training input data. In particular, the parameters may be determined by comparing the output of the function applied to training input data to known output data, this is known as supervised learning. It is also possible to use unsupervised learning or a combination of supervised and unsupervised learning. In the case of supervised learning, the information and/or data necessary for the admission process may comprise pairs of training input data and associated known output data.

The inventors recognized that by documenting information and/or data necessary for the admission process for the admission process of a medical apparatus as further data blocks in a first ledger ensures a revision-safety documentation of the admission process. As a consequence, errors in the admission process of the medical apparatus can be tracked afterwards.

According to a further embodiment of the invention the medical apparatus comprises a trained artificial intelligence algorithm, and wherein the further medical dataset is based on a training dataset used for the training of the artificial intelligence algorithm. In particular, the training dataset is used as an input for the artificial intelligence algorithm during the training. In particular in the case of supervised learning, the training dataset comprises a pair of training input data and known output data, wherein during training the artificial intelligence algorithm is applied to the training input data, and a parameter of the artificial intelligence algorithm is adjusted based on a comparison of the output of the artificial intelligence algorithm and the known output data.

In particular, the further medical dataset is based on a training dataset, if the further medical dataset comprises the training dataset, if the further medical dataset comprises a link or an URL to the training dataset, and/or if the further medical dataset comprises an identifier of the training dataset, in particular a hash of a training dataset.

The inventors recognized that documenting the training of an artificial intelligence algorithm in a distributed ledger enables to verify a correct training of the artificial intelligence algorithm. According to a further embodiment of the invention the step of receiving a further medical dataset comprises the step of receiving the training dataset with the interface, the step of determining a first parameter of the artificial intelligence algorithm with the calculation unit, the step of performing a training step of the artificial intelligence algorithm based on the training dataset with the calculation unit, the step of determining a second parameter of the artificial intelligence algorithm with the calculation unit, and the step of determining the further medical dataset based on the training dataset and based on the first and the second parameter with the calculation unit. The inventors recognized that documenting the training dataset together with the first and the second parameter enables to document the actual effect of using a training dataset for the training of the artificial intelligence algorithm.

According to a further embodiment of the invention the artificial intelligence algorithm comprises an artificial neural network, and wherein the first parameter comprises a weight of an edge of the artificial neural network before performing the training step, and wherein the second parameter comprises the weight of the edge after performing the training step.

In general, an artificial neural networks comprises a set of nodes and a set of (directed) edges connecting nodes. In general, to each edge in the set of edges a weight can be assigned. In particular, if an edge connects the output of a first node with the input of a second node, the weight of the edge corresponds to the weight of the output of the first node in the input of the second node. In particular, a second node can comprise several ingoing edges connected to the output of several first nodes, in this case the weights can be associated with the relative weight of the outputs of the several first nodes in the input of the second node.

According to a further embodiment of the invention the first parameter comprises the weights of all edges of the artificial neural network before performing the training step, and wherein the second parameter comprises the weights of all edges of the artificial neural network after performing the training step.

The inventors have recognized that the change of the weights of one or several edges of the artificial neural network is the relevant parameter changing during a training step of the artificial neural network.

According to a further embodiment of the invention the training dataset comprises a training image. According to a further embodiment of the invention the training dataset comprises a label associated with the training image. The inventors recognized that the training images and the associated labels used for the training of an artificial intelligence algorithm are the relevant data to document the training process of the artificial intelligence algorithm.

According to a further embodiment of the invention the medical dataset comprises an identifier of a person being subject of a medical study. In particular, the study relates to the admission process of a medical device.

In general a medical study is research performed for verifying or disproving a medical hypothesis, in particular in medical science. In particular, a medical hypothesis may be related to the effectiveness of a certain diagnostic or therapeutic medical apparatus, medical method or medication.

A person is subject to a medical study if the medical study utilizes data from the person. In particular, the person subject to the medical study is a subject of the diagnostic or therapeutic medical apparatus, medical method or medication. In particular, the person subject of a medical study can have a certain disease, and the effectiveness of a certain diagnostic or therapeutic medical apparatus, medical method or medication is tested with respect to the patient.

The inventors recognized that documenting persons which are subject of a medical study in a distributed ledger allows to document the medical study itself, in particular, such a distributed ledger can be used for fraud detection. For example, certain types of medical studies depend on so-called virgin subjects, wherein virgin subjects are person that have not been in con tact to a medical treatment. Since such persons are hard to find, fraud can happen by using virgin subjects several times, which means that they are not virgin subjects for all medical studies except the first one. Documenting persons being subjects to a medical study allows to track such fraudulent virgin subjects.

According to a further embodiment of the invention the identifier of a person is a physical parameter of the person uniquely identifying the person. According to another embodiment of the invention the identifier of the person corresponds to a fingerprint of the person, to a DNA sequence of the person or to a bio metrical parameter of the person. In particular a biometrical parameter is a geometrical relationship between certain landmarks of the human body, in particular landmarks of the human face.

The inventors have recognized that using uniquely identifying physical parameters allows to track identities of persons also for persons not having any legal or data driven identity (such as a ID number or a social insurance number).

According to a further embodiment of the invention the medical dataset comprises a first patient parameter corresponding to the person before the medical study, and wherein the medical dataset furthermore comprises a second patient parameter corresponding to the person after the medical study. In particular, the first patient parameter corresponds to the person before an element of the medical study was applied to the patient, and the second patient parameter corresponds to the person after the element of the medical study was applied to the person. Examples for elements being applied to a person are therapeutic actions or medications.

In general, the first patient parameter and the second patient parameter correspond to a physical value of the person being subject of a medical study, for example a laboratory value corresponding to the patient or s diagnostic information corresponding to the patient. In particular, a difference between the first patient parameter and the second patient parameter can indicate a possible effect of the element of the medical study that was applied to the person, e.g. the effectiveness of a medication.

The inventors recognized that by recording the first patient parameter and the second patient parameter in the distributed ledger the single effects of the actions of the study on the study subjects can be recorded in a revision-safety way. In particular, by recording these patient parameters it can be ensured that results of studies are based on all subjects of the studies.

According to a further embodiment of the invention the step of receiving a further medical dataset comprises the step of receiving the identifier of the person being subject of the medical study with the interface, furthermore it comprises the step of determining the further medical dataset based on the identifier of the person being subject of the medical study with the calculation unit. In particular, the calculation unit is the calculation unit of the block creation unit BCU. In particular, the interface is the interface of the block creation unit.

According to a further embodiment of the invention the step of receiving a further medical dataset comprises the step of receiving the identifier of the person being subject of the medical study with the interface, the step of receiving the first patient parameter corresponding to the person before the medical study with the interface, the step of receiving the second parameter corresponding to the person after the medical study with the interface, and the step of determining the further medical dataset based on the identifier of the person being subject of the medical study and based on the first parameter and the second parameter with the calculation unit. In particular, the calculation unit is the calculation unit of the block creation unit BCU. In particular, the interface is the interface of the block creation unit.

According to a further embodiment of the invention the further medical dataset corresponds to the admission process of a medical apparatus by corresponding to a calibration of the medical apparatus.

In general a calibration of a medical apparatus is based on a comparison of an output value of the medical apparatus, in particular a measurement value of the medical apparatus, with a calibration standard of known accuracy. In particular, the calibration of the medical apparatus is a process which changes one or several parameters of the medical apparatus in order to achieve that the output value of the medical apparatus equals the calibration standard of known accuracy. A calibration standard may be an output, in particular a measurement value, of another device, an output of another device generating the object to be measured by the medical device, or an object with known properties to be measured by the medical apparatus. For example, if the medical apparatus is a computed tomography apparatus, a calibration of the medical apparatus may comprise a measurement of a phantom with the computed tomography apparatus, and comparing the measurement with known properties of the phantom. For example, if the medical apparatus is a laboratory device measuring properties of fluids, a calibration can include the measurement of a fluid with known properties, in particular water.

In particular, the calibrated medical apparatus may be identical with the block creation unit. Alternatively, the block creation unit may comprise the calibrated medical apparatus, or the calibrated medical apparatus may comprise the block creation unit.

The inventors recognized that storing further medical datasets corresponding to the calibration of the medical apparatus in the first ledger can be used for storing the fact that a calibration has happened, and advantageously also results of the calibration, in a revision-safe way.

According to a further embodiment of the invention the further medical dataset comprises an identifier of the medical apparatus and a timestamp, wherein the timestamp corresponds to the time of calibration of the medical apparatus. According to a further embodiment the step of receiving the further medical dataset comprises the step of receiving the identifier of the medical apparatus with the interface, and the step of determining the further medical dataset based on the identifier of the medical apparatus with the calculation unit.

The inventors recognized that by including the identifier of the medical apparatus and the timestamp of the calibration into the further medical dataset it can be documented in a revision-safe way that a calibration has been per formed at the included timestamps.

According to a further embodiment of the invention the further medical dataset comprises an identifier of an entity performing the calibration of the medical apparatus. According to a further embodiment of the invention the step of receiving the further medical dataset comprises the step of receiving the identifier of the entity performing the calibration of the medical apparatus with the interface, and the step of determining the further medical dataset based on the identifier of the entity performing the calibration of the medical apparatus, in particular furthermore based on the identifier of the medical apparatus, with the calculation unit.

The inventors recognized that by including the identifier of the entity per forming the calibration of the medical apparatus it can be documented in a revision-safe way by which entity the calibration was performed. This data can be used afterwards to determine the responsible entity if one or several calibration procedures were not executed correctly.

In particular if the calibrated medical apparatus is identical with the block creation unit, or if the calibrated medical apparatus comprises the block creation unit, or if the block creation unit comprises the calibrated medical apparatus, the identifier of the entity performing the calibration can be identical with the entity using the calibrated medical apparatus, in particular the entity logged-in to the calibrated medical apparatus.

According to a further embodiment of the invention the further medical dataset comprises calibration information based on the calibration of the medical apparatus. According to a further embodiment of the invention the step of receiving the further medical dataset comprises step of receiving the calibration in formation with the interface, and the step of determining the further medical dataset based on the calibration information with the calculation unit, in particular furthermore based on the identifier of the medical apparatus and/or on the identifier of the entity performing the calibration of the medical apparatus.

In particular, the calibration information can be based on the output and/or the measurement value of the medical apparatus during used for calibration. Furthermore, the calibration information can be based on calibration standard of known accuracy used for the calibration. Furthermore, the calibration in formation can comprise measures taken for calibrating the medical apparatus, in particular the one or more parameters of the medical apparatus chosen such that the output value of the medical apparatus equals the calibration standard of known accuracy.

The inventors recognized that by including the calibration information into the further medical dataset the process of calibration can be documented in even greater detail.

According to a further possible embodiment of the invention the further medical dataset comprises data documenting the product development of the medical apparatus.

In particular, the medical apparatus can be a hardware apparatus and/or software. The product development of the medical apparatus can comprise developing the hardware and/or writing computer code constituting the software. The product development can additionally comprise quality tests, in particular clinical validations or software tests.

The inventors recognized that by including the further medical dataset comprising data documenting the product development of the medical apparatus this data can be documented in a revision-safe way, at the same time possibly allowing external entities (e.g. regulatory authorities) to access the documentation. In particular this can then be used to document the admission process of the medical device in a revision-safe way.

According to a further possible embodiment of the invention the further medical dataset comprises data describing a certain version of software contained in the medical apparatus.

The certain version of the software can be a version of the software used in production, or an intermediated version of the software compiled (for example for testing purposes) during the development of the software. In particular, all intermediate version of the software can be documented in the distributed ledger. If the medical apparatus is software, the software contained in the medical apparatus is the software forming the medical apparatus.

The inventors recognized that by documenting data describing a certain version of software the development process of the software can be documented in a revision-safe way. In particular, afterwards it can be checked which parts of the software were developed under which circumstances (e.g. who contributed to a certain part of the software, or when the certain part of the software was created). These non-deniable records can be important for retrospective considerations, but also for an efficient documentation of the development process for regulatory authorities.

According to a further possible embodiment the data describing a certain version of the software describes a commit to a source code repository and/or a build within a continuous integration and/or a continuous delivery system.

In particular, a commit to a source code repository can be a dataset describing the difference of the source code between the current version and the previous version committed to the source code repository. In particular, the versions of the software can be reconstructed using a consecutive set of commits.

In particular, a build of a software version corresponds to the machine code generated based on the source code of this software version. In particular, continuous integration is the practice of merging all working copies of developers to the source code repository at least once a working day, preferable several times a working day. In particular, within continuous delivery code is compiled and packaged (e.g. linked to libraries) every time a change is committed to the source code repository, in particular comprising tests by a number of different techniques, possibly including manual and automatic testing.

The inventors recognized that documenting the single steps of a continuous integration and/or a continuous delivery process within a distributed ledger, both agility and traceability of the software development can be ensured, al lowing for documenting the development process efficiently and in a revision-safe manner.

According to a further possible embodiment of the invention the data describing the certain version of the software comprises a hash of the commit to the source code repository and/or a hash of the build within the continuous integration and/or the continuous delivery system.

The inventors recognized that by using a hash the actual source code or the actual build is not documented in the distributed ledger, so that no external entity can access the actual source code or the actual build. At the same time, by storing the actual source code and/or the actual build locally, by documenting the hash within the distributed ledger the same functionality can be achieved as with storing the source code and/or the build directly.

According to a further possible embodiment of the invention the further medical dataset comprises at least one signature signing the data documenting the product development of the medical apparatus. In particular, the signature can be a digital signature based on the private key of the entity developing the medical apparatus (e.g. the manufacturer of the medical apparatus).

The inventors recognized that by including a signature into the further medical dataset documented in the distributed ledger it can be ensured that the data documenting the product development was actually inserted into the further medical dataset and in the distributed ledger by an authorized entity, in particular by the entity developing the medical apparatus. In particular, in this case it is not possible for an unrelated entity to fake an entry into the distributed ledger.

According to a further possible embodiment of the invention the further medical dataset comprises a smart contract, wherein the smart contract regulates the release of the medical apparatus, in particular the release of a certain version of software contained in the medical apparatus.

The inventors recognized that using a smart contract the release of the certain version of software contained in the medical apparatus can be effected automatically and reliably, if a certain set of conditions is fulfilled. In particular, the conditions can also be documented in the distributed ledger or another distributed ledger.

According to a further possible embodiment of the invention the certain version of software is released if the medical dataset comprises a predefined set of signatures signing data describing the certain version of software. In particular, the signatures can be based on private keys of a certain set of entities. The certain set of entities can comprise a number of employees of the developer of the medical apparatus, in particular employees who need to agree with a software version to be released.

The inventors recognized that by the software being released based on a smart contract, if a certain set of signatures is present, the release of the software can be automated and faster than if using signatures on paper. At the same time, the existence of the signatures at the time of the release of the software cannot be disputed, in contrast to standard electronic databases.

According to a further possible embodiment of the invention the further medical dataset comprises a smart contract, wherein the smart contract regulates the access to the data documenting the product development of the medical apparatus. According to a further possible embodiment of the invention the smart contract grants access to the data documenting the product development of the medical apparatus for a regulatory authority.

The inventors recognized that by such a smart contract access can be granted to a regulatory authority and to entities part of the company developing the medical apparatus, wherein at the same time external entities cannot access the possibly secret data documenting the product development of the medical apparatus.

The invention furthermore possibly relates to a method for using a first ledger, wherein a further data block was included into the first ledger according to a method for inserting a further data block into a first ledger, comprising the step of selecting a first medical dataset contained in the ledger by a calculation unit, wherein the first medical dataset comprises an identifier of a first person, furthermore comprising the step of selecting a second medical dataset contained in the ledger by the calculation unit, wherein the second medical dataset is different from the first medical dataset, and wherein the second medical dataset comprises an identifier of a second person, and furthermore comprising the step of determining whether the first person and the second person are identical based on the identifier of the first person and the identifier of the second person with the calculation unit.

In particular, the first person is identical with the second person if the identifier of the first person is identical with the identifier of the second person. Alternatively, the first person can be considered to be identical with the second person if a similarity measure of the identifier of the first person and the identifier of the second person is above a given threshold. In particular, the step of determining whether the first person and the second person are identical can comprise determining a probability of the first person being identical to the second person based on the identifier of the first person and the identifier of the second person, wherein the determination whether the first person and the second person are identical is based on the probability, in particular on whether the probability is above a given threshold.

In particular, the step of selecting a first medical dataset contained in the first ledger can comprise the step of selecting a first data block contained in the first ledger with the calculation unit, wherein the first data block comprises the first medical dataset, and the step of extracting the first medical dataset from the first data block with the calculation unit. In particular, the step of selecting a second medical dataset contained in the first ledge can comprise the step of selecting a second data block contained in the first ledger with the calculation unit, wherein the second data block comprises the second medical dataset, and the step of extracting the second medical dataset from the second data block with the calculation unit.

The calculation unit can be the calculation unit of the block creation unit. Alternatively, the calculation unit can be the calculation unit of the block verification unit. Alternatively, the calculation unit can be the calculation unit of a further computation node.

The inventors recognized that based on the first ledger it can be determined whether there are medical datasets or further medical datasets comprising identifiers of identical persons. So this method can be used to determine whether certain persons have been subject of the same study twice or more of ten, leading to a distorted study results. Furthermore, by recording virgin subjects of medical studies, it can be tested whether a supposed virgin subject is in fact a virgin subject.

According to a further embodiment of the invention the method for using the first ledger, in the case of the first person and the second person being identical, comprises the step providing an alert message with the interface. In particular, the alert message can comprise the identifier of the first person and/or the identifier of the second person. The inventors recognized that using an alert message identical persons can be found faster and more reliable.

According to a further embodiment of the invention the first person is subject of a first medical study and the second person is subject of the second medical study, wherein the first study is identical with the second study. The inventors have recognized that by this method it can be determined whether certain persons have been subject of the same study twice or more often, leading to a distorted study results.

According to a further embodiment of the invention the step of selecting the second medical dataset and the step of determining are applied multiple times.

In particular, the step of selecting the second medical dataset and the step of determining are executed with every medical dataset of a subset of medical datasets contained in the first ledger being the second medical dataset, wherein every medical dataset of the subset of medical datasets comprises the identifier of a second person being subject to the medical study the first person is subject of. The inventors recognized that by using this method it can be determined whether certain persons have been subject of the same study twice or more often, leading to a distorted study results.

In another embodiment the invention relates to a calculation unit for determining identical persons using a first ledger, wherein a further data block was included into the first ledger, configured for selecting a first medical dataset contained in the first ledger, wherein the first medical dataset comprises an identifier of a first person, furthermore configured for selecting a second medical dataset contained in the first ledger, wherein the second medical dataset is different from the first medical dataset, and wherein the second medical dataset comprises an identifier of a second person, furthermore configured for determining whether the first person and the second person are identical based on the identifier of the first person and the identifier of the second person.

In particular the calculation unit for determining identical persons using a first ledger can be configured to execute the method for determining identical persons using a first ledger according to the invention and its embodiments. The calculation unit is configured to execute the method and its embodiments by being configured to execute the respective method steps.

The calculation unit can be realized as a data processing system or as a part of a data processing system. Such a data processing system can, for example, comprise a cloud-computing system, a computer network, a computer, a tablet computer, a smartphone or the like. The calculation unit can comprise hard ware and/or software. The hardware can be, for example, a processor system, a memory system and combinations thereof. The hardware can be configurable by the software and/or be operable by the software.

In another embodiment the invention relates to a computer program product comprising a computer program, the computer program being loadable into a memory unit of a calculation unit, including program code sections to make the calculation unit execute the method for determining identical persons using a first ledger according to an embodiment of the invention when the computer program is executed in the calculation unit.

In another embodiment the invention relates to a computer-readable medium, on which program code sections of a computer program are saved, the program code sections being loadable into and/or executable in a calculation unit to make the calculation unit execute the method for determining identical per sons using a first ledger according to an embodiment of the invention when the program code sections are executed in the calculation unit.

The realization of the invention by a computer program product and/or a computer-readable medium has the advantage that already existing block creation units can be easily adopted by software updates in order to work as proposed by the invention.

The computer program product can be, for example, a computer program or comprise another element apart from the computer program. This other element can be hardware, for example a memory device, on which the computer program is stored, a hardware key for using the computer program and the like, and/or software, for example a documentation or a software key for using the computer program.

In the following embodiments of the invention are described which can be used for documenting educational actions of medical professionals, in particular for creating a revision-safety documentation of the educational actions of medical professional within the first ledger. In other words, the first ledger is then a cumulative documentation of educational actions of medical professionals.

A first usage example is to log educational actions of medical professionals, whose execution is certified or verified by an education entity, for example a number of certain interventional actions done by the medical professional under the supervision of the education entity. A second usage example is to provide synthetically generated data to the medical professional and receive his or her diagnosis of the synthetically generated data, and to record the deviations from the actual diagnosis. Such a method or system can be used for automatically performing educational actions and for automatically recording the success or failure of such educational actions.

In particular, in the described embodiments the further data block and/or the data blocks contained in the first ledger can have the same structure. In other words, features and advantageous embodiments described for the further data block can also be applied for the data blocks contained in the first ledger, and vice versa.

According to a further embodiment of the invention the further medical dataset is related to an educational action of a medical professional, wherein the further medical dataset comprises an identifier of the medical professional and an identifier of the educational action. The inventors recognized that storing educational actions of medical professionals in the first ledger allows for a revision-safe audit trail of the educational actions of medical professionals.

In general a medical professional can be a person performing or training di agnostic or therapeutic actions related to patients, or assisting in diagnostic or therapeutic actions related to patients. Furthermore, a medical professional may also be a person involved in maintenance or operation of a medical apparatus, of medical equipment or a medical facility. In particular, a medical professional can be a physician, a technologist, a radiologist, a nurse, a hygienist, or a technician. In order to become a medical profession al or to be a medical professional, a person must prove its abilities, for example by a certificate (e.g. a university diploma), through acquiring credit points (e.g. CME credits, where CME is an abbreviation for "Continuing medical education", in particular regulated by the Accreditation Council for Continuing Medical Education ACCME and the American Osteopathic Association AOA), or by regularly performing certain tasks.

In general an educational action is an action performed by one or several medical professionals, which is necessary to prove its or their abilities. Performing certain educational actions may be necessary to get a diploma, or to be admitted to work as a medical specialist. Alternatively an educational action may be necessary in order to stay admitted to work as a medical professional, in particular to stay admitted as a medical specialist. Furthermore, an educational action can also be necessary to proof that a medical specialist is familiar with a specific therapeutic or diagnostic action. In particular, an educational action can be a therapeutic or a diagnostic action. Alternatively, an educational action can also be taking a test related to a therapeutic or diagnostic action. As an additional alternative, educational action can be a documented attendance at a conference, or participation in a class room educational session.

According to a further embodiment of the invention the educational action is supervised and/or rated by an education entity, wherein the medical dataset comprises a signature of the identifier of the educational action and the identifier of the medical professional, and wherein the signature is signed by the education entity.

An education entity is an entity supervising, rating and/or confirming a medical action performed by a medical professional. In particular, an education entity can be an experienced medical professional. Furthermore, an education entity can also be an institution, e.g. a university or a hospital, which offers medical professionals the possibility to perform educational actions. In particular, the education entity can also be an employee or any other representative of such an institution. An education entity can also be a software which provides virtual tests to the medical professionals, and rates answers or actions of the medical professional. In general, if an education entity supervises or rates an educational action, a medical professional performs the medical action, and the education entity monitors the medical action, assesses the result medical action and/or interferes in cases the educational action is not performed properly by the medical professional.

According to a further embodiment of the invention the step of receiving the medical dataset comprises the step of providing a medical data record to the medical professional by the interface, wherein a first medical information is assigned to the medical data record, the step of receiving a second medical information from the medical professional by the interface, and the step of determining a comparison value based on the first medical information and on the second medical information by the calculation unit; wherein the medical dataset is based on the comparison value. In particular, the interface is the interface of the block creation unit. In particular, the calculation unit is the interface of the block creation unit.

The inventors recognized that by this embodiment not only the fact that the medical professional has executed an educational action can be recorded, but also the outcome of the educational action can be recorded.

In general, a first medical information and a second medical information are diagnostic information related to the medical data record. In particular, the first medical information is the correct diagnostic information related to the medical data record, and the second medical information is the diagnostic information related to the medical data record related to the medical professional.

In particular, a comparison value is based on the first medical information and the second medical information, if it relates to differences between the first medical information and the second medical information. In particular, a comparison value measures a difference between the first medical information and the second medical information. In particular, a comparison value can be a binary value indication whether the first medical information is equivalent to the second medical information.

According to a further embodiment of the invention the first medical information is a diagnosis information regarding the medical data record determined by another entity, and wherein the second medical information is a diagnosis information regarding the medical data record determined by the medical professional. The inventors recognized that by this embodiment tests of the performance of the medical professional with respect to diagnoses can be recorded.

According to a further embodiment of the invention the medical data record and the first medical information are synthetically generated data. In particular, the medical data record and the first medical information are generated by an artificial intelligence algorithm. In particular, the method for including the further data block into the first ledger can comprise the step of generating synthetically the medical data record and the first medical information. In particular, the step of generating synthetically the medical data record and the first medical information can be based on the artificial intelligence algorithm. In particular, the artificial intelligence algorithm can be based on a generative adversarial network. The inventors recognized that using synthetically generated medical data records and first medical information the training resources for medical professionals can be generated cheaper. This implies that different synthetically generated medical data records and first medical informations can be used for different medical professionals, which makes fraud harder.

According to a further embodiment of the invention the medical data record corresponds to a patient, wherein the first medical information was created by an experienced medical professional. In particular, the experienced medical professional differs from the medical professional. The inventors have recognized that using medical data records corresponding to a patient and first medical informations created by an experienced medical professional have higher quality than synthetically generated medical data records and first medical informations, leading to better educational results.

According to a further embodiment of the invention the medical data record comprises a medical image and/or a medical laboratory report. The inventors recognized that educational actions based on medical images or medical laboratory reports can efficiently be used for automated educational actions, because the diagnosis of medical images and/or medical laboratory reports does not include the interaction between the medical professional and other entities.

According to a further embodiment of the invention the method for including the further data block into the first ledger comprises the step of transferring first cryptocurrency from a first account to a second account by the calculation unit, wherein the second account is an account of the medical professional. In particular, the first account is an account of the education entity. In particular, the amount of first cryptocurrency transferred can be based on the educational action. In particular, the first cryptocurrency can be personalized for the medical professional. In particular, the amount of first cryptocurrency can be monitored through a smart contract and induce the issuance of tamper-proof educational certificate. In particular, the amount of first cryptocurrency can be based on an amount of CME credits, in particular the amount of first cryptocurrency can be directly proportional to an amount of CME credits. The inventors recognized that transferring first cryptocurrency to the medical professional, the amount of educational actions undertaken by the medical professional can be tracked. In particular, a medical professional can prove that he did a certain amount of educational actions by proving that his account holds a certain amount of first cryptocurrency.

According to a further embodiment of the invention the method for including the further data block into the first ledger comprises the step of transferring second cryptocurrency from a first account to a second account by the calculation unit, wherein the first account is an account of the medical professional. In particular, the second account is an account of the educational entity. The inventors recognized that by transferring the second cryptocurrency the medical professional can pay for the educational action. In particular, the transfer of the second cryptocurrency can be induced by means of a smart contract, automatically transferring second cryptocurrency if the medical professional starts, unsuccessfully or successfully completes the educational action.

The invention relates in another embodiment to a method for using a first ledger for verifying the experience of a medical professional, comprising the steps of receiving the first ledger with an interface, the step of receiving an identifier of the medical professional with the interface, the step of receiving an identifier of an educational action with the interface, the step of determining the relevant data blocks of the first ledger with a calculation unit, wherein a relevant data block is a data block of the first ledger comprising a relevant medical dataset, and wherein a relevant medical dataset is a medical dataset comprising the identifier of the medical professional and the identifier of the educational action, and the step of determining an education parameter based on the relevant data blocks with the calculation unit. An alternative wording for the method for using a first ledger for verifying the experience of a medical professional is method for using a first ledger for determining an education parameter. The inventors have recognized that based on the first ledger the experience or the education parameter can be determined and/or verified being safe of forgery. The interface can be the interface of the block creation unit, and the calculation unit can be the calculation unit of the block creation unit. Alternatively, the interface can be the interface of the block verification unit, and the calculation unit can be the calculation unit of the block verification unit. Alternatively, the interface can be the interface of further computation node, and the calculation unit can be the calculation unit of the further computation node.

According to a further embodiment of the invention the education parameter is the number of relevant data blocks. In particular, the education parameter can be the number of relevant data blocks included into the first ledger after a certain time threshold. The inventors recognized that the number of relevant data blocks corresponds to the number of educational action performed by the considered medical professional and is a suitable measure for assessing the experience of the medical professional.

According to a further embodiment of the invention the method for using a first ledger for verifying the experience of a medical professional comprises the step of receiving a minimal educational requirement with the interface, wherein the education parameter is furthermore based on the minimal educational requirement. The inventors have recognized that based on the minimal educational requirement the experience of the medical professional can be assessed fast and efficiently.

According to a further embodiment of the invention the minimal educational requirement is a minimal number of educational actions to be performed, and wherein the education parameter is based on a comparison of the number of relevant data blocks and the minimal number of educational requirements. The inventors recognized that by a comparison of the numbers it can be easily determined whether the experience of a medical professional fulfills the given minimal requirement.

In another embodiment the invention relates to an experience verification unit for verifying the experience of a medical professional using a first ledger after inserting a further data block according to an embodiment of the invention, comprising:
  interface, configured for receiving the first ledger,
    furthermore configured for receiving an identifier of the medical professional,
    furthermore configured for receiving an identifier of an educational action,
  calculation unit, configured for determining the relevant data blocks of the first ledger, wherein a relevant data block is a data block of the first ledger comprising a relevant medical dataset, and wherein a relevant medical dataset is a medical dataset comprising the identifier of the medical professional and the identifier of the educational action,
    furthermore configured for determining an education parameter based on the relevant data blocks.

In particular the experience verification unit can be configured to execute the method for verifying the experience of a medical professional using a first ledger according to the invention and its embodiments. The experience verification unit is configured to execute the method and its embodiments by being the calculation unit and the interface configured to execute the respective method steps.

The experience verification unit can be realized as a data processing system or as a part of a data processing system. Such a data processing system can, for example, comprise a cloud-computing system, a computer network, a computer, a tablet computer, a smartphone or the like. The experience verification unit can comprise hardware and/or software. The hardware can be, for example, a processor system, a memory system and combinations thereof. The hardware can be configurable by the software and/or be operable by the software. In another embodiment the invention relates to a computer program product comprising a computer program, the computer program being loadable into a memory unit of an experience verification unit, including program code sections to make the experience verification unit execute the method for verifying the experience of a medical professional using a first ledger according to an aspect of the invention when the computer program is executed in the experience verification unit.

In another embodiment the invention relates to a computer-readable medium, on which program code sections of a computer program are saved, the program code sections being loadable into and/or executable in an experience verification unit to make the experience verification unit execute the method for verifying the experience of a medical professional using a first ledger according to an embodiment of the invention when the program code sections are executed in the experience verification unit.

The realization of the invention by a computer program product and/or a computer-readable medium has the advantage that already existing block creation units can be easily adopted by software updates in order to work as proposed by the invention.

The computer program product can be, for example, a computer program or comprise another element apart from the computer program. This other element can be hardware, for example a memory device, on which the computer program is stored, a hardware key for using the computer program and the like, and/or software, for example a documentation or a software key for using the computer program.

In the following further embodiments of the invention are described in further detail. The following further embodiments of the invention are partially identical with the embodiments of the invention described before.

Definitions of terms used in the following further embodiments of the invention, as well as advantageous embodiments, features and/or embodiments of the invention described above can also be applied to the following further embodiments of the invention.

The invention is not limited by the following further embodiments, its features or advantageous embodiments.

In one embodiment the invention relates to a method for inserting a further data block into a first ledger, wherein the first ledger comprises data blocks, comprising the step of receiving a further medical dataset with an interface, wherein the further medical dataset is a log of an access of an entity to a medical apparatus, wherein the further medical dataset comprises an identifier of the medical apparatus and an identifier of the entity accessing the medical apparatus, furthermore comprising the step of determining the further data block with a calculation unit, wherein the further data block comprises the further medical dataset and a further link information, wherein the further link information comprises a hash of at least one of the data blocks of the first ledger, and furthermore comprising the step of inserting the further data block into the first ledger with the calculation unit.

It is not essential for the invention that the further link information comprises a hash of at least one of the data blocks of the first ledger. The usage of the hash of at least one of the data blocks allows verifying that the at least one of the data blocks was not altered after the determining of the link information, in particular after determining the hash. In other words, the term "hash of at least one of the data blocks" can be replaced with the term "data integrity information of at least one of the data blocks" within the claims and within the whole application. In particular, by the data integrity information of at least one of the data blocks a manipulation and/or altering of the at least one of the data blocks can be recognized or determined. For the same reasons, the term "hash of at least one of the data blocks" can be replaced with the term "data integrity information of at least one of the data blocks" within the claims and within the whole application also for a link information different from the further link information.

It is not essential for the invention that the further medical dataset is a log of an access of an entity to a medical apparatus, wherein the further medical dataset comprises an identifier of the medical apparatus and an identifier of the entity accessing the medical apparatus. Using this structure for the further medical dataset and/or the first ledger can be used for logging the access of the entity to the medical apparatus. In other words, the further medical dataset can have a different purpose or a different content.

The inventors recognized that by including a further data block into the first ledger, comprising a further medical dataset comprising the defined structure, access of the entity to the medical apparatus can be stored in a revision-safe or non-disputable way, allowing tracking access to certain medical apparatuses or by certain entities.

According to a further embodiment of the invention the identifier of the medical apparatus is based on a model number of the medical apparatus and/or on a serial number of the medical apparatus. The inventors recognized that based on the medical number and/or based on the serial number of the medical apparatus an identifier can be assigned to the medical apparatus in an efficient and unique way.

According to a further embodiment of the invention the identifier of the entity comprises a signature signed with the private key assigned to the entity. The inventors recognized that a signature signed with the private key assigned to the entity proofs that the entity was actually involved in the creation of the identifier, so that no first entity can include a further medical dataset or induce an inclusion of a further medical dataset into the first ledger comprising an identifier of a second entity.

According to a further embodiment of the invention the signature is based on the identifier of the medical apparatus. The inventors recognized that the signature being based on the identifier of the medical apparatus prevents the sig nature to be used in several medical datasets in the first ledger, contributing to the first ledger being tamper-proof.

According to a further embodiment of the invention the access of the entity to the medical apparatus comprises a modification of the medical apparatus, and wherein the further medical dataset comprises a record of the modification, and wherein the step of receiving the further medical dataset comprises the step of receiving the record of the modification with the interface and the step of determining the further medical dataset based on the record of the modification with the calculation unit.

The inventors recognized that by the further medical dataset based on the record of the modification the access of the entity to the medical apparatus can be documented more precisely.

According to a further embodiment of the invention the method for including a further data block into the first ledger comprises the step of sending a notification message to the owner of the medical apparatus with the interface, wherein the notification message is based on the identifier of the medical apparatus and the identifier of the entity accessing the medical apparatus.

In particular, the step of sending the notification message can be induced by means of a smart contract. The inventors recognized that by sending a notification message an unauthorized access of the entity to the medical apparatus can be detected fast by the owner of the medical apparatus, and necessary countermeasures can be taken immediately.

According to a further embodiment of the invention the method for including a further data block into the first ledger comprises the step of granting access to the entity accessing the medical apparatus with the calculation unit, wherein the step of granting access is executed after the step of inserting the further data block into the first ledger. The inventors recognized that by granting access after inserting the further data block into the first ledger it can be ensured that the access is logged before the access actually has taken place, which makes it more difficult for an attacker to manipulate the logging procedure by hindering the inserting of the further data block into the first ledger despite having access to the medical apparatus.

According to a further embodiment of the invention the method for including a further data block into the first ledger comprises the step of transferring cryptocurrency from a first account to a second account by the calculation unit, wherein the first account is an account of an owner of the medical apparatus and wherein the second account is an account of the entity accessing the medical apparatus. In particular, the step of transferring cryptocurrency can be induced by means of a smart contract.

The inventors recognized that by transferring cryptocurrency service actions of the entity accessing the medical apparatus can be billed automatically.

According to a further embodiment of the invention the medical dataset comprises the time of access of the entity to the medical apparatus, wherein the time of access corresponds to the time establishing a remote access to the medical apparatus by the entity, and/or wherein the medical dataset comprises the time of egress of the entity from the medical apparatus, wherein the time of egress corresponds to the time terminating the remote access to the medical apparatus. The inventors recognized that by including the time of access and/or the time of egress the quality of the logging can be increased, in particular, by including the time of access and/or the time of egress not only the fact that an access of the entity to the medical apparatus has happened, but also the actual time or timespan of the access can be stored in a revision-safe way.

According to a further embodiment of the invention each of the data blocks of the first ledger comprises a medical dataset and a link information, the link in formation comprises a hash of at least one of the data blocks of the first ledger. The inventors recognized that by each data block comprising a link information the revision-safety of the first ledger can be improved.

According to a further embodiment of the invention the step of determining the further data block comprises the execution of a consensus algorithm. The inventors recognized that by the execution of a consensus algorithm the revision-safety of the first ledger can be improved.

According to a further embodiment of the invention the first ledger is a block-chain, a blocktree or a tangle. The inventors recognized that by using the described structures of the first ledger the revision-safety of the first ledger can be improved.

According to a further embodiment of the invention the method for including a further data block into the first ledger comprises the step of receiving a second ledger with a block verification unit, the step of transmitting the further data block with the interface to the block verification unit, the step of verifying the further link information based on the second ledger with the block verification unit, and in the case of a positive verification, the step of inserting the further data block into the second ledger with the block verification unit. The inventors recognized that by these additional steps, which basically are a verification of the further data block created by a block creation unit by a block verification unit, the revision-safety of the first ledger can be improved.

In one embodiment the invention relates to a block creation unit for inserting a further data block into a first ledger (LDG), wherein the first ledger comprises data blocks, comprising the following units:
 interface, configured for receiving a further medical dataset, wherein the further medical dataset is a log of an access of an entity to a medical apparatus, wherein the further medical dataset comprises an identifier of the medical apparatus and an identifier of the entity accessing the medical apparatus,
 calculation unit, configured for determining the further data block, where in the further data block comprises the further medical dataset and a further link information, and wherein the further link information comprises a hash of at least one of the data blocks of the first ledger,
 furthermore configured for inserting the further data block into the first ledger.

The block creation unit can be realized as a data processing system or as a part of a data processing system. Such a data processing system can, for ex ample, comprise a cloud-computing system, a computer network, a computer, a tablet computer, a smartphone or the like. The block creation unit can comprise hardware and/or software. The hardware can be, for example, a processor system, a memory system and combinations thereof. The hardware can be configurable by the software and/or be operable by the software.

In one embodiment the invention relates to a computer program product comprising program elements which induce a block creation unit to carry out the steps of the method for inserting a further data block into a first ledger according to one of the claims 1 to 13, when the program elements are loaded into a memory unit of the block creation unit.

The realization of the invention by a computer program product and/or a computer-readable medium has the advantage that already existing block creation units can be easily adopted by software updates in order to work as proposed by the invention.

The computer program product can be, for example, a computer program or comprise another element apart from the computer program. This other element can be hardware, for example a memory device, on which the computer program is stored, a hardware key for using the computer program and the like, and/or software, for example a documentation or a software key for using the computer program.

The properties, features and advantages of this invention, its embodiments and embodiments described above, as well as the manner they are achieved, become clearer and more understandable in the light of the following list of possible embodiments, some of which will be described in details in the context of the. The following list of embodiments does not limit the invention to the listed embodiments. In particular, features of the described embodiments can always be combined or exchanged with one another without limiting or widening the scope of the described invention, whenever such a combination or exchange is meaningful and in the sense of this invention.

Embodiment 1

A method for inserting a further data block into a first ledger, wherein the first ledger comprises data blocks, comprising the following steps:
 receiving a further medical dataset with an interface,
 —determining the further data block with a calculation unit, wherein the further data block comprises the further medical dataset and a further link information,
 wherein the further link information comprises a hash of at least one of the data blocks of the first ledger,
 inserting the further data block into the first ledger with the calculation unit.

Embodiment 2

The method according to embodiment 1, wherein each of the data blocks of the first ledger comprises a medical dataset and a link information, wherein the link information comprises a hash of at least one of the data blocks of the first ledger.

Embodiment 3

The method according to embodiment 1 or 2, comprising:
 receiving the first ledger with the interface.

Embodiment 4

The method according to one of the embodiments 1 to 3, further more comprising the following step:
 selecting a parent data block from the data blocks of the first ledger with the calculation unit;
 wherein the further link information comprises a hash of the parent data block.

Embodiment 5

The method according to embodiment 4, wherein the first ledger does not comprise a successor data block of the parent data block.

Embodiment 6

The method according to embodiment 4 or 5, wherein the first ledger comprises an origin data block, and wherein the parent data block is selected based on its distance from the origin data block.

Embodiment 7

The method according to embodiment 6, wherein the first ledger comprises exactly one origin data block.

Embodiment 8

The method according to one of the embodiments 6 or 7, wherein the parent data block is a data block with a maximal distance from the origin data block.

Embodiment 9

The method according to one of the embodiments 4 to 7, wherein each of the data blocks of the first ledger comprises a weight parameter, and wherein the parent data block is selected based on its weight parameter.

Embodiment 10

The method according to embodiment 9, wherein the weight parameter of a data block of the first ledger is based on a weight parameter of a preceding data block of the data block.

Embodiment 11

The method according to one of the embodiments 4 to 10, where in the step of selecting a parent data block is based on a Markov chain Monte Carlo algorithm, and wherein the Markov chain Monte Carlo algorithm samples the data blocks of the first ledger based on their weights.

Embodiment 12

The method according to one of the embodiments 2 to 11, where in the data blocks of the first ledger form a directed acyclic graph.

Embodiment 13

The method according to one of the preceding embodiments, wherein the further link information is based on the further medical dataset.

Embodiment 14

The method according to embodiment 13, wherein the further link information comprises a hash of the further medical dataset.

Embodiment 15

The method according to one of the preceding embodiments, wherein the further data block comprises a Merkle root of the parent data block and/or of the further medical dataset.

Embodiment 16

The method according to one of the preceding embodiments, wherein determining the further link information comprises the execution of a consensus algorithm.

Embodiment 17

The method according to embodiment 16, wherein the consensus algorithm comprises a proof of work, a proof of stake and/or a proof of elapsed time.

Embodiment 18

The method according to embodiment 16 or 17, wherein the further data block comprises a nonce, and wherein the consensus algorithm is based on the nonce.

Embodiment 19

The method according to embodiment 18, furthermore comprising the steps:
receiving a requirement for a hash of the further data block with the interface,
determining the nonce of the further data block with the calculation unit, wherein the hash of the further data block fulfills the requirement.

Embodiment 20

The method according to embodiment 19, wherein the hash of the further data block is a number, wherein the requirement for the hash of the further data block is that hash of the further data block is smaller than a predefined number.

Embodiment 21

The method according to one of the preceding embodiments, wherein the first ledger is a blockchain, a blocktree and/or a tangle.

Embodiment 22

The method according to one of the embodiments 1 to 20, where in the determining the further link information comprises a proof of work, and wherein the first ledger is a blockchain.

Embodiment 23

The method according to one of the embodiments 1 to 20, where in the determining the further link information comprises a proof of work, and wherein the first ledger is a blocktree.

Embodiment 24

The method according to one of the embodiments 1 to 20, where in the determining the further link information comprises a proof of work, and wherein the first ledger is a tangle.

Embodiment 25

The method according to one of the embodiments 1 to 20, where in the determining the further link information comprises a proof of stake, and wherein the first ledger is a blockchain.

Embodiment 26

The method according one of the embodiments 1 to 20, wherein the determining the further link information comprises a proof of stake, and wherein the first ledger is a blocktree.

Embodiment 27

The method according to one of the embodiments 1 to 20, where in the determining the further link information comprises a proof of stake, and wherein the first ledger is a tangle.

Embodiment 28

The method according to one of the embodiments 1 to 20, where in the determining the further link information comprises a proof of elapsed time, and wherein the first ledger is a blockchain.

Embodiment 29

The method according one of the embodiments 1 to 20, wherein the determining the further link information comprises a proof of elapsed time, and wherein the first ledger is a blocktree. Embodiment 30: The method according to one of the embodiments 1 to 20, where in the determining the further link information comprises a proof of elapsed time, and wherein the first ledger is a tangle.

Embodiment 31

The method according to one of the embodiments 21 to 30, wherein the first ledger comprises a sidechain, wherein the sidechain is a blockchain, a blocktree and/or a tangle.

Embodiment 32

The method according to one of the preceding embodiments, wherein the first ledger is only accessible from within a trusted network.

Embodiment 33

The method according to one of the preceding embodiments, wherein the further data block and/or the further medical dataset comprise a smart contract.

Embodiment 34

The method according to one of the preceding embodiments, furthermore comprising:
transferring cryptocurrency from a first account to a second account by the calculation unit.

Embodiment 35

The method according to embodiment 34, wherein transferring cryptocurrency comprises including a transaction data set into the further medical dataset.

Embodiment 36

The method according to embodiment 34 or 35, wherein the step of transferring cryptocurrency is induced by means of a smart contract.

Embodiment 37

The method according to one of the preceding embodiments, furthermore comprising:
receiving a second ledger with a block verification unit, wherein the second ledger comprises data blocks,
transmitting the further data block with the interface to the block verification unit,
verifying the further link information based on the second ledger with the block verification unit,
in the case of a positive verification, inserting the further data block into the second ledger with the block verification unit.

Embodiment 38

The method according to embodiment 37, wherein each of the data blocks of the second ledger comprises a medical dataset and a link information, wherein the link information comprises a hash of at least one of the second ledger.

Embodiment 39

The method according to embodiment 37 or 38, wherein the second ledger comprises the at least one parent data block of the further data block, and wherein the step of verifying the further link information is based on the at least one parent data block of the further data block.

Embodiment 40

The method according to embodiment 39, wherein in the step of verifying the further link information the hash of the at least one parent data block is compared with the hash contained in the further link information.

Embodiment 41

The method according to one of the embodiments 37 to 40, wherein determining the further link information comprises the execution of a consensus algorithm, wherein verifying the further link information comprises verifying the actual execution of the consensus algorithm.

Embodiment 42

The method according to embodiment 41, furthermore comprising:
receiving a requirement for a hash of the further data block with the block verification unit; wherein verifying the further link information comprises verifying that the hash of the further data block fulfills the requirement.

Embodiment 43

The method according to embodiment 42, wherein the hash of the further data block is a number, wherein the requirement for the hash of the further data block is that hash of the further data block is smaller than a predefined number.

Embodiment 44

A method for verifying a further data block to be inserted in to a second ledger, wherein the second ledger comprises data blocks, comprising the following steps:
receiving the second ledger with an interface,
receiving the further data block with the interface, wherein the further data block comprises a further medical dataset and a further link information,
wherein the further link information comprises a hash of at least one of the data blocks of the second ledger,
verifying the further link information based on the second ledger with the calculation unit
in the case of a positive verification, inserting the further data block into the second ledger with the calculation unit.

Embodiment 45

The method according to embodiment 44, wherein each of the data blocks of the second ledger comprises a medical dataset and a link information, wherein the link information comprises a hash of at least one data block of the second ledger.

Embodiment 46

The method according to embodiment 44 or 45, wherein the second ledger comprises the at least one parent data block of the further data block, and wherein the step of verifying the further link information is based on the at least one parent data block of the further data block.

Embodiment 47

The method according to embodiment 46, wherein in the step of verifying the further link information the hash of the at least one parent data block is compared with the hash contained in the further link information.

Embodiment 48

The method according to one of the embodiments 44 to 47, wherein the further link information is based on a consensus algorithm, wherein verifying the further link information comprises verifying the actual execution of the consensus algorithm.

Embodiment 49

The method according to embodiment 48, furthermore comprising:
receiving a requirement for a hash of the further data block with the interface;
wherein verifying the further link information comprises verifying that the hash of the further data block fulfills the requirement.

Embodiment 50

The method according to embodiment 49, wherein the hash of the further data block is a number, wherein the requirement for the hash of the further data block is that hash of the further data block is smaller than a predefined number.

Embodiment 51

A block creation unit for inserting a further data block into a first ledger, wherein the first ledger comprises data blocks, comprising the following units:
interface, configured for receiving a further medical dataset,
calculation unit, configured for determining the further data block, where in the further data block comprises the further medical dataset and a further link information, wherein the further link information comprises a hash of at least one of the data blocks of the first ledger, furthermore configured for inserting the further data block into the first ledger.

Embodiment 52

The block creation unit according to embodiment 51, further more configured for executing a method according to one of the embodiments 2 to 32.

Embodiment 53

A medical apparatus, comprising a block creation unit according to embodiment 51 or 52.

Embodiment 54

A computer program product comprising program elements which induce a block creation unit to carry out the steps of the method for inserting a further data block into a first ledger according to one of the embodiments 1 to 32, when the program elements are loaded into a memory unit of the block creation unit.

Embodiment 55

A computer-readable medium on which program elements are stored that can be read and executed by a block creation unit, in order to perform steps of the method for inserting a further data block into a first ledger according to one of the embodiments 1 to 32, when the program elements are executed by the block creation unit.

Embodiment 56

A block verification unit for verifying a further data block to be inserted into a second ledger, wherein the second ledger comprises data blocks, comprising the following units:
interface, configured for receiving the second ledger,
furthermore configured for receiving the further data block, wherein the further data block comprises a further medical dataset and a further link information,
wherein the further link information comprises a hash of at least one of the data blocks of the second ledger,
calculation unit, configured for verifying the further link information based on the second ledger,

Embodiment 57

The block verification unit according to embodiment 56, furthermore configured for executing a method according to one of the embodiments 45 to 50.

Embodiment 58

A computer program product comprising program elements which induce a block verification unit to carry out the steps of the method for verifying a further data block to be inserted into a second ledger according to one of the embodiments 44 to 50, when the program elements are loaded into a memory unit of the block verification unit.

Embodiment 59

A computer-readable medium on which program elements are stored that can be read and executed by a block verification unit, in order to perform steps of the method for verifying a further data block to be inserted into a second ledger according to one of the embodiments 44 to 50, when the program elements are executed by the block verification unit.

Embodiment 60

A ledger synchronization system for inserting a further data block into a first ledger and into a second ledger, comprising a block creation unit according to embodiment 51 or 52, and comprising a block verification unit according to embodiment 56 or 57.

Embodiment 61

The ledger synchronization system according to embodiment 60, furthermore configured for executing a method according to one of the embodiments 37 to 43. Embodiment 62: A computer program product comprising program elements which induce a ledger synchronization system to carry out the steps of the method for inserting a further data block into a first ledger according to one of the embodiments 37 to 43, when the program elements are loaded into a memory unit of the ledger synchronization system.

Embodiment 63

A computer-readable medium on which program elements are stored that can be read and executed by a ledger synchronization system, in order to perform steps of the method for inserting a further data block into a first ledger according to one of the embodiments 37 to 43, when the program elements are executed by the ledger synchronization system.

Embodiment 64

A method according to one of the embodiments 1 to 43, wherein the further medical dataset is a log of an access of an entity to a medical data record,
and wherein the further medical dataset comprises an identifier of the medical data record and an identifier of the entity accessing the medical data record.

furthermore configured for, in the case of a positive verification, inserting the further data block into the second ledger.

Embodiment 65

A method according to embodiment 64, wherein the identifier of the medical data record is a hash value of the medical data record.

Embodiment 66

A method according to embodiment 64 or 65, wherein the further medical dataset furthermore comprises a timestamp corresponding to the time of the access of the entity to the medical data record.

Embodiment 67

A method according to one of the embodiments 64 to 66, wherein the identifier of the entity is based on a private key assigned to the entity.

Embodiment 68

A method according to embodiment 67, wherein the identifier of the entity comprises a signature signed with the private key assigned to the entity.

Embodiment 69

A method according to embodiment 68, wherein the signature is based on the medical data record, in particular on a hash value of the medical data record.

Embodiment 70

A method according to embodiment 68 or 69, wherein the medical dataset furthermore comprises a timestamp corresponding to the time of the access of the entity to the medical data record, and wherein the signature is based on the timestamp.

Embodiment 71

A method according to one of the embodiments 64 to 70, wherein the step of receiving the further medical dataset comprises the following steps:
  receiving an access request directed at the medical data record with the interface from the entity, and
  determining the further medical dataset based on the access request and based on the medical data record with the calculation unit.

Embodiment 72

A method according to embodiment 71, furthermore comprising the following step:
  performing a check of the authorization of the entity to access the medical data record,
  in the case of a positive check, granting access to the entity.

Embodiment 73

A method according to embodiment 72, furthermore comprising the following step:
  in the case of a negative check, denying access to the entity, wherein the medical dataset comprises a denial record.

Embodiment 74

The method according to one of the embodiments 44 to 50, wherein the further data block was determined by a method according to one of the embodiments 64 to 73.

Embodiment 75

The block creation unit according to embodiment 51 or 52, furthermore configured for executing a method according to one of the embodiments 64 to 73.

Embodiment 76

A medical apparatus comprising a block creation unit according to embodiment 75.

Embodiment 77

A computer program product comprising program elements which induce a block creation unit to carry out the steps of the method for inserting a further data block into a first ledger according to one of the embodiments 64 to 73, when the program elements are loaded into a memory unit of the block creation unit.

Embodiment 78

A computer-readable medium on which program elements are stored that can be read and executed by a block creation unit, in order to perform steps of the method for inserting a further data block into a first ledger according to one of the embodiments 64 to 73, when the program elements are executed by the block creation unit.

Embodiment 79

The block verification unit according to embodiment 56, furthermore configured for executing a method according to the embodiment 74.

Embodiment 80

A computer program product comprising program elements which induce a block verification unit to carry out the steps of the method for verifying a further data block to be inserted into a second ledger according to embodiment 74, when the program elements are loaded into a memory unit of the block verification unit.

Embodiment 81

A computer-readable medium on which program elements are stored that can be read and executed by a block verification unit, in order to perform steps of the method for verifying a further data block to be inserted into a second ledger according to embodiment 74, when the program elements are executed by the block verification unit.

Embodiment 82

A ledger synchronization system for inserting a further data block into a first ledger and into a second ledger, comprising a block creation unit according to embodiment 75 or 76, and comprising a block verification unit according to embodiment 79.

Embodiment 83

The method according to one of the embodiments 1 to 43, where in the further medical dataset is a log of an access of an entity to a medical apparatus,
wherein the further medical dataset comprises an identifier of the medical apparatus and an identifier of the entity accessing the medical apparatus.

Embodiment 84

A method according to embodiment 83, wherein the identifier of the medical apparatus is based on a model number of the medical apparatus and/or on a serial number of the medical apparatus.

Embodiment 85

A method according to one of the embodiments 83 or 84, wherein the further medical dataset furthermore comprises a timestamp corresponding to the time of the access of the entity to the medical apparatus.

Embodiment 86

A method according to one of the embodiments 83 to 85, wherein the identifier of the entity is based on a private key assigned to the entity. Embodiment 87: A method according to embodiment 86, wherein the identifier of the entity comprises a signature signed with the private key assigned to the entity.

Embodiment 88

A method according to embodiment 87, wherein the signature is based on the identifier of the medical apparatus.

Embodiment 89

A method according to embodiment 87 or 88, wherein the further medical dataset furthermore comprises a timestamp corresponding to the time of the access of the entity to the medical apparatus and/or corresponding to the time of the egress of the entity from the medical apparatus, and wherein the signature is based on the timestamp.

Embodiment 90

A method according to embodiments 83 to 89, wherein the access to the medical apparatus is a remote access.

Embodiment 91

A method according to embodiment 90, wherein the medical dataset comprises the time of access of the entity to the medical apparatus, wherein the time of access corresponds to the time establishing the remote access to the medical apparatus.

Embodiment 92

A method according to embodiment 90 or 91, wherein the medical dataset comprises the time of egress of the entity from the medical apparatus, wherein the time of egress corresponds to the time terminating the remote access to the medical apparatus.

Embodiment 93

A method according to one of the embodiment 90 to 92, further more comprising the following step:
sending a notification message to the owner of the medical apparatus with the interface, wherein the notification message is based on the identifier of the medical apparatus and the identifier of the person accessing the medical apparatus.

Embodiment 94

A method according to embodiment 93, wherein sending the notification message is induced by means of a smart contract.

Embodiment 95

A method according to embodiments 83 to 94, wherein the access of the entity to the medical apparatus comprises a modification of the medical apparatus, and wherein the medical dataset comprises a record of the modification.

Embodiment 96

A method according to embodiment 95, wherein the modification comprises the installation of a hardware component and/or a software component within the medical apparatus, and wherein the further medical dataset comprises an identifier of the hardware component and/or software component.

Embodiment 97

A method according to embodiment 95 or 96, wherein the modification comprises the removal of a hardware component and/or a software component within the medical apparatus, and wherein the medical dataset comprises an identifier of the hardware component and/or software component.

Embodiment 98

A method according to one of the embodiments 95 to 97, wherein the modification comprises an exchange of a first hardware component with a second hardware component and wherein the medical dataset comprises an identifier of the first hardware component and an identifier of the second hard ware component, and/or wherein the modification comprises an exchange of a first software component with a second software component and wherein the medical dataset comprises an identifier of the first software component and an identifier of the second software component.

Embodiment 99

A method according to one of the embodiments 96 to 98, wherein the software component is security update for the medical apparatus.

Embodiment 100

A method according to one of the embodiments 96 to 99, where in the identifier of the software component comprises a software version number.

Embodiment 101

A method according to one of the embodiments 96 to 100, wherein the identifier of the hardware component comprises a model number and/or a serial number of the hardware component.

Embodiment 102

A method according to one of the embodiments 96 to 101, wherein the identifier of the hardware component is stored related to the hardware component.

Embodiment 103

A method according to embodiment 102, wherein the hardware component comprises an RFID-Chip, and wherein the identifier of the hardware component is stored on the RFID-Chip.

Embodiment 104

A method according to embodiment 102 or 103, wherein the hardware component comprises a one-dimensional or two-dimensional optical code, and wherein the identifier of the hardware component is stored in the one-dimensional or two-dimensional optical code.

Embodiment 105

A method according to embodiment 104, wherein the optical code is a barcode.

Embodiment 106

A method according to embodiment 104, wherein the optical code is a QR-Code or an Aztec-Code.

Embodiment 107

A method according to embodiment 95, wherein the modification is the use of a consumable material within the medical apparatus and/or the refill of the consumable material at the medical apparatus.

Embodiment 108

A method according to embodiment 107, wherein the further medical dataset does not comprise the identifier of the entity accessing the medical apparatus.

Embodiment 109

The method according to embodiment 107 or 108, wherein the further medical dataset comprises the amount of consumable material used during a medical procedure with the medical apparatus, and/or wherein the further medical dataset comprises the amount of consumable material refilled at the medical apparatus.

Embodiment 110

A method according to one of the embodiments 83 to 106, wherein the step of receiving the further medical dataset comprises:
receiving the identifier of the medical apparatus with the interface, receiving the identifier of the person accessing the medical apparatus with the interface,
determining the further medical dataset based on the identifier of the medical apparatus and based on the identifier of the person accessing the medical apparatus.

Embodiment 111

A method according to the embodiment 110, wherein the entity performs a modification of the medical apparatus, wherein a record of the modification is created, and wherein the step of receiving the further medical dataset comprises:
receiving the record of the modification with the interface;
wherein the step of determining the further medical dataset is based on the record of the modification.

Embodiment 112

A method according to one of the embodiments 83 to 111, wherein the first ledger documents the number of accesses of the entity to the medical apparatus for implementing a pay-per-use model.

Embodiment 113

A method according to one of the embodiments 83 to 112, wherein the first ledger documents the actions the entity executes with the medical apparatus for implementing the pay-per-use model.

Embodiment 114

A method according to embodiment 112 or 113, furthermore comprising the following step:
performing a check whether a further access of the entity to the medical apparatus and/or a further action of the entity executed with the medical apparatus is covered by the pay-per-use-model,
in the case of a positive check, granting access to the medical apparatus to the entity accessing the medical apparatus with the calculation unit.

Embodiment 115

A method according to one of the embodiments 83 to 114, furthermore comprising the following step:
granting access to the medical apparatus to the entity accessing the medical apparatus with the calculation unit.

Embodiment 116

A method according to one of the embodiments 83 to 115, furthermore comprising:
transferring cryptocurrency from a first account to a second account by the calculation unit, wherein the first account is an account of an owner of the medical apparatus, and wherein the second account is an account of the entity accessing the medical apparatus.

Embodiment 117

The method according to one of the embodiments 44 to 50, wherein the further data block was determined by a method according to one of the embodiments 83 to 116.

Embodiment 118

The block creation unit according to embodiment 51 or 52, furthermore configured for executing a method according to one of the embodiments 83 to 116.

Embodiment 119

A medical apparatus comprising a block creation unit according to embodiment 118.

Embodiment 120

A computer program product comprising program elements which induce a block creation unit to carry out the steps of the method for inserting a further data block into a first ledger according to one of the embodiments 83 to 116, when the program elements are loaded into a memory unit of the block creation unit.

Embodiment 121

A computer-readable medium on which program elements are stored that can be read and executed by a block creation unit, in order to perform steps of the method for inserting a further data block into a first ledger according to one of the embodiments 83 to 116, when the program elements are executed by the block creation unit.

Embodiment 122

The block verification unit according to embodiment 56, furthermore configured for executing a method according to the embodiment 117.

Embodiment 123

A computer program product comprising program elements which induce a block verification unit to carry out the steps of the method for verifying a further data block to be inserted into a second ledger according to embodiment 117, when the program elements are loaded into a memory unit of the block verification unit.

Embodiment 124

A computer-readable medium on which program elements are stored that can be read and executed by a block verification unit, in order to perform steps of the method for verifying a further data block to be inserted into a second ledger according to embodiment 117, when the program elements are executed by the block verification unit.
Embodiment 125: A ledger synchronization system for inserting a further data block into a first ledger and into a second ledger, comprising a block creation unit according to embodiment 118 or 119, and comprising a block verification unit according to embodiment 122.

Embodiment 126

A method according to one of the embodiments 1 to 43, wherein the further medical dataset is a log of the transfer of a medical data record from a first entity to a second entity, wherein the further medical dataset comprises an identifier of the medical data record and an identifier of the first entity and the second entity.

Embodiment 127

A method according to embodiment 126, wherein the identifier of the medical data record is a hash value of the medical data record.

Embodiment 128

A method according to embodiment 126 or 127, wherein the further medical dataset furthermore comprises a timestamp corresponding to the time of the transfer of the medical data record.

Embodiment 129

A method according to one of the embodiments 126 to 128, wherein the identifier of the first entity is based on a private key assigned to the first entity, and/or wherein the identifier of the second entity is based on a private key assigned to the second entity.

Embodiment 130

A method according to embodiment 129, wherein the identifier of the first entity comprises a first signature signed with the private key assigned to the first entity, and or wherein the identifier of the second entity comprises a second signature signed with the private key assigned to the second entity.

Embodiment 131

A method according to embodiment 130, wherein the first signature and/or the second signature are based on the medical data record, in particular on a hash value of the medical data record.

Embodiment 132

A method according to embodiment 130 or 131, wherein the log dataset furthermore comprises a timestamp corresponding to the time of the transfer of the medical data record, and wherein the first signature and/or the second signature are based on the timestamp.

Embodiment 133

A method according to one of the embodiments 126 to 132, wherein the medical data record is a medical data record of a patient, and wherein the medical dataset comprises consent information issued by the patient.

Embodiment 134

A method according to one of the embodiments 126 to 133, wherein the step of receiving the further medical dataset comprises the following steps:
  receiving a transfer request from the second entity related to the medical data record by the interface,
  determining the further medical dataset based on the transfer request and based on the medical data record with the calculation unit.

Embodiment 135

A method according to embodiment 134, furthermore comprising: —providing the medical data record to the second entity with the interface.

Embodiment 136

A method according to embodiment 135, furthermore comprising:
  performing a check of the authorization of the second entity to access the medical data record with the calculation unit;
  wherein the step of providing the medical data record is executed only if the result of the check is positive.

Embodiment 137

The method according to one of the embodiments 126 to 136, furthermore comprising the following steps:
  determining a modified medical data record based on the medical data record with the calculation unit,
  wherein the modified medical data record comprises the identifier of the second entity,
  providing the modified medical data record with the interface.

Embodiment 138

The method according to embodiment 137, wherein the medical data record comprises a medical image, wherein the modified medical data record comprises the medical image equipped with a watermark, and wherein the watermark comprises the identifier of the second entity.

Embodiment 139

The method according to embodiment 138, wherein the medical image comprises a foreground region and a background region, and wherein the watermark is located only in the background region.

Embodiment 140

The method according to one of the embodiments 44 to 50, wherein the further data block was determined by a method according to one of the embodiments 126 to 139.

Embodiment 141

The block creation unit according to embodiment 51 or 52, furthermore configured for executing a method according to one of the embodiments 126 to 139.

Embodiment 142

A medical apparatus comprising a block creation unit according to embodiment 141.

Embodiment 143

A computer program product comprising program elements which induce a block creation unit to carry out the steps of the method for inserting a further data block into a first ledger according to one of the embodiments 126 to 139, when the program elements are loaded into a memory unit of the block creation unit.

Embodiment 144

A computer-readable medium on which program elements are stored that can be read and executed by a block creation unit, in order to perform steps of the method for inserting a further data block into a first ledger according to one of the embodiments 126 to 139, when the program elements are executed by the block creation unit.

Embodiment 145

The block verification unit according to embodiment 56, furthermore configured for executing a method according to the embodiment 140.

Embodiment 146

A computer program product comprising program elements which induce a block verification unit to carry out the steps of the method for verifying a further data block to be inserted into a second ledger according to embodiment 140, when the program elements are loaded into a memory unit of the block verification unit.

Embodiment 147

A computer-readable medium on which program elements are stored that can be read and executed by a block verification unit, in order to perform steps of the method for verifying a further data block to be inserted into a second ledger according to embodiment 140, when the program elements are executed by the block verification unit.

Embodiment 148

A ledger synchronization system for inserting a further data block into a first ledger and into a second ledger, comprising a block creation unit according to embodiment 141 or 142, and comprising a block verification unit according to embodiment 145. Embodiment 149: A method according to one of the embodiments 1 to 43, wherein the further medical dataset corresponds to the admission process of a medical apparatus.

Embodiment 150

A method according to embodiment 149, wherein the medical apparatus comprises a trained artificial intelligence algorithm, and wherein the further medical dataset is based on a training dataset used for the training of the artificial intelligence algorithm.

Embodiment 151

A method according to embodiment 150, wherein the step of receiving a further medical dataset comprises:
 receiving the training dataset with the interface,
 determining a first parameter of the artificial intelligence algorithm with the calculation unit,
 performing a training step of the artificial intelligence algorithm based on the training dataset with the calculation unit,
 determining a second parameter of the artificial intelligence algorithm with the calculation unit,
 determining the further medical dataset based on the training dataset and based on the first and the second parameter with the calculation unit.

Embodiment 152

A method according to embodiment 151, wherein the artificial intelligence algorithm comprises an artificial neural network, and wherein the first parameter comprises a weight of an edge of the artificial neural network before performing the training step, and wherein the second parameter comprises the weight of the edge after performing the training step.

Embodiment 153

A method according to embodiment 152, wherein the first parameter comprises the weights of all edges of the artificial neural network before performing the training step, and wherein the second parameter comprises the weights of all edges of the artificial neural network after per forming the training step.

Embodiment 154

A method according to one of the embodiments 150 to 153, wherein the training dataset comprises a training image.

Embodiment 155

A method according to the embodiment 154, wherein the training dataset comprises a label associated with the training image.

Embodiment 156

A method according to embodiment 149, wherein the medical dataset comprises an identifier of a person being subject of a medical study.

Embodiment 157

A method according to embodiment 156, wherein the identifier of a person is a physical parameter of the person uniquely identifying the person.

Embodiment 158

A method according to embodiment 157, wherein the identifier of the person corresponds to a fingerprint of the person, to a DNA sequence of the person or to a biometrical parameter of the person.

Embodiment 159

A method according to one of the embodiments 156 to 158, wherein the medical dataset comprises a first patient parameter corresponding to the person before the medical study, and wherein the medical dataset furthermore comprises a second patient parameter corresponding to the person after the medical study.

Embodiment 160

A method according to one of the embodiments 155 to 159, wherein the step of receiving a further medical dataset comprises:
 receiving the identifier of the person being subject of the medical study with the interface,
 determining the further medical dataset based on the identifier of the per son being subject of the medical study with the calculation unit. Embodiment 161: A method according to embodiment 159, wherein the step of receiving a further medical dataset comprises:
receiving the identifier of the person being subject of the medical study with the interface,
receiving the first patient parameter corresponding to the person before the medical study with the interface,
receiving the second patient parameter corresponding to the person after the medical study with the interface,
determining the further medical dataset based on the identifier of the person being subject of the medical study and based on the first patient parameter and the second patient parameter with the calculation unit.

Embodiment 162

The method according to embodiment 149, wherein the further medical dataset corresponds to the admission process of a medical apparatus by corresponding to a calibration of the medical apparatus.

Embodiment 163

The method according to embodiment 162, wherein the further medical dataset comprise an identifier of the medical apparatus and a timestamp, wherein the timestamp corresponds to the time of calibration of the medical apparatus.

Embodiment 164

The method according to embodiment 163, wherein the step of receiving the further medical dataset comprises the following steps:
receiving the identifier of the medical apparatus with the interface,
determining the further medical dataset based on the identifier of the medical apparatus with the calculation unit.

Embodiment 165

The method according to one of the embodiments 162 to 164, wherein the further medical dataset comprises an identifier of an entity performing the calibration of the medical apparatus.

Embodiment 166

The method according to the embodiment 165, wherein the step of receiving the further medical dataset comprises the following steps:
receiving the identifier of the entity performing the calibration of the medical apparatus,
determining the further medical dataset based on the identifier of the entity performing the calibration of the medical apparatus, in particular furthermore based on the identifier of the medical apparatus with the calculation unit.

Embodiment 167

The method according to one of the embodiments 162 to 166, wherein the further medical dataset comprises calibration information based on the calibration of the medical apparatus.

Embodiment 168

The method according to embodiment 167, wherein the step of receiving the further medical dataset comprises the following steps:
receiving the calibration information with the interface,
determining the further medical dataset based on the calibration information with the calculation unit, in particular furthermore based on the identifier of the medical apparatus and/or on the identifier of the entity performing the calibration of the medical apparatus.

Embodiment 169

The method according to embodiment 149, wherein the further medical dataset comprises data documenting the product development of the medical apparatus.

Embodiment 170

The method according to embodiment 169, wherein the further medical dataset comprises data describing a certain version of software contained in the medical apparatus.

Embodiment 171

The method according to embodiment 170, wherein the data de scribing a certain version of the software describes a commit to a source code repository and/or a build within a continuous integration and/or a continuous delivery system.

Embodiment 172

The method according to embodiment 171, wherein the data de scribing the certain version of the software comprises a hash of the commit to the source code repository and/or a hash of the build within the continuous integration and/or the continuous delivery system.

Embodiment 173

The method according to one of the embodiments 169 to 172, wherein the further medical dataset comprises at least one signature signing the data documenting the product development of the medical apparatus.

Embodiment 174

The method according to one of the embodiments 169 to 173, wherein the further medical dataset comprises a smart contract, wherein the smart contract regulates the release of the medical apparatus, in particular the release of a certain version of software contained in the medical apparatus.

Embodiment 175

The method according to embodiment 174, wherein the certain version of software is released if the medical dataset comprises a predefined set of signatures signing data describing the certain version of software.

Embodiment 176

The method according to one of the embodiments 169 to 173, wherein the further medical dataset comprises a smart contract, wherein the smart contract regulates the access to the data documenting the product development of the medical apparatus.

Embodiment 177

The method according to embodiment 176, wherein the smart contract grants access to the data documenting the product development of the medical apparatus for a regulatory authority.

Embodiment 178

A method for determining identical persons using a first ledger, wherein a further data block was included into the first ledger according to one of the embodiments 156 to 158, comprising the following steps:
selecting a first medical dataset contained in the first ledger with a calculation unit,
wherein the first medical dataset comprises an identifier of a first person,
selecting a second medical dataset contained in the first ledger with the calculation unit,
wherein the second medical dataset is different from the first medical dataset,
and wherein the second medical dataset comprises an identifier of a second person,
determining whether the first person and the second person are identical based on the identifier of the first person and the identifier of the second person with the calculation unit.

Embodiment 179

The method according to embodiment 178, furthermore comprising:
in the case of the first person and the second person being identical, providing an alert message with an interface.

Embodiment 180

The method according to embodiment 178 or 179, wherein the first person is subject of a first medical study, wherein the second person is subject of the second medical study, and wherein the first study is identical with the second study.

Embodiment 181

The method according to one of the embodiments 178 to 180, wherein the step of selecting the second medical dataset and the step of determining are applied multiple times. Embodiment 182: A calculation unit for determining identical persons using a first ledger, wherein a further data block was included into the first ledger according to one of the embodiments 156 to 158,
configured for selecting a first medical dataset contained in the first ledger, wherein the first medical dataset comprises an identifier of a first person,
furthermore configured for selecting a second medical dataset contained in the first ledger, wherein the second medical dataset is different from the first medical dataset, and wherein the second medical dataset comprises an identifier of a second person,
furthermore configured for determining whether the first person and the second person are identical based on the identifier of the first person and the identifier of the second person.

Embodiment 183

The calculation unit according to embodiment 182, furthermore configured for executing a method according to one of the embodiments 179 to 181.

Embodiment 184

A computer program product comprising program elements which induce a calculation unit to carry out the steps of the method for determining identical persons using a first ledger according to one of the embodiments 178 to 181, when the program elements are loaded into the calculation unit.

Embodiment 185

A computer-readable medium on which program elements are stored that can be read and executed by a calculation unit, in order to perform steps of the method for determining identical persons using a first ledger according to one of the embodiments 178 to 181, when the program elements are executed by the calculation unit.

Embodiment 186

The method according to one of the embodiments 44 to 50, wherein the further data block was determined by a method according to one of the embodiments 149 to 177.

Embodiment 187

The block creation unit according to embodiment 51 or 52, furthermore configured for executing a method according to one of the embodiments 149 to 177.

Embodiment 188

A medical apparatus comprising a block creation unit according to embodiment 187.

Embodiment 189

A computer program product comprising program elements which induce a block creation unit to carry out the steps of the method for inserting a further data block into a first ledger according to one of the embodiments 149 to (D25), when the program elements are loaded into a memory unit of the block creation unit.

Embodiment 190

A computer-readable medium on which program elements are stored that can be read and executed by a block creation unit, in order to perform steps of the method for inserting a further data block into a first ledger according to one of the embodiments 149 to (D25), when the program elements are executed by the block creation unit.

Embodiment 191

The block verification unit according to embodiment 56, furthermore configured for executing a method according to the embodiment 186.

Embodiment 192

A computer program product comprising program elements which induce a block verification unit to carry out the steps of the method for verifying a further data block to be inserted into a second ledger according to embodiment 186, when the program elements are loaded into a memory unit of the block verification unit.

Embodiment 193

A computer-readable medium on which program elements are stored that can be read and executed by a block verification unit, in order to perform steps of the method for verifying a further data block to be inserted into a second ledger according to embodiment 186, when the program elements are executed by the block verification unit.

Embodiment 194

A ledger synchronization system for inserting a further data block into a first ledger and into a second ledger, comprising a block creation unit according to embodiment 187 or 188, and comprising a block verification unit according to embodiment 191.

Embodiment 195

A method according to one of the embodiments 1 to 43, wherein the further medical dataset is related to an educational action of a medical professional, and wherein the further medical dataset comprises an identifier of the medical professional and an identifier of the educational action.

Embodiment 196

The method according to embodiment 195, wherein the educational action is supervised and/or rated by an education entity,
    wherein the medical dataset comprises a signature of the identifier of the educational action and the identifier of the medical professional,
    and wherein the signature is signed by the education entity.

Embodiment 197

The method according to one of the embodiments 195 or 196, wherein the step of receiving the medical dataset comprises:
    providing a medical data record to the medical professional by the interface,
wherein a first medical information is assigned to the medical data record,
    receiving a second medical information from the medical professional by the interface,
    determining a comparison value based on the first medical information and on the second medical information by the calculation unit;
wherein the medical dataset is based on the comparison value.

Embodiment 198

The method according to the embodiment 197, wherein the first medical information is a diagnosis information regarding the medical data record determined by another entity, and wherein the second medical information is a diagnosis information regarding the medical data record determined by the medical professional.

Embodiment 199

The method according to embodiment 198, wherein the medical data record and the first medical information are synthetically generated data.

Embodiment 200

The method according to embodiment 198, wherein the medical data record corresponds to a patient, and wherein the first medical information was created by an experienced medical professional. Embodiment 201: The method according to one of the embodiments 198 to 200, wherein the medical data record comprises a medical image and/or a medical laboratory report.

Embodiment 202

A method according to one of the embodiments 195 to 201, furthermore comprising: —transferring first cryptocurrency from a first account to a second account by the calculation unit, wherein the second account is an account of the medical professional.

Embodiment 203

A method according to one of the embodiments 195 to 202, furthermore comprising: —transferring second cryptocurrency from a first account to a second account by the calculation unit, wherein the first account is an account of the medical professional.

Embodiment 204

A method for using a first ledger after inserting a further data block according to one of the embodiments 198 to 203 for verifying the experience of a medical professional, comprising the steps of:
    receiving the first ledger with an interface,
receiving an identifier of the medical professional with the interface,
    receiving an identifier of an educational action with the interface,
    determining the relevant data blocks of the first ledger with a calculation unit,
wherein a relevant data block is a data block of the first ledger comprising a relevant medical dataset,
and wherein a relevant medical dataset is a medical dataset comprising the identifier of the medical professional and the identifier of the educational action, determining an education parameter based on the relevant data blocks.

Embodiment 205

The method according to embodiment 204, wherein the education parameter is the number of relevant data blocks.

Embodiment 206

The method according to embodiment 204 or 205, furthermore comprising:
receiving a minimal educational requirement with the interface; wherein the education parameter is furthermore based on the minimal educational requirement.

Embodiment 207

The method according to embodiment 206, wherein the minimal educational requirement is a minimal number of educational actions to be per formed, and wherein the education parameter is based on a comparison of the number of relevant data blocks and the minimal number of educational requirements.

Embodiment 208

The method according one of the embodiments 204 to 207, furthermore comprising the step of:
receiving a threshold comparison value with the interface; wherein a relevant medical dataset is a medical dataset comprising a comparison value above or below the threshold value.

Embodiment 209

An experience verification unit for verifying the experience of a medical professional using a first ledger after inserting a further data block according to one of the embodiments 198 to 203, comprising the following units:
interface, configured for receiving the first ledger, furthermore configured for receiving an identifier of the medical professional,
furthermore configured for receiving an identifier of an educational action,
calculation unit, configured for determining the relevant data blocks of the first ledger, wherein a relevant data block is a data block of the first ledger comprising a relevant medical dataset, and wherein a relevant medical dataset is a medical dataset comprising the identifier of the medical professional and the identifier of the educational action,
furthermore configured for determining an education parameter based on the relevant data blocks.

Embodiment 210

The experience verification unit according to embodiment 209, furthermore configured for executing a method according to one of the embodiments 205 to 208.

Embodiment 211

A computer program product comprising program elements which induce an experience verification unit to carry out the steps of the method for verifying the experience of a medical professional according to one of the embodiments 204 to 208, when the program elements are loaded into a memory unit of the experience verification unit.

Embodiment 212

A computer-readable medium on which program elements are stored that can be read and executed by an experience verification unit, in order to perform steps of the method for verifying the experience of a medical professional according to one of the embodiments 204 to E41, when the program elements are executed by the experience verification unit.

Embodiment 213

The method according to one of the embodiments 44 to 50, wherein the further data block was determined by a method according to one of the embodiments 195 to 203.

Embodiment 214

The block creation unit according to embodiment 51 or 52, furthermore configured for executing a method according to one of the embodiments 195 to 203.

Embodiment 215

A medical apparatus comprising a block creation unit according to embodiment 214.

Embodiment 216

A computer program product comprising program elements which induce a block creation unit to carry out the steps of the method for inserting a further data block into a first ledger according to one of the embodiments 195 to 203, when the program elements are loaded into a memory unit of the block creation unit.

Embodiment 217

A computer-readable medium on which program elements are stored that can be read and executed by a block creation unit, in order to perform steps of the method for inserting a further data block into a first ledger according to one of the embodiments 195 to 203, when the program elements are executed by the block creation unit.

Embodiment 218

The block verification unit according to embodiment 56, furthermore configured for executing a method according to the embodiment 213.

Embodiment 219

A computer program product comprising program elements which induce a block verification unit to carry out the steps of the method for verifying a further data block to be inserted into a second ledger according to embodiment 213, when the program elements are loaded into a memory unit of the block verification unit.

Embodiment 220

A computer-readable medium on which program elements are stored that can be read and executed by a block verification unit, in order to perform steps of the method for verifying a further data block to be inserted into a second ledger according to embodiment 213, when the program elements are executed by the block verification unit.

Embodiment 221

A ledger synchronization system for inserting a further data block into a first ledger and into a second ledger, comprising a block creation unit according to embodiment 214 or 215, and comprising a block verification unit according to embodiment 218.

FIG. 1 displays a flowchart of an embodiment of the method for inserting a further data block FDB into a first ledger LDG, wherein the first ledger comprises data blocks DB.i, DB.j, DB.k. The method is executed by a block creation unit BCU, in particular by an interface BCU.IF of the block creation unit and by a calculation unit BCU.CU of the block creation unit.

The first step of the displayed embodiment is receiving REC-FDS a further medical dataset FDS with the interface BCU.IF. An optional second step of the displayed embodiment is receiving REC-LDG-1 the first ledger LDG with the interface BCU.IF. Alternatively, the step of receiving REC-LDG-1 the first ledger LDG can be executed before the step of receiving REC-FDS the further medical dataset FDS, or step of receiving REC-LDG-1 the first ledger LDG can be executed in parallel to the step of receiving REC-FDS the further medical dataset FDS. In other words, both steps are independent from each other.

In this embodiment, the first ledger LDG is a blockchain, which means that each of the data blocks DB.i, DB.j, DB.k contained in the first ledger LDG (except a single origin data block) has exactly one parent data block DB.i, DB.j, DB.k, and each of the data blocks DB.i, DB.j, DB.k (except a single last data block) has exactly one direct succeeding data block. An example for a blockchain can be found in FIG. 5, comprising the single origin data block DB.I and the single last data block DB.7.

Each of the data blocks DB.i, DB.j, DB.k contained in the first ledger comprises a link information, which relates the data block DB.i, DB.j, DB.k to its parent data block. In particular, each of the data blocks DB.i, DB.j, DB.k comprises a hash based on its parent data block. In this embodiment, the hash is the result of applying the SHA256 hash function onto data of the parent data block. Furthermore, each of the data blocks DB.i, DB.j, DB.k comprises a medical dataset MDS.j, MDS.k. Alternatively, it is also possible that the blockchain comprises blocks DB.i, DB.j, DB.k comprising no medical dataset MDS.j, MDS.k, but a non-medical dataset.

Furthermore, each of the data blocks DB.i, DB.j, DB.k contained in the first ledger comprises a nonce RN.j, RN.k chosen such that the hash H(DB.i), H(DB.j), H(DB.k) of the data block DB.i, DB.j, DB.k fulfills a certain condition. In the displayed embodiment, the condition is that the hash H(DB.i), H(DB.j), H(DB.k) of the data block DB.i, DB.j, DB.k is smaller than a given threshold.

In this embodiment, the hash H(DB.j) of a data block DB.j is calculated as H(DB.j)=SHA256 (H (MDS.j)+H(DB.i)+RN.j), wherein the SHA256 hash function can be replaced with any other suitable hash function. The operation "+" can be understood as arithmetic addition of numbers or as concatenation of strings (by converting numbers to strings before the concatenation). In particular, the hash H(MDS.j) of the medical data set MDS.j can be the Merkle root of the medical data set MDS.j. Alternatively, the hash H(DB.j) of a data block DB.j can also be based on other data items contained in the data block. The next optional step of the displayed embodiment is selecting SEL-PDB a parent data block from the data blocks of the first ledger with the calculation unit BCU.CU. In the displayed embodiment, the parent data block is the single data block DB.i, DB.j, DB.k of the first ledger LDG which has no direct successor. For the blockchain displayed in FIG. 5, the parent data block is the data block DB.7. Alternatively, it is possible that there is a fork in the first ledger LDG being a blockchain, which means that there are several data blocks DB.i, DB.j, DB.k of the first ledger LDG without direct successor. In this case, the parent data block is the data block from the set of data blocks DB.i, DB.j, DB.k without direct successor which has the biggest distance from the origin data block.

The next step of the displayed embodiment is determining DET-FDB the further data block FDB with the calculation unit BCU.CU, wherein the further data block FDB comprises the further medical dataset FDS and a further link information, wherein the further link information comprises a hash H(DB.i), H(DB.j), H(DB.k) of at least one of the data blocks DB.i, DB.j, DB.k of the first ledger LDG.

In particular, the step of determining DET-FDB the further data block FDB comprises the execution of a consensus algorithm. In this embodiment, the consensus algorithm is a compute-bound or CPU bound proof of work, in particular the proof of work involves the calculation unit BCU.CU of the block nit BCU. Alternatively, the consensus algorithm may be a memory-bound proof or work (in particular, in order to determine DET-FDB the further data block a certain amount of memory needs to be allocated in the memory unit BCU. MU of the block creation unit), a network-bound proof of work (in particular, in order to determine DET-FDB the further data block, either a lot of network nodes or difficult to access network nodes need to be accessed), a proof of stake, a proof of elapsed time, or a proof of storage, or any other consensus algorithm.

In particular, for a compute-bound proof the time or the number of steps f(n) to determine DET-FDB the further data block in terms of the problem complexity n has a higher asymptotic behavior then the time or the number of calculation steps g(n) to verify VERF the further data block FDB in a block verification unit BVU. In other words, no constant M can be found so that for all n>nO the equation $|g(n)|<M \cdot |f(n)|$ is valid.

An example for a compute-bound proof of work is finding an argument of a hash function so that the result of the hash function fulfills a certain criterion (e.g. is smaller than a given number, or has a given structure). Since hash functions are one-way functions, the only possibility is to try out a lot of arguments by brute force. In particular, the certain criterion can be that the result of the hash function as binary number must comprise n leading zeros (so that n in this case is the problem complexity), which leads to the number of hash functions to calculate is f(n) 2<n> for determining DET-NLI the new link information NLI and g(n)=1 for verifying VERF the link information.

Known kryptological hash functions are "Snefru", "N-Hash", "FFT-Hash", "MD4", "MD5", "SHA" (in particular "SHA-0", "SHA-1", "SHA-256", "SHA-384" and "SHA-512"), "RIPEMD", "HAVAL", "TIGER", "PANAMA", "WHIRLPOOL", "SMA SH", "FORK-256", "SHA-3", "BLAKE", or other hash functions based on the Merkle-Damgard construction or on the Sponge construction.

In the displayed embodiment, the determining DET-FDB the further data block FDB comprises determining a nonce RN.1 of the further data block FDB, so that the hash H(FDB)

of the further data block fulfills a certain condition, in this embodiment so that the hash H (FDB) of the further data block FDB is smaller than a given threshold T. Since the hash function is a one-way function, in order to determine the nonce RN.1 of the further data block FDB, several nonces have to be tested by calculating testwise the hash H (FDB) of the further data block FDB and checking whether the hash H(FDB) of the further data block FDB is below the threshold. The hash H(FDB) of the further data block FDB is defined as the hash H(DB.i), H(DB.j), H(DB.k) of the other data blocks DB.i, DB.j, DB.k.

Alternatively to the compute-bound proof of work, a memory bound proof of work can be used. In particular, for a memory-bound proof the number of values f(n) to store temporarily (in the memory unit BCU.MU of the block creation unit) in order to determine DET-FDB the further data block FDB in terms of the problem complexity n has a higher asymptotic behavior then number of values g(n) to store temporarily (in the memory unit BVU.MU of the block verification unit BVU) in order to verify VERF the further data block FDB. In other words, no constant M can be found so that for all n>nO the equation $|g(n)|<M\cdot|f(n)|$ is valid.

An example for a memory-bound proof of work is finding a cycle of a given length 1 in a random graph with n nodes, where the number n of nodes is the problem complexity. In this example the number of values to store is f(n) n for finding a cycle of length 1 for determining DET-NLI the new link information, and g(n) 1 for verifying a cycle for verifying VERF the new link in formation NLI.

The next step of the displayed embodiment is including INS-FDB-1 the further data block FDB into the first ledger LDG with the calculation unit BCU.CU. In this embodiment, the further data block FDB is included into the first ledger LDG by storing the further data block FDB in a memory unit BCU.MU, wherein the memory unit BCU.MU stores at least some blocks of the first ledger LDG.

In particular, an identifier of the further data block FDB, in particular a hash H(FDB) of the further data block FDB can be stored in an array or list of all data blocks of the first ledger LDG, wherein the array or list is stored related to the data blocks of the first ledger.

A further optional step of the displayed embodiment is providing PROV-FDB the further data block FDB with the interface BCU.IF. In particular, the further data block FDB can be sent to a block verification unit BVU. In particular, the further data block FDB can also be made publically available by uploading the further data block FDB to a Webserver.

Figure 2:
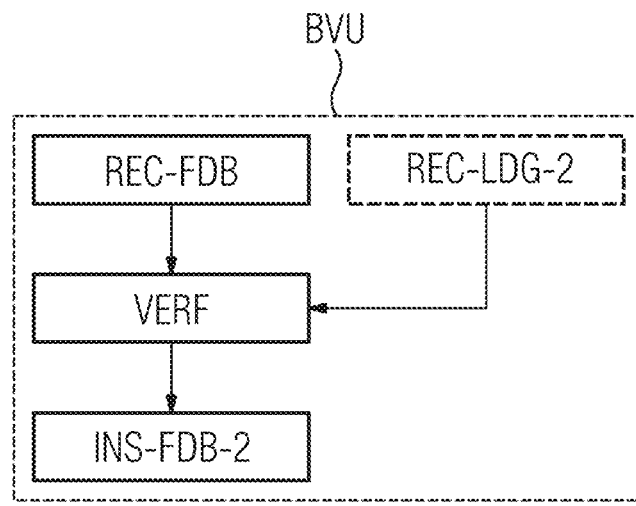
FIG. 2 displays a flowchart of an embodiment of the method for verifying a further data block to be inserted into a second ledger.

FIG. 2 displays a flowchart of an embodiment of the method for verifying a further data block FDB to be inserted into a second ledger, wherein the second ledger comprises data blocks DB.i, DB.j, DB.k. The method is executed by a block verification unit BVU, in particular by an interface BVU. IF of the block verification unit BVU and by a calculation unit BVU.CU of the block verification unit BVU.

The first step of the displayed embodiment is receiving REC-FDB a further data block FDS with the interface BVU. IF, wherein the further data block FDB comprises a further medical dataset FDS and a further link information, wherein the further link information comprises a hash of at least one of the data blocks DB.i, DB.j, DB.k of the second ledger. The second step of the displayed embodiment is receiving REC-LDG-2 the second ledger with the block verification unit BVU, in particular with an interface BVU. IF of the block verification unit BVU.

Alternatively, the step of receiving REC-LDG-2 the second ledger LDG can be executed before the step of receiving REC-FDB the further data block FDB, or the step of receiving REC-LDG-2 the second ledger can be executed in parallel to the step of receiving REC-FDB the further data block FDB. In other words, both steps are independent from each other.

In this embodiment, the second ledger is a blockchain comprising data blocks DB.i, DB.j, DB.k also contained in the first ledger. In particular, the second ledger can comprise all data blocks DB.i, DB.j, DB.k of the first ledger LDG, except the further data block FDB. In particular, the second ledger comprises the parent data block of the further data block FDB.

The next step of the displayed embodiment is verifying VERF the further link information based on the second ledger with the block verification unit BVU, in particular with the calculation unit BVU.CU of the block verification unit BVU. In this embodiment, the further data block FDB comprises a nonce RN.l and a hash value of at least one of the data blocks DB.i, DB.j, DB.k of the second ledger, here the hash value H(DB.k) of the data block DB.k. Furthermore, in order to be a valid block, the hash H(FDB) of the further data block FDB must fulfill a given condition, for example the H(FDB) of the further data block FDB must be below a given threshold. So in this embodiment, in order to verify VERF the further link information, the hash H (FDB) of the further data block FDB has to be calculated as H(FDB)=SHA256 (H (FDS)+H(DB.k)+RN.l), and it has to be verified that H(FDB) is below the threshold.

The last step of the displayed embodiment is, in the case of a positive verification, inserting INS-FDB-2 the further data block FDB into the second ledger with the block verification unit BVU, in particular with the calculation unit BVU.CU of the block verification unit. In this embodiment, the further data block FDB is included into the second ledger by storing the further data block FDB in a memory unit BVU. MU of the block verification unit BVU, wherein the memory unit BCU.MU stores at least some blocks of the second ledger LDG. In particular, an identifier of the further data block FDB, in particular a hash H(FDB) of the further data block FDB can be stored in an array or list of all data blocks of the second ledger, wherein the array or list is stored related to the data blocks of the second ledger.

Figure 3:
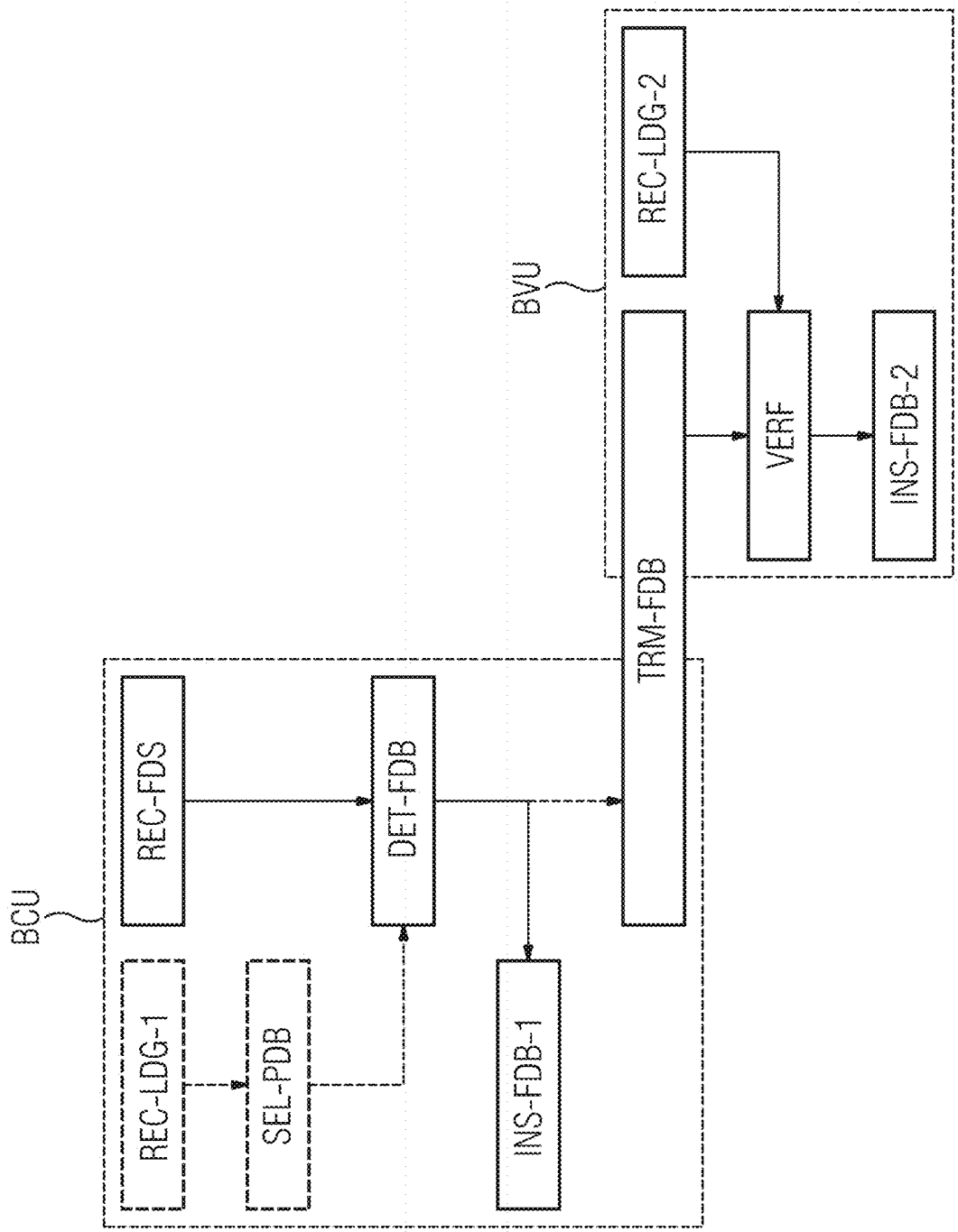
FIG. 3 displays a flowchart of a second embodiment of the method for inserting a further data block into a first ledger.

FIG. 3 displays a second embodiment of the method for inserting a further data block FDB into a first ledger LDG, which is a sequential execution of the first embodiment of the method for inserting a further data block FDB into a first ledger LDG displayed in FIG. 1, and the embodiment of the method for verifying a further data block FDB to be inserted into a second ledger dis played in FIG. 2.

In particular, the displayed embodiment comprises the step of transmitting TRM-FDB the further data block FDB from the block creation unit BCU to the block verification unit BVU, in particular from the interface BCU. IF of the block creation unit BCU to the interface BCU. IF of the block verification unit BVU. This step is equivalent to the execution of the steps of providing PROV-FDB the further data block FDB with the interface BCU. IF of the block creation unit BCU and the step of receiving REC-FDB a further data block FDS with the block verification unit BVU.

Figure 4:
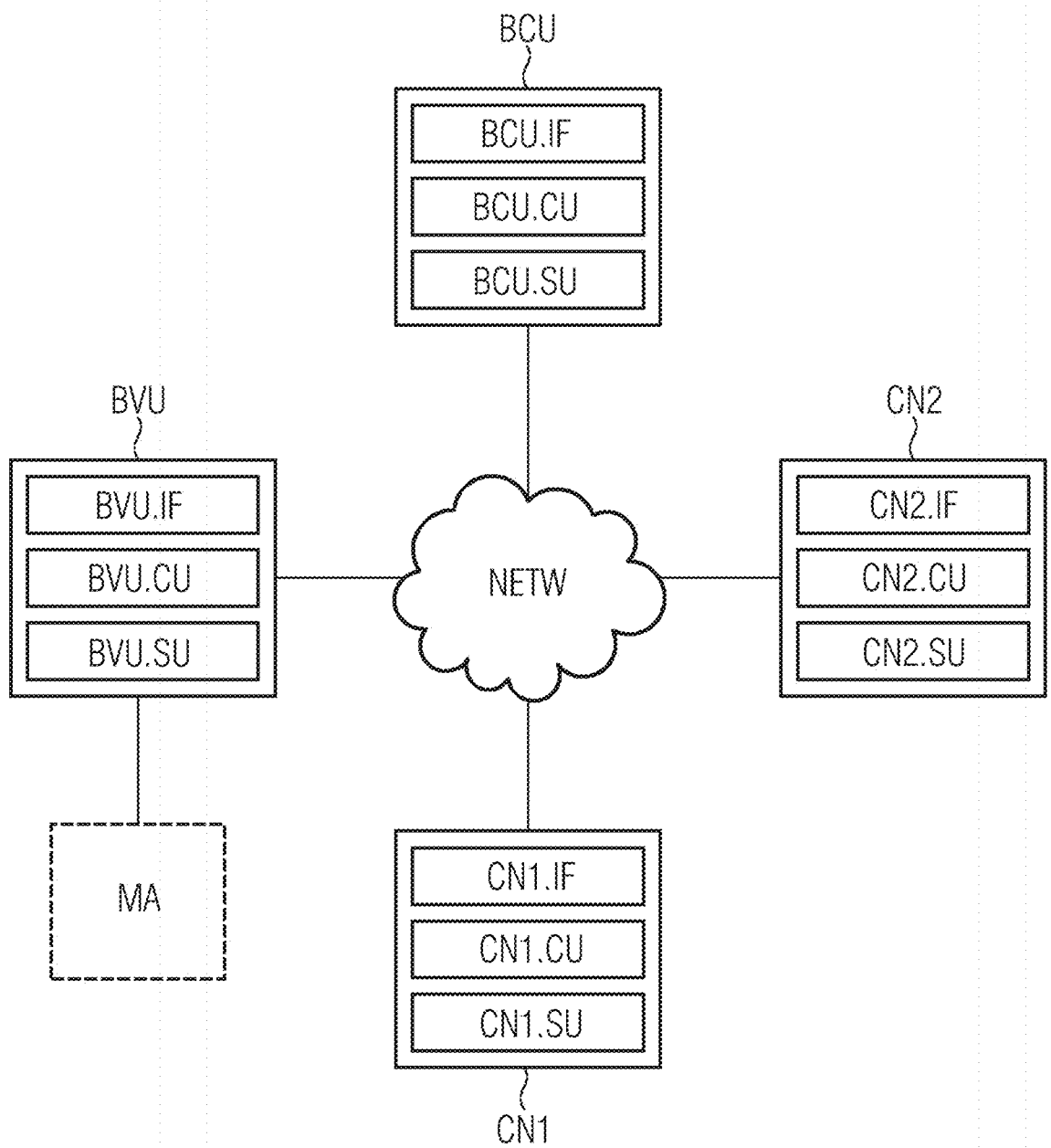
FIG. 4 displays an embodiment of a ledger synchronization system, comprising a block creation unit and a block verification unit.

FIG. 4 displays an embodiment of the block creation unit BCU and an embodiment of the block verification unit BVU. The block creation unit BCU is connected to the block verification unit BVU via a network NETW, furthermore the block creation unit BCU and the block verification unit BVU are connected via the network NETW to a set of computation nodes CN1, CN2.

The block creation unit BCU, the block verification unit BVU or the computation nodes CN1, CN2 may be a (personal) computer, a workstation, a virtual machine running on host hardware, a microcontroller, or an integrated circuit. As an alternative, the block creation unit BCU, the block verification unit BVU or the computation nodes CN1, CN2 can be a real or a virtual group of computers (the technical term for a real group of computers is "cluster", the technical term for a virtual group of computers is "cloud"). Each of the block creation unit BCU, the block verification unit BVU or the computation nodes CN1, CN2 comprise an interface BCU. IF, BVU. IF, CN1.IF, CN2.IF, a calculation unit BCU.CU, BVU.CU, CN1.CU, CN2. CU and a memory unit BCU.MU, BVU. MU, CN1.MU, CN2.MU. An interface BCU.IF, BVU.IF, CN1.IF, CN2. IF can be embodies as a hardware interface or as a software interface (e.g. PCI-Bus, USB or Firewire). In general, a calculation unit BCU.CU, BVU.CU, CN1.CU, CN2.CU can comprise hardware elements and software elements, for example a microprocessor, a field programmable gate array (an acronym is "FPGA") or an application specific integrated circuit (an acronym is "ASIC"). A memory unit BCU.MU, BVU.MU, CN1.MU, CN2.MU can be embodied as non-permanent main memory (e.g. random access memory) or as permanent mass storage (e.g. hard disk, USB stick, SD card, solid state disk).

The network NETW can be realized as a LAN (acronym for "local area network"), in particular a WiFi network, or any other local connection, e.g. via Blue tooth or USB (acronym for "universal serial bus"). The network NETW can also be realized as a WAN (acronym for "wide area network"), in particular the network NETW can be identical with the internet. The network NETW can alter natively also be realized as a VPN (acronym for "virtual private network").

In the displayed embodiment, the block creation unit BCU is connected with a medical apparatus MA. The connection of the block creation unit BCU to the medical apparatus MA is optional. Alternatively, the block creation unit BCU can also be identical with the medical apparatus MA. Alternatively, the medical apparatus MA can also comprise the block creation unit BCU. Alternatively, the medical apparatus can be connected to, identical with or comprising the block verification unit BVU and/or one of the computation nodes CN1, CN2, and communicate with the block creation unit BCU by means of the network NETW.

In the displayed embodiment, there are further computation nodes CN1, CN2 connected to the block verification unit BVU and the block creation unit BCU. The block verification unit BVU, the block creation unit BCU and the further computation nodes CN1, CN2 form a peer-to-peer network. In general, the block verification unit BVU, the block creation unit BCU and the further computation nodes CN1, CN2 can be treated as equivalent, in other means, also the block verification unit BVU and/or one of the computation nodes CN1, CN2 can be a block creation unit BCU for another further data block, and the block creation unit BCU and/or one of the computation nodes CN1, CN2 can be a block verification unit BVU for the another further data block.

In a preferred embodiment the medical apparatus MA is not permanently connected with the block creation unit BCU. In particular, the connection between the medical apparatus MA and the block creation unit BCU can be an in direct connection, in order to isolate the medical apparatus MA from the other units for security reasons. For example, the medical apparatus MA can communicate with the block creation unit by a one-way communication channel, e.g. by displaying one-dimensional or two-dimensional barcodes like QR-Codes, which can be read directly or indirectly with the block creation unit. Alter natively, the connection between the block creation unit BCU and the medical apparatus MA can also be established via the network NETW.

Figure 5:
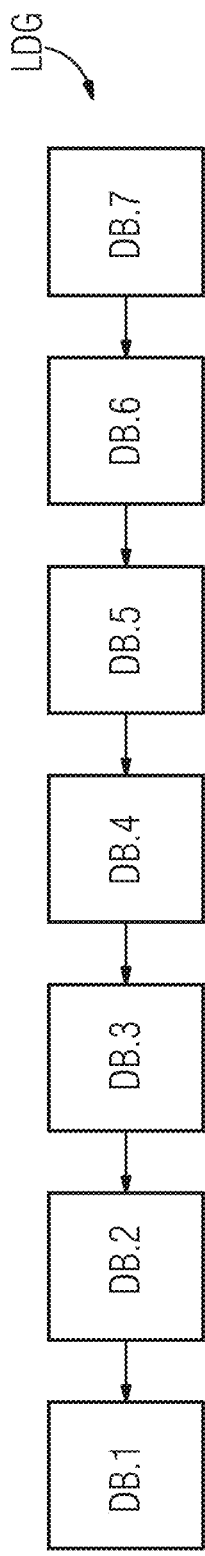
FIG. 5 displays a first embodiment of a ledger, wherein the ledger is a blockchain.
Figure 6:
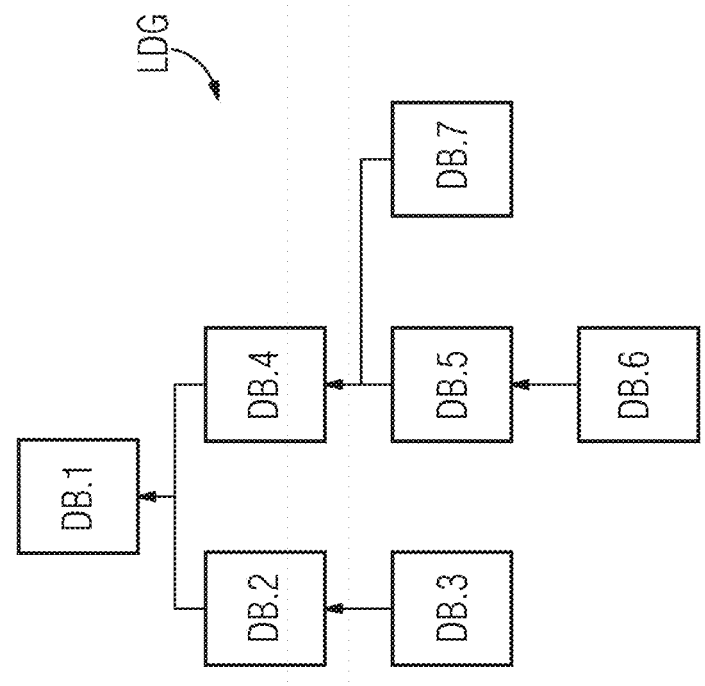
FIG. 6 displays a second embodiment of a ledger, wherein the ledger is a blocktree.
Figure 7:
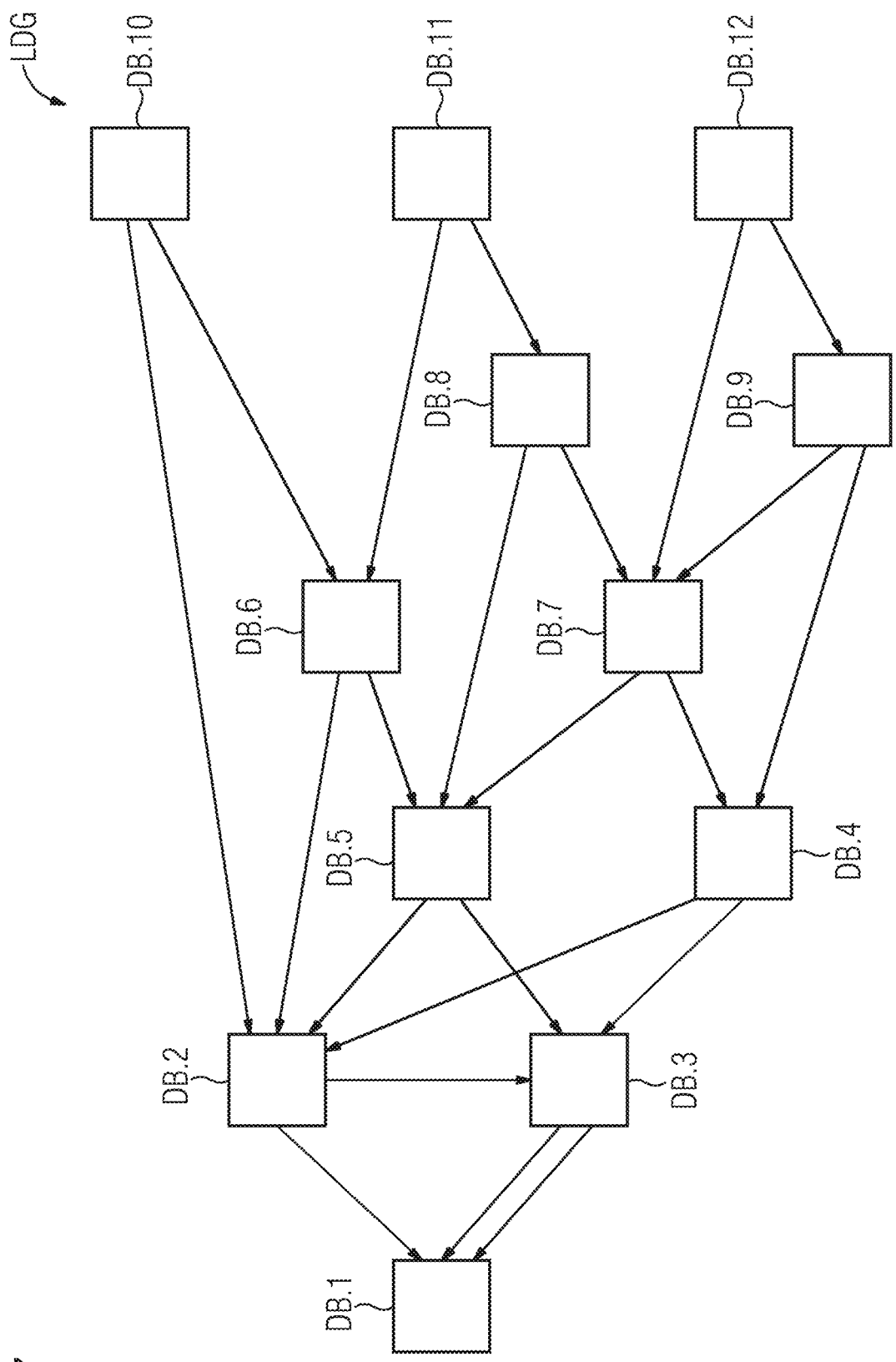
FIG. 7 displays a third embodiment of a ledger, wherein the ledger is a tangle.
Figure 8:
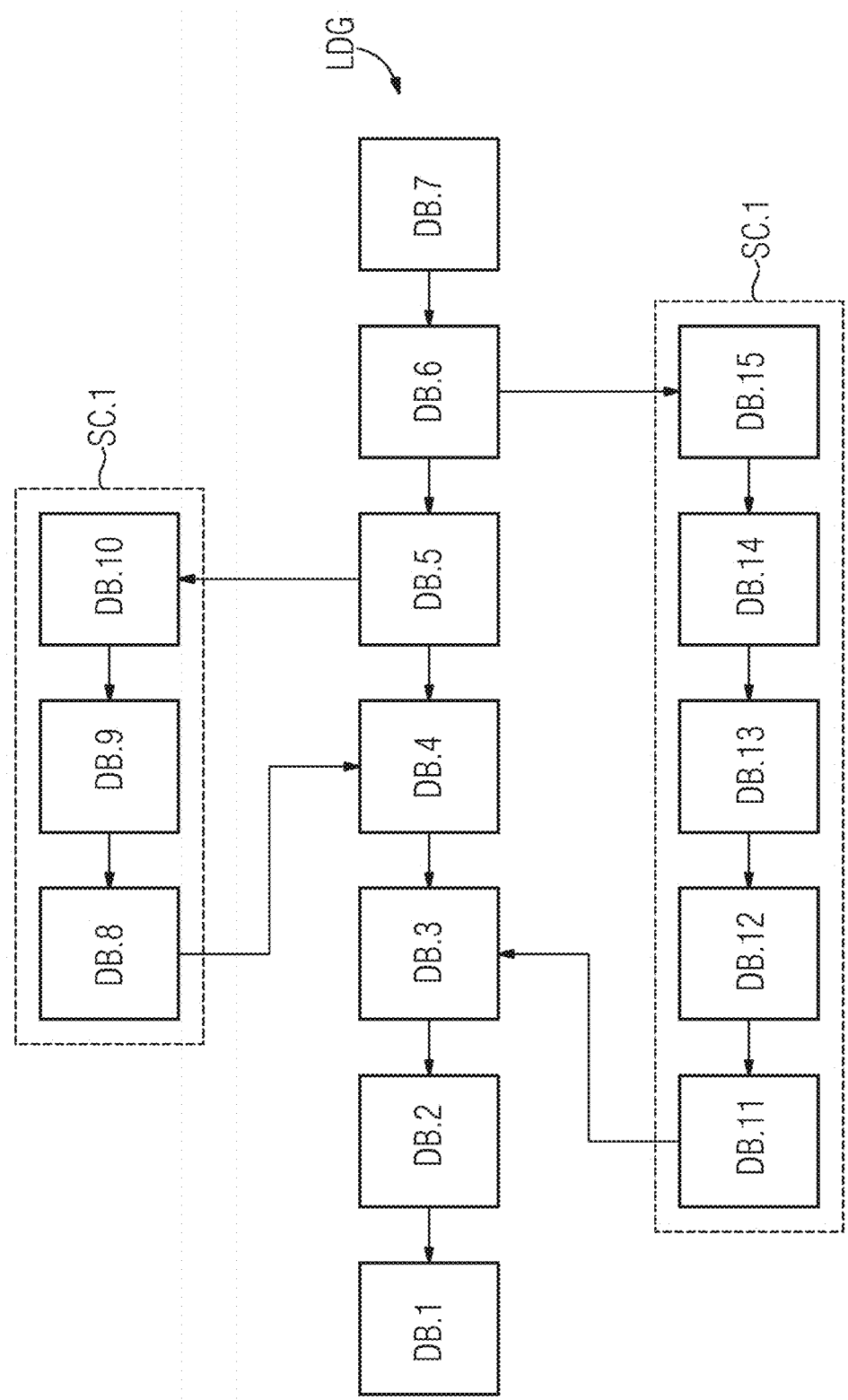
FIG. 8 displays a third embodiment of a ledger, wherein the ledger comprises sidechains.

FIG. 5 displays a first embodiment of a local database comprising data blocks, FIG. 6 displays a second embodiment of a local database comprising data blocks, FIG. 7 displays a third embodiment of a local database comprising data blocks.

In all three embodiments of a local database, an arrow going from a first data block to a second data block means that the first data block comprises a link information based on the second data block. Every one of the three embodiments comprises a genesis data block DB.1, which does not comprise a link information to another data block. An alternative name for the genesis data block DB.1 is root data block. In the first and in the second embodiment, every data block except the genesis data block DB.1 comprises one link information, in other words for each data block except the genesis data block DB.1 there is at exactly one out going arrow. In the third embodiment, every data block except the genesis data block DB.1 comprises two link informations, in other words for each data block except the genesis data block DB.1 there are exactly two outgoing arrows. It is possible that the two outgoing errors point to the same other data block, which is illustrated for the data block DB.3 in FIG. 7, in other words the two link informations of the data block DB.3 are based both on the data block DB.1. It is also possible to use another integer number of outgoing arrows or link informations, this number may be the same number for all data blocks except the genesis data block, alternatively the number may differ for different data blocks.

In all embodiments there are data blocks with no ingoing arrow, these data blocks are called barren data blocks. In other words, within the local data base there is no data block with a link information based on a barren data block. In the first embodiment, there is exactly one barren data block DB.7, in the second embodiment there are three barren data blocks DB.3, DB.6, DB.7, and in the third embodiment there are also three barren data blocks DB.10, DB.11, DB.12.

Figure 9:
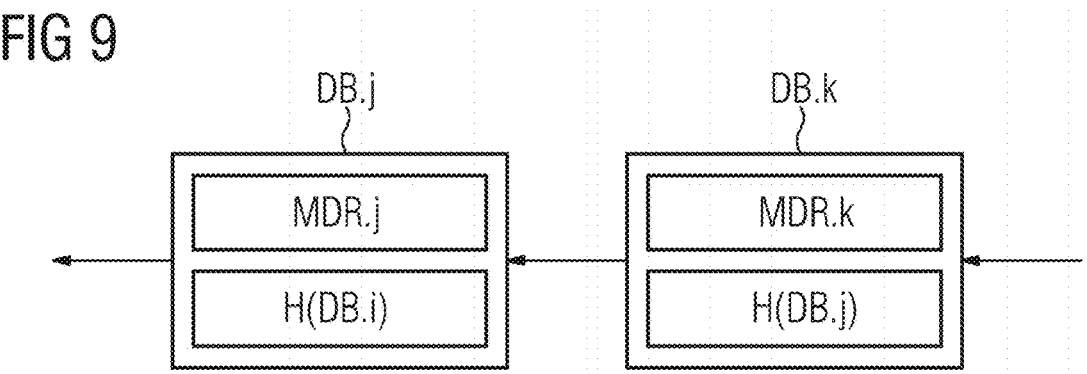
FIG. 9 displays a first embodiment of a data block.

FIG. 9 shows a first embodiment of data blocks DB.j, DB.k contained in the first ledger LDG. In particular, one of the data blocks DB.j, DB.k can be identical with the further data block FDB. The data block DB.j is the parent data block of the data block DB.k, and the data block DB.j is the direct successor of a data block DB.i not displayed in this figure. It is also possible that the data blocks DB.j, DB.k have several parents or several direct successors.

In this embodiment, the data blocks DB.j, DB.k comprise a medical data record MDR.j, MDR.k and a hash of the parent data block H(DB.i), H(DB.j). In particular, the hash of the parent data block H(DB.i), H(DB.j) is a Merkle root of the parent data block.

Figure 10:
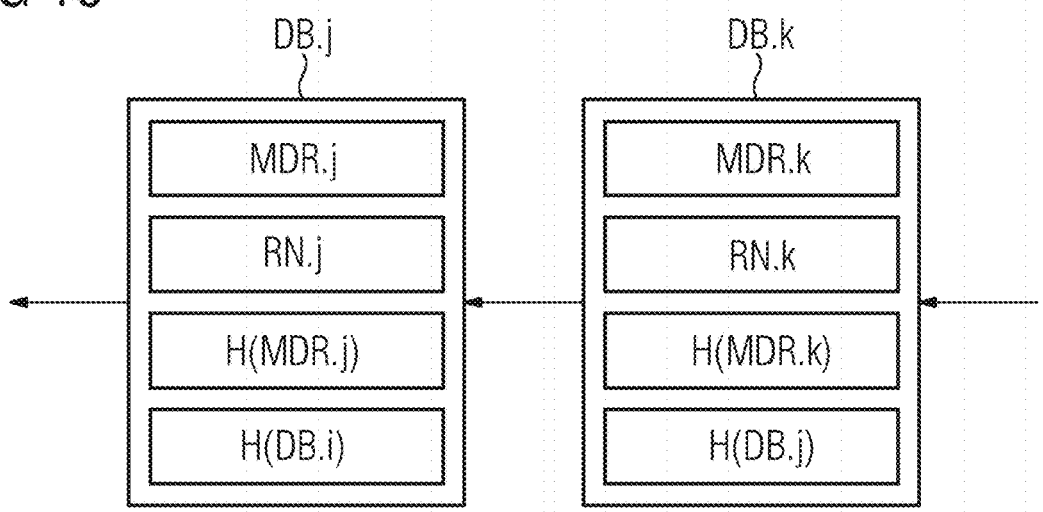
FIG. 10 displays a second embodiment of a data block.

FIG. 10 shows a first embodiment of data blocks DB.j, DB.k contained in the first ledger LDG. In particular, one of the data blocks DB.j, DB.k can be identical with the further data block FDB. The data block DB.j is the parent data block of the data block DB.k, and the data block DB.j is the direct successor of a data block DB.i not displayed in this figure. It is also possible that the data blocks DB.j, DB.k have several parents or several direct successors.

In this embodiment, the data blocks DB.j, DB.k comprise a medical data record MDR.j, MDR.k and a hash of the parent data block H(DB.i), H(DB.j). Furthermore, in this embodiment the data blocks DB.j, DB.k comprise a hash H(MDR.j), H(MDR.k) of the medical data record MDR.j, MDR.k contained in the respective data block DB.j, DB.k. The usage of the hash H(MDR.j), H(MDR.k) is optional, it ensures the integrity of the medical data record contained in the data block DB.j, DB.k. In particular, the hash H(MDR.j), H(MDR.k) is based on a Merkle root or a Merkle tree of the medical data record MDR.j, MDR.k.

Furthermore and optionally, in this embodiment the data blocks DB.j, DB.k comprise a nonce RN.j, RN.k, wherein the nonce RN.j, RN.k is chosen so that a hash based on the medical data record MDR.j, MDR.k and based on the nonce RN.j, RN.k fulfills a certain requirement, here that the hash is smaller than a given number. In general the nonce RN.j, RN.k has to be determined by calculating the hash based on the medical data record MDR.j, MDR.k and based on the nonce RN.j, RN.k for different values of the nonce RN.j, RN.k, and so creating a proof-of-work. In particular, the hash of the parent data block H(DB.i), H(DB.j) is not based on the medical data record MDR.i, MDR.j of the parent data block, but on the hash H (MDR.i), H (MDR.j) of the medical data record MDR.i, MDR.j of the parent data block, on the hash H(DB.i) of the parent data block of the parent data block, and/or on the nonce RN.i, RN.j of the parent data block. This has the advantage that for verifying the hash of the parent data block H(DB.i), H(DB.j) in the first ledger LDG (in other words, for verifying the integrity of the first ledger LDG), the possibly large medical data records MDR.i, MDR.j need not to be considered, but only their hashes H(MDR.i), H(MDR.j), which reduces the amount of computation steps necessary for verifying the integrity of the first ledger LDG.

Figure 11:
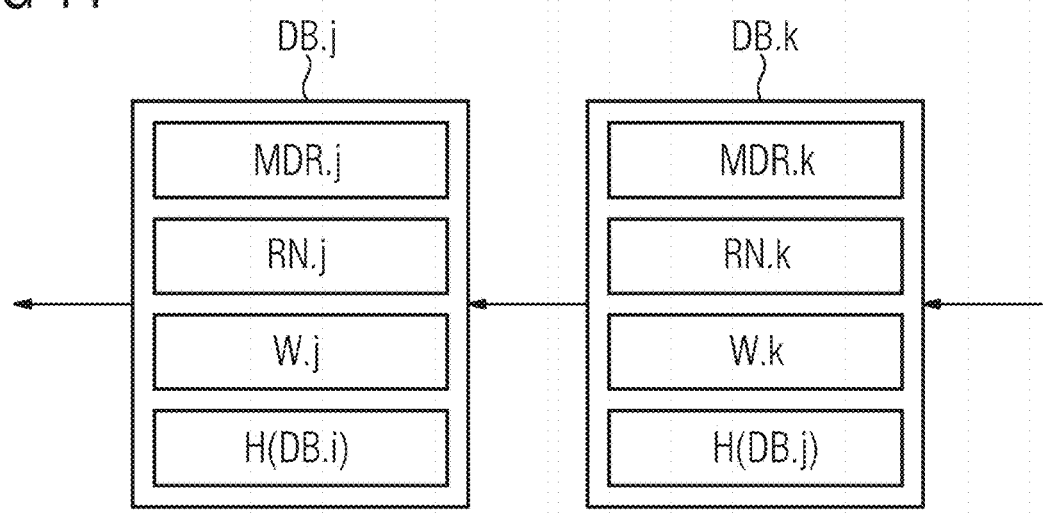
FIG. 11 displays a third embodiment of a data block.

FIG. 11 shows a first embodiment of data blocks DB.j, DB.k contained in the first ledger LDG. In particular, one of the data blocks DB.j, DB.k can be identical with the further data block FDB. The data block DB.j is the parent data block of the data block DB.k, and the data block DB.j is the direct successor of a data block DB.i not displayed in this figure. It is also possible that the data blocks DB.j, DB.k have several parents or several direct successors.

In this embodiment, the data blocks DB.j, DB.k comprise a medical data record MDR.j, MDR.k and a hash of the parent data block H(DB.i), H(DB.j). In particular, the hash of the parent data block H(DB.i), H(DB.j) is a Merkle root of the parent data block. Furthermore, in this embodiment the data blocks DB.j, DB.k comprise a nonce RN.j, RN.k, as described for FIG. 10. Furthermore, each of the data blocks DB.j, DB.k comprises a weight W.j, W.k.

In particular, the weight W.k of a data block DB.k can be based on the weight W.j of its at least one parent data block DB.j. In particular, the step of determining DET-PDB can be based on the weights W.j, W.k of the data blocks DB.j, DB.k contained in the first ledger LDG. In particular, the weight W±, W1+1 of a data block DB.j, DB.k can furthermore be based on the consensus algorithm used in creating the data block, for example in a proof-of-work consensus algorithm the weight can be proportional to the work used for determining the link information. For example, if the nonce RN.j, RN.k is chosen so that the hash based on the medical data record MDR.j, MDR.k and on the nonce RN.j, RN.k of the data block DB.j, DB.k is below a certain threshold number, the weight W.j, W.k of the data block DB.j, DB.k can be based on this threshold number.

Figure 12:
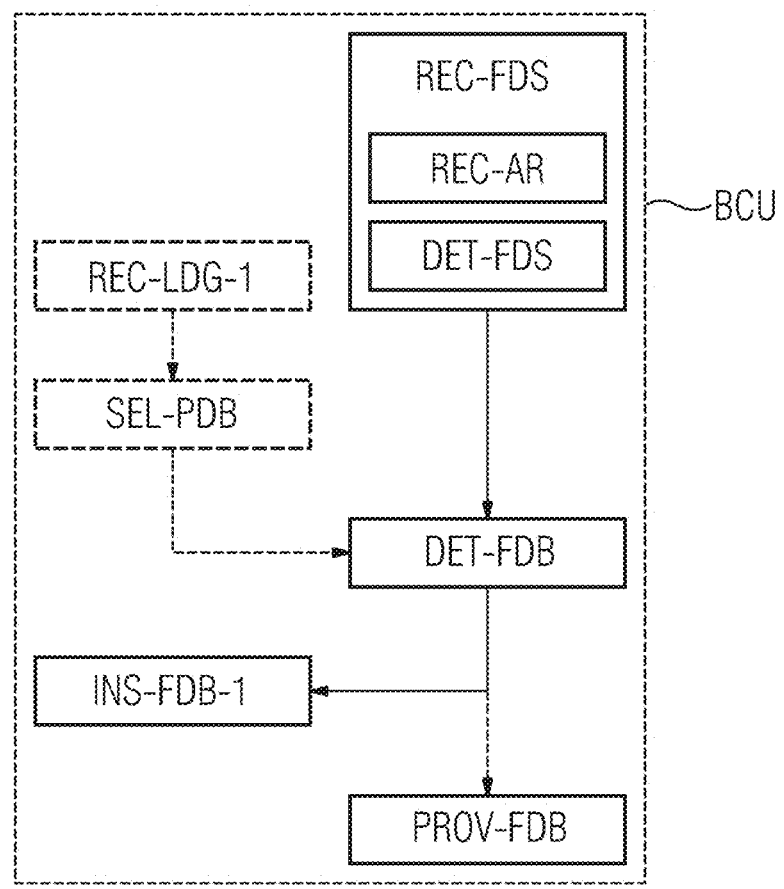
FIG. 12 displays an embodiment of the method for inserting a further data block into a first ledger, which can be used for logging the access to a medical data record.
Figure 13:
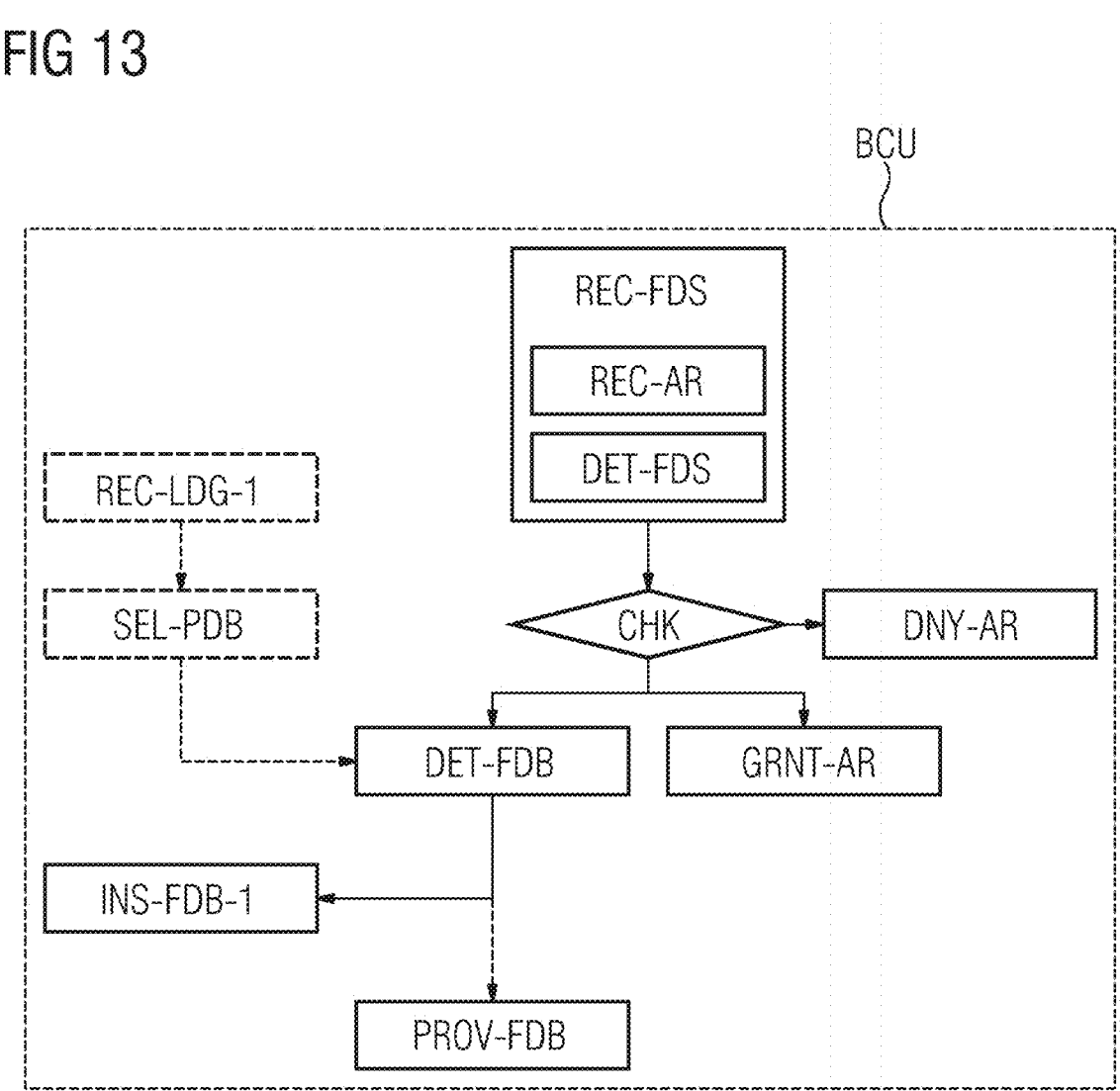
FIG. 13 displays a further embodiment of the method for inserting a further data block into a first ledger, which can be used for logging the access to a medical data record.

FIG. 12 and FIG. 13 display embodiments of the method for inserting a further data block FDB into a first ledger LDG, wherein the method can be used for logging access to a medical data record MDR.j, MDR.k, in particular for logging access of an entity to a medical data record MDR.j, MDR.k. The displayed embodiments of the method for inserting a further data block FDB into a first ledger LDG comprises all steps of the method for inserting a further data block FDB into a first ledger LDG displayed in FIG. 1. Optionally these embodiments can also comprise the additional steps displayed in FIG. 3. All method steps contained in these embodiments may comprise all advantageous enhancement and alternatives described either in the description of FIG. 1 or in the description of FIG. 3.

Figure 14:
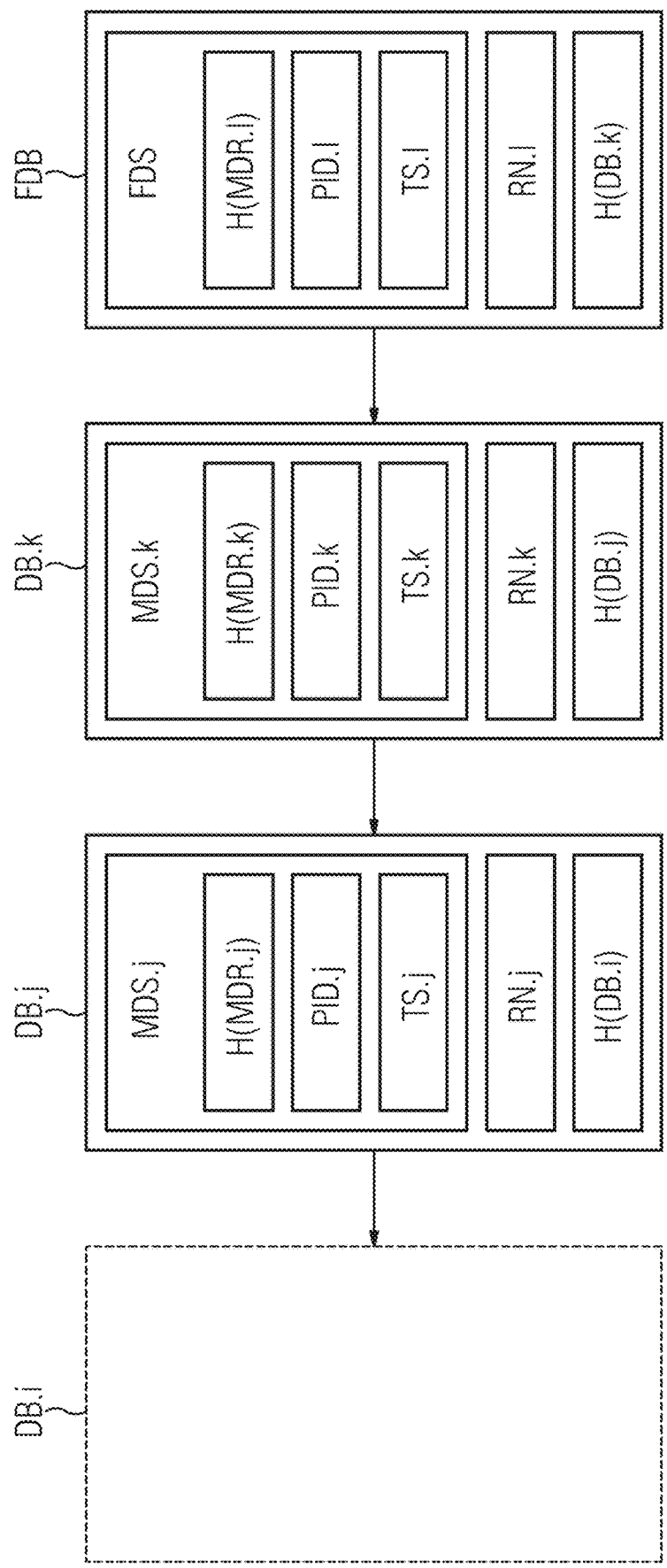
FIG. 14 displays an embodiment of a first ledger used for logging access to a medical data record.

FIG. 14 displays data blocks DB.j, DB.k contained in the first ledger LDG used in one of the methods displayed in the FIG. 12 and FIG. 13. In particular, the further data block FDB has the same structure as the displayed data blocks DB.j, DB.k, and in particular, the further data block FDB can be identical with one of the displayed data blocks DB.j, DB.k.

Each of the displayed data blocks DB.j, DB.k comprises a medical data set MDS.j, MDS.k, a nonce RN.j, RN.k, and a hash H(DB.i), H(DB.j) of the respective parent data block DB.i, DB.j. The medical data sets MDS.j, MDS.k log the access of an entity to a medical data record MDR.j, MDR.k. So in the embodiments displayed in FIG. 14, the medical data set MDS.j, MDS.k comprises a hash H(MDR.j), H (MDR.k) of the medical data record MDR.j, MDR.k being accessed, an identifier PID.j, PID.k of the entity accessing the medical data record MDR.j, MDR.k and a timestamp TS.j, TS.k corresponding to the time of the access of the entity to the medical data record MDR.j, MDR.k.

In this embodiment the entity accessing the medical data record MDR.j, MDR.k is a person accessing the medical data record MDR.j, MDR.k, and the identifier PID.j, PID.k of the person accessing the medical data record MDR.j, MDR.k is the ID of the person in a central databank (e.g. a social insurance number). Alternatively, the identifier PID.j, PID.k of the person accessing the medical data record MDR.j, MDR.k can comprise personal data of the person accessing the medical data record MDR.j, MDR.k, e.g. the name and/or the date of birth of the person. Alternatively, the identifier PID.j, PID.k of the person or a general entity accessing the medical data record MDR.j, MDR.k can comprise a public key associated with the person. Alternatively, the identifier PID.j, PID.k of the person or a general entity accessing the medical data record MDR.j, MDR.k can be a signature signed with a private key associated with the person or the general entity, in particular the signature can be created based on the medical data record MDR.j, MDR.k, the hash hash H (MDR.j), H(MDR.k) of the medical data record MDR.j, MDR.k, and/or on the timestamp TS.j, TS.k corresponding to the time of the access of the person or the general entity to the medical data record MDR.j, MDR.k.

In the embodiments displayed in FIG. 12 and FIG. 13, the step of receiving REC-FDS a further medical data set comprises the step of receiving REC-AR an access request directed at the medical data record MDR.1 with the interface BCU.IF from the entity, and the step of determining the further medical dataset FDS based on the access request and based on the medical data record MDR.1 with the calculation unit BCU.CU.

In the displayed embodiments the access request comprises an identifier PID.1 of the entity accessing the medical data record MDR.1, and information about the medical data record MDR.1 to be accessed. In this embodiment, the information about the medical data record MDR.1 to be accessed is a hash H (MDR.1) of the medical data record MDR.1 to be accessed. Alternatively, the information about the medical data record MDR.1 to be accessed is a link to the medical data record MDR.1 to be accessed, in particular an unified resource locater (an acronym is "URL") pointing to the medical data record MDR.1 to be accessed. In particular, the URL of the medical data record MDR.1 to be accessed can comprise a hash H (MDR.1) of the medical data record MDR.1 to be accessed.

In these embodiments, the medical data record MDR.1 to be accessed is diagnostic data related to a patient. Diagnostic data can comprise one or more medical images of the patient (e.g. originating from X-ray fluoroscopy, angiography, computed tomography, magnetic resonance imaging, positron emission tomography, ultrasound imaging), diagnostic data can also comprise laboratory data (e.g. originating from laboratory diagnostic with respect to blood of a patient, urine of a patient, liquor of a patient or feces of a patient), diagnostic data can also comprise a medical diagnosis in a structured or unstructured format. Alternatively, diagnostic data can also comprise a combination of several of the mentioned alternatives.

In the step of determining DET-FDS the further medical dataset FDS based on the access request and based on the medical data record MDR.1 the further medical dataset FDS is determined such that the further medical dataset FDS comprises the hash H (MDR.1) of the medical data record MDR.1 being accessed, the identifier PID.1 of the entity accessing the medical data record MDR.1 and the timestamp TS.1 corresponding to the time of the access to the medical data record MDR.1. In particular, the step of determining the further medical dataset FDS can comprise calculating the hash H (MDR.1) of the medical data record MDR.1 being accessed by applying a hash function on the medical data record MDR.1.

Alternatively, the further medical data set FDS can furthermore comprise personal data related to the patient (e.g. the name of the patient, the sex of the patient, the age of the patient, the size of the patient, the weight of the patient, or any combination thereof). The further medical data set FDS may also be defined with respect to a plurality of access requests to medical data records from the entity or from different entities; in this case the further medical data dataset FDS comprises the respective data for all of the access requests.

In particular the step of determining DET-FDS the further medical dataset FDS is executed such that the further medical dataset FDS complies with the format of the medical datasets MDS.j, MDS.k already contained in the data blocks DB.i, DB.j, DB.k already present in the first ledger LDG. In particular, also the medical datasets MDS.j, MDS.k comprise the hashes H(MDR.j), H(MDR.k) of the medical data records MDR.j, MDR.k having been accessed, the identifiers PID.j, PID.k of the entities having accessed the respective medical data record MDR.j, MDR.k and the timestamp TS.j, TS.k corresponding to the time of the access to the medical data records MDR.j, MDR.k.

The method displayed in FIG. 12 furthermore comprises the step of providing PROV-FDB the further data block FDB with the interface BCU.IF of the block creation unit BCU. In this embodiment, the step of providing PROV-FDB the further data block FDB is executed after the step of inserting INS-FDB-1 the further data block into the first ledger LDG. Alternatively, the step of providing PROV-FDB the further data block FDB can also be executed before the step of inserting INS-FDB-1 the further data block FDB into the first ledger LDG. Alternatively, the step of providing PROV-FDB the further data block FDB can also be executed parallel to the step of inserting INS-FDB-1 the further data block FDB into the first ledger LDG. In other words, the steps of providing PROV-FDB the further data block FDB is independent of the step of inserting INS-FDB-1 the further data block FDB into the first ledger LDG.

The embodiment of the method for inserting a further data block FDB into a first ledger LDG displayed in FIG. 13 furthermore comprises the steps of per forming CHK a check of the authorization of the entity to access the medical data record MDR.j, the step of in the case of a positive check, granting access GRNT-ACC to the entity, and the step of in the case of a negative check, denying access DNY-ACC to the entity.

In the displayed embodiment of FIG. 13 the step of performing a check CHK is executed after the step of receiving REC-FDS the further medical data set FDS. Alternatively, the step of performing a check CHK can also be executed after the step of determining DET-FDB the further data block FDB, after the step of inserting INS-FDB-1 the further data block FDB into the first ledger, or after the step of providing the further data block FDB.

In the displayed embodiment of FIG. 13, the step of granting access GRNT-ACC to the entity is performed after the step of performing a check CHK, and before the step of determining DET-FDB the further data block. Alternatively, the step of granting access GRNT-ACC to the entity can be performed after the step of determining DET-DFB the further data block FDB, after the step of inserting INS-FDB-1 the further data block FDB into the first ledger, or after the step of providing the further data block FDB.

The step of performing a check CHK can comprise determining whether the entity is allowed to access the medical data record MDR.1. In particular the step of performing a check CHK can comprise determining whether the entity is part of a group of entities, wherein the group of entities is allowed to access the medical data record MDR.1. The entities or group of entities allowed to access the medical data record MDR.1 can be stored in a database, so that the step of performing a check CHK comprises accessing the database of entities allowed to access the medical data record. The step of performing a check CHK can also comprise verifying the identity of the entity requesting access to the medical data record MDR.1, for example relying on a shared secret and/or on a digital certificate of the entity requesting access to the medical data record, wherein the shared secret and/or the digital certificate of the entity is comprised by the access request.

In the displayed embodiment of FIG. 13, if the result of the check is negative, the step of denying access DNY-ACC to the entity is executed. In particular, in the case of a negative check the further medical dataset FDS can furthermore comprise a denial record. The denial record comprises information about the reason the access was denied, e.g. an error code indicating the reason for the entity not being allowed to access the medical data record MDR.j. In the case of a negative check, in this embodiment the steps of determining DET-FDB the further datablock FDB and the step of inserting INS-FDB-1 the further data block FDB into the first ledger LDG are not executed.

In particular, the step of performing a check CHK can also be executed after the step of inserting INS-FDB-1 the further data block FDB into the ledger LDG, wherein the step of performing a check CHK comprises determining whether the further data block FDB actually has been entered into the first ledger LDG. This has the advantage that it can be ensured that each access request is actually registered in the first ledger LDG.

Figure 15:
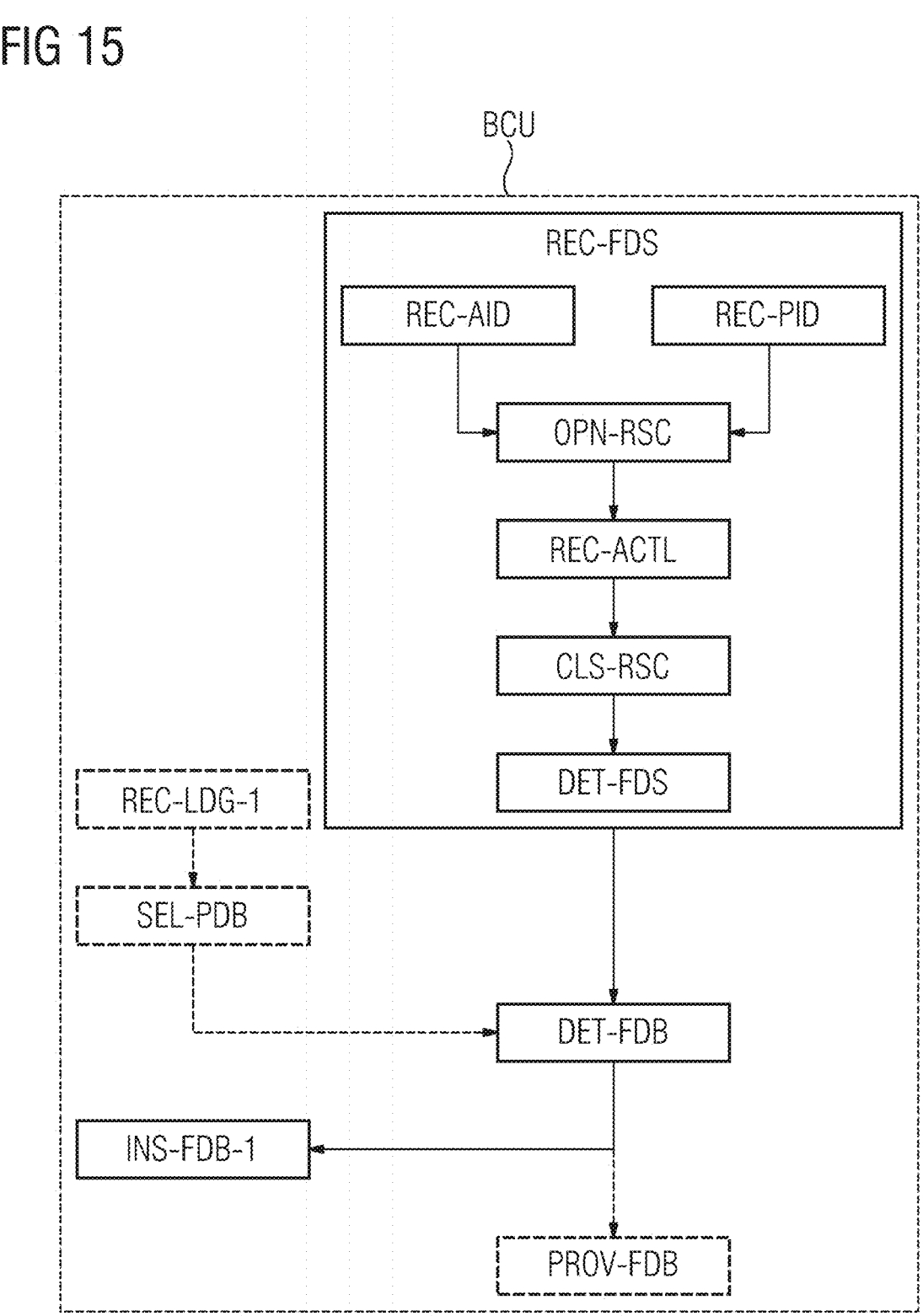
FIG. 15 displays an embodiment of the method for inserting a further data block into a first ledger, which can be used for logging access to a medical apparatus.

FIG. 15 displays an embodiment of the method for inserting a further data block FDB into a first ledger LDG, wherein the method can be used for logging the remote access to a medical apparatus MA, in particular for logging the remote access of an entity to the medical apparatus MA. The displayed embodiment of the method for inserting a further data block FDB into a first ledger LDG comprises all steps of the method for inserting a further data block FDB into a first ledger LDG displayed in FIG. 1. Optionally these embodiments can also comprise the additional steps displayed in FIG. 3. All method steps contained in these embodiments may comprise all advantageous enhancement and alternatives described either in the description of FIG. 1 or in the description of FIG. 3.

Figure 16:
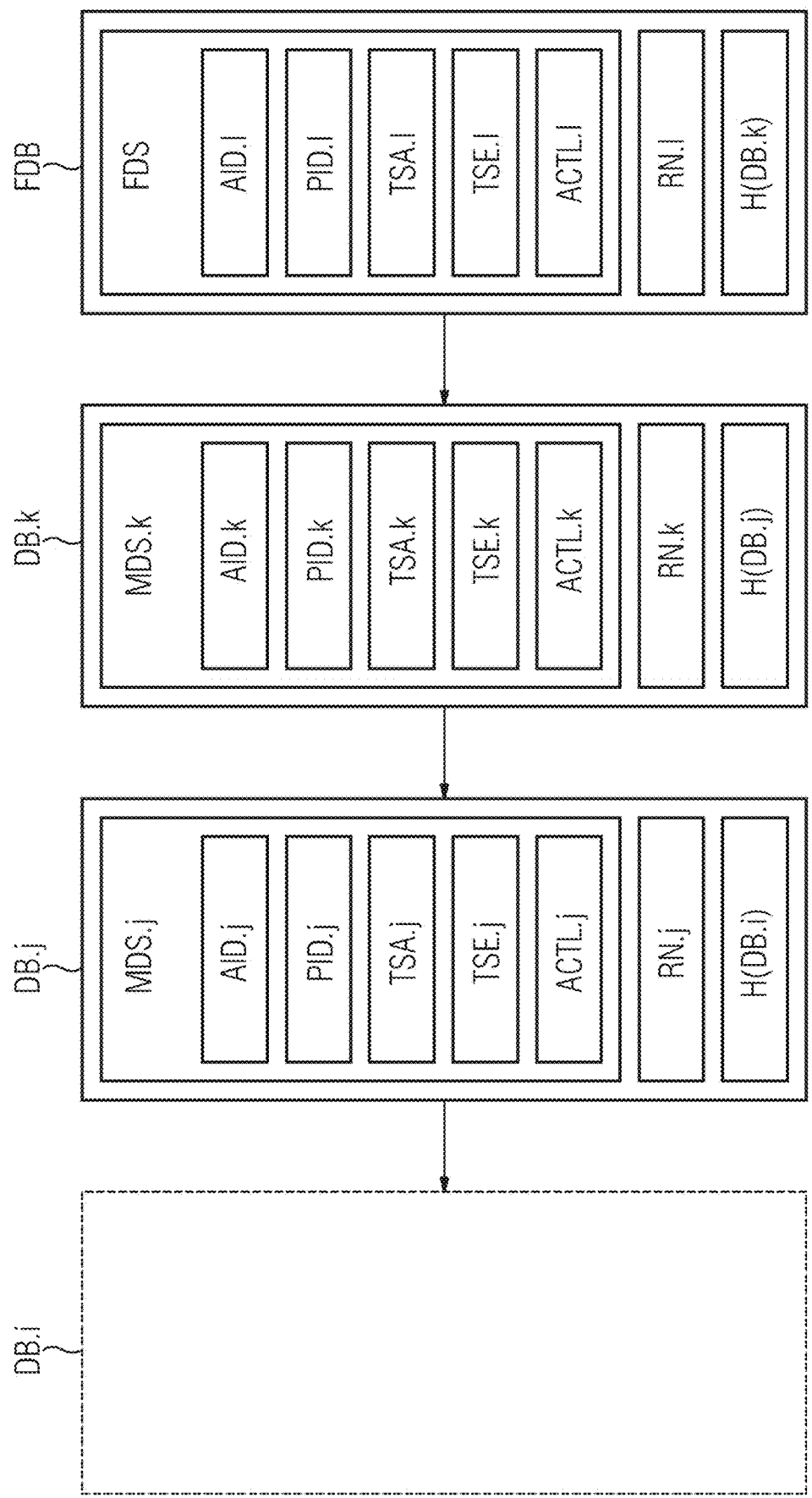
FIG. 16 display an embodiment of a first ledger used for logging access to a medical apparatus.

FIG. 16 displays data blocks DB.j, DB.k contained in the first ledger LDG used in the method displayed in FIG. 16. In particular, the further data block FDB has the same structure as the displayed data blocks DB.j, DB.k, and in particular, the further data block FDB can be identical with one of the displayed data blocks DB.j, DB.k.

Each of the displayed data blocks DB.j, DB.k comprises a medical data set MDS.j, MDS.k, a nonce RN.j, RN.k, and a hash H(DB.i), H(DB.j) of the respective parent data block DB.i, DB.j.

The medical data sets MDS.j, MDS.k log the access of an entity to a medical apparatus MA. So in the embodiments displayed in FIG. 16, the medical data set MDS.j, MDS.k comprises an identifier AID.j, AID.k of the medical apparatus being accessed, an identifier PID.j, PID.k of the entity accessing the medical apparatus MA, an access time TSA.j, TSA.k corresponding to the time of access of the entity to the medical apparatus MA, an egress time TSE.j, TSE.k corresponding to the time of egress of the entity from the medical apparatus MA, and an action log ACTL.j, ACTL.k of the action performed by the entity while having accessed the medical apparatus MA.

In this embodiment the entity accessing the medical apparatus MA is a person accessing the medical apparatus MA, and the identifier PID.j, PID.k of the person accessing the apparatus is the ID of the person in a central databank (e.g. a social insurance number). Alternatively, the identifier PID.j, PID.k of the person accessing the medical apparatus MA can comprise personal data of the person accessing the medical apparatus MA, e.g. the name and/or the date of birth of the person. Alternatively, the identifier PID.j, PID.k of the person or a general entity accessing the medical apparatus MA can comprise a public key associated with the person. Alternatively, the identifier PID.j, PID.k of the person or a general entity accessing the medical apparatus MA can be a signature signed with a private key associated with the person or the general entity, in particular the signature can be created based on the identifier AID.j, AID.k of the medical apparatus MA, the access time TSA.j, TSA.k, the egress time TSE.j, TSE.k, and/or the action log ACTL.j, ACTL.k.

In the embodiment displayed in FIG. 15, the step of receiving REC-FDS a further medical data set comprises the step of receiving REC-AID an identifier AID.1 of the medical apparatus MA being accessed with the interface BCU.IF, and the step of receiving REC-PID an identifier PID.1 of the entity accessing the medical apparatus MA. In this embodiment, the entity accessing the medical apparatus MA can issue an access request to the medical apparatus MA (e.g. by initiating an SSH, VNC or Remote Desktop connection), wherein the access request comprise the identifier AID.1 of the medical apparatus MA and the identifier PID.1 of the entity accessing the medical apparatus MA.

The embodiment displayed in FIG. 15 can furthermore comprise an (optional and non-displayed) step of checking the authorization of the entity accessing the medical apparatus MA based on the identifier AID.1 of the medical apparatus MA and the identifier PID.1 of the entity accessing the medical apparatus MA.

Furthermore the embodiment displayed in FIG. 15 comprises the step of opening OPN-RSC a remote service connection between the entity accessing the medical apparatus MA and the medical apparatus MA. In the described case, the block verification unit BVU is identical with the medical apparatus MA being accessed. Alternatively the block verification unit BVU can be different from the medical apparatus MA being accessed, in this case the step of opening OPN-RSC the remote service connection can comprise sending a message to the medical apparatus MA to open the remote service connection. Furthermore, in this embodiment the step of opening OPN-RSC the remote service connection comprise recording of the access time TSA.1.

The embodiment displayed in FIG. 15 furthermore comprises the step of recording REC-ACYL an action log ACTL.1, wherein the action log ACTL.1 comprises a subset of the actions or all the action performed by the entity on the medical apparatus MA by using the remote service connections. The action log ACTL.1 can comprise a list of commands sent from the entity through the re mote service connection to the medical apparatus MA, for example the key strokes and the mouse movements of the entity can be recorded.

Alternatively it is also possible to record the actions at the medical apparatus MA, e.g. which buttons have be pressed and which inputs are done by the entity using the remote service connection.

The embodiment displayed in FIG. 15 furthermore comprises the step of closing CLS-RSC the remote service connection. In particular, the step of closing CSL-RSC the remote service connection comprises recording of the egress time TSE.1. Furthermore, the embodiment displayed in FIG. 15 comprises the step of determining DET-FDS the further medical dataset FDS based on the identifier PID.1 of the entity accessing the medical apparatus MA, on the identifier AID.1 of the medical apparatus MA, on the access time TSA.1, on the egress time TSE.1 and on the action log ACTL.1. It can comprise storing the recorded actions at a Webserver, and determining the action log ACTL.1 comprising a link to the recorded actions in the Webserver and a hash of the recorded actions in the Webserver. In particular the step of determining DET-FDS the further medical dataset FDS is executed such that the further medical dataset FDS complies with the format of the medical datasets MDS.j, MDS.k already contained in the data blocks DB.i, DB.j, DB.k already present in the first ledger LDG.

Figure 17:
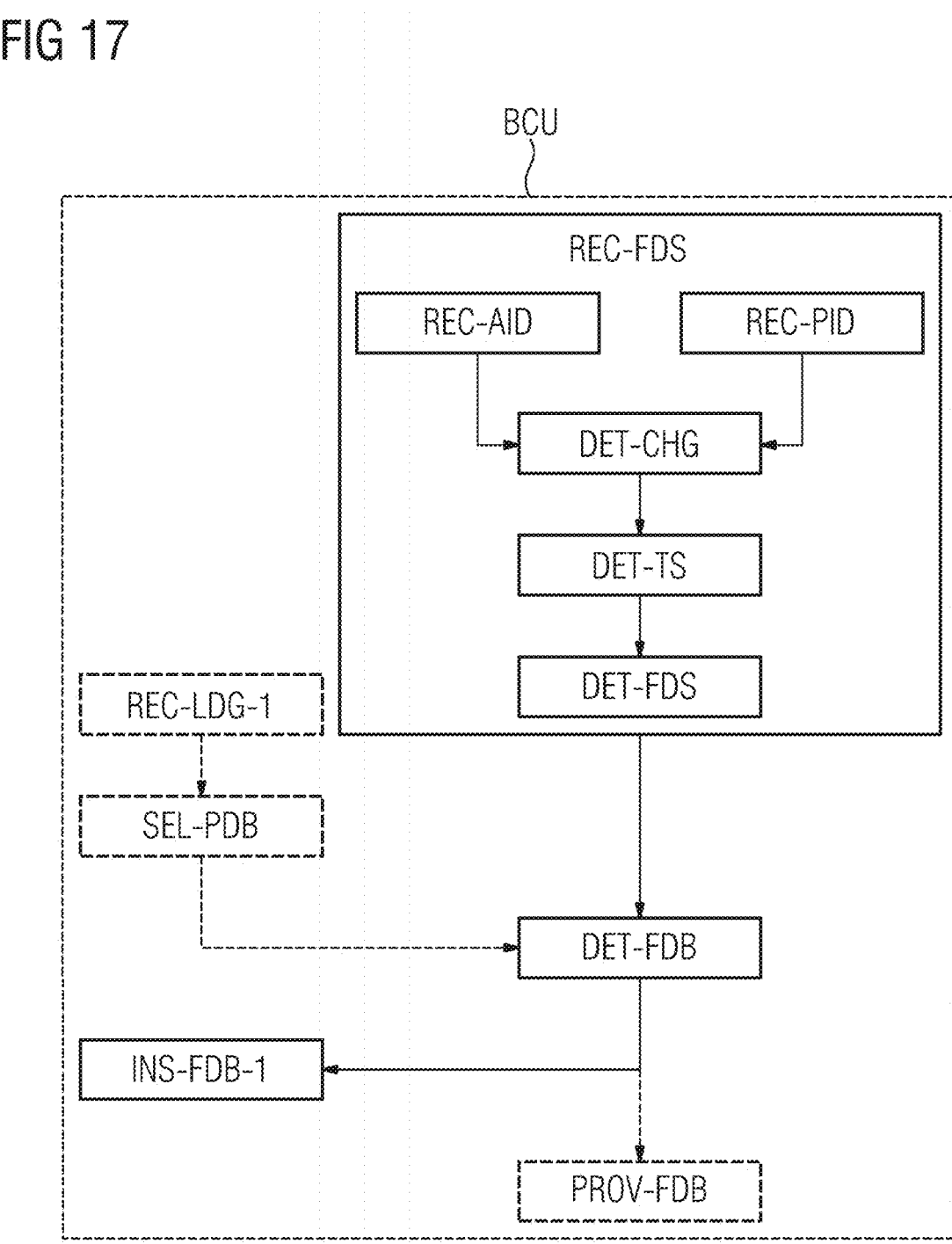
FIG. 17 displays a further embodiment of the method for inserting a further data block into a first ledger, which can be used for logging access to a medical apparatus.

FIG. 17 displays an embodiment of the method for inserting a further data block FDB into a first ledger LDG, wherein the method can be used for logging access to a medical apparatus MA while performing local service, in particular for logging the installation of a component by an entity to the medical apparatus MA, the removal of a component by an entity from the medical apparatus MA, and/or the exchange of a first component with a second component by an entity at the medical apparatus MA. The component, the first component and the second component can be a hardware component and/or a software component.

The displayed embodiment of the method for inserting a further data block FDB into a first ledger LDG comprises all steps of the method for inserting a further data block FDB into a first ledger LDG displayed in FIG. 1. Optionally these embodiments can also comprise the additional steps displayed in FIG. 3. All method steps contained in these embodiments may comprise all advantageous enhancement and alternatives described either in the description of FIG. 1 or in the description of FIG. 3.

Figure 18:
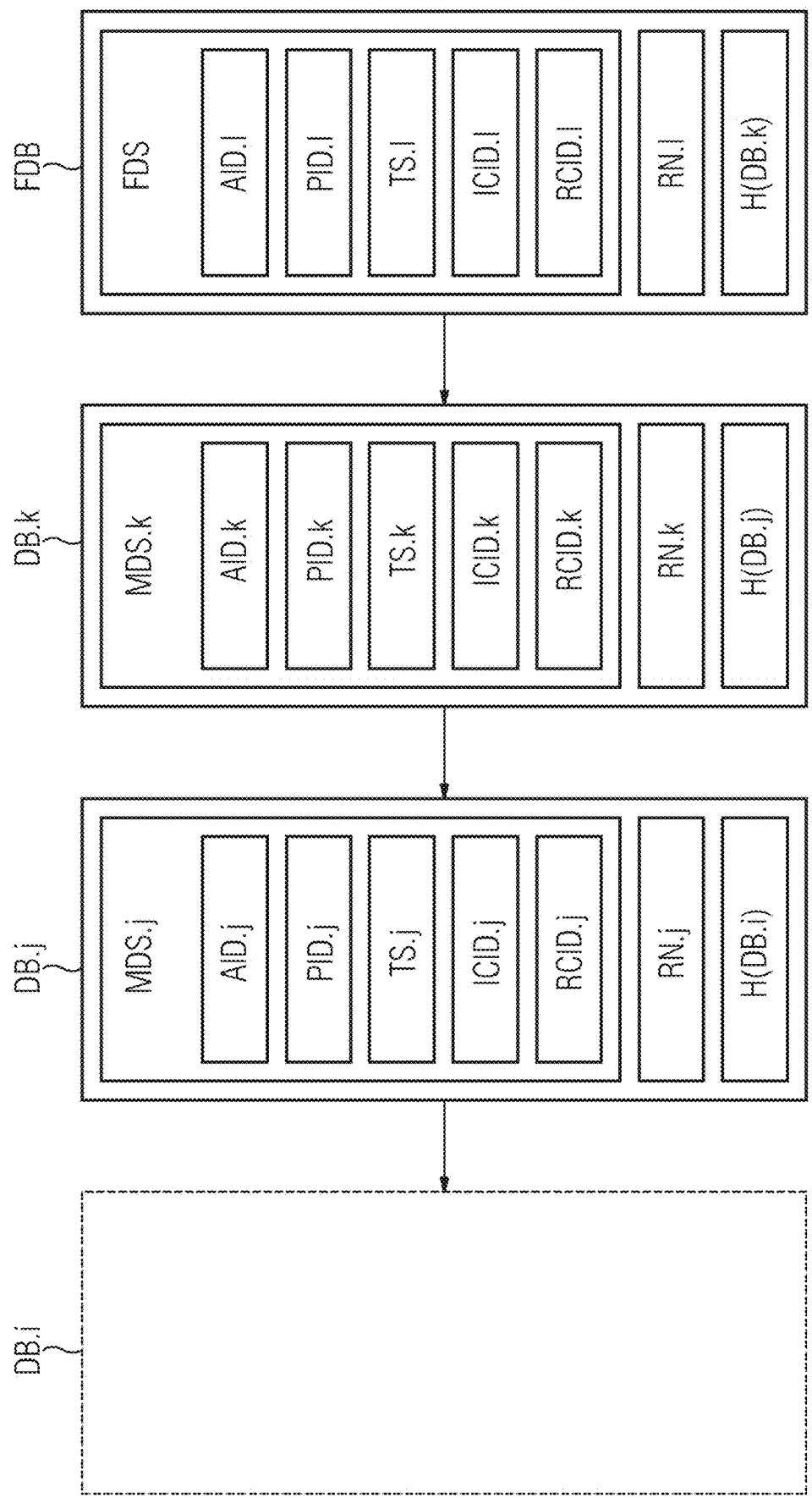
FIG. 18 displays a further embodiment of a first ledger used for logging access to a medical apparatus.

FIG. 18 displays data blocks DB.j, DB.k contained in the first ledger LDG used in the method displayed in FIG. 16. In particular, the further data block FDB has the same structure as the displayed data blocks DB.j, DB.k, and in particular, the further data block FDB can be identical with one of the displayed data blocks DB.j, DB.k.

Each of the displayed data blocks DB.j, DB.k comprises a medical data set MDS.j, MDS.k, a nonce RN.j, RN.k, and a hash H(DB.i), H(DB.j) of the respective parent data block DB.i, DB.j.

The medical data sets MDS.j, MDS.k log the access of an entity to a medical apparatus MA, installing, removing and/or exchanging components. So in the embodiments displayed in FIG. 18, the medical data set MDS.j, MDS.k comprises an identifier AID.j, AID.k of the medical apparatus being accessed, an identifier PID.j, PID.k of the entity accessing the medical apparatus MA, a time TS.j, TS.k corresponding to the time of access of the entity to the medical apparatus MA, an identifier ICID.j, ICID.k of a component being installed to the medical apparatus, and an identifier RCID.j of a component being removed from the medical apparatus MA.

In this embodiment the entity accessing the medical apparatus MA is a person accessing the medical apparatus MA, and the identifier PID.j, PID.k of the person accessing the apparatus is the ID of the person in a central databank (e.g. a social insurance number). Alternatively, the identifier PID.j, PID.k of the person accessing the medical apparatus MA can comprise personal data of the person accessing the medical apparatus MA, e.g. the name and/or the date of birth of the person. Alternatively, the identifier PID.j, PID.k of the person or a general entity accessing the medical apparatus MA can comprise a public key associated with the person. Alternatively, the identifier PID.j, PID.k of the person or a general entity accessing the medical apparatus MA can be a signature signed with a private key associated with the person or the general entity, in particular the signature can be created based on the identifier AID.j, AID.k of the medical apparatus MA, the time TS.j, TS.k corresponding to the time of access of the entity to the medical apparatus MA, the identifier ICID.j, ICID.k of a component being installed to the medical apparatus, and/or the identifier RCID.j of a component being re moved from the medical apparatus MA.

In this embodiment, the component installed to or removed from the medical apparatus MA can be a hardware and/or a software component. Alternatively, it is also possible to log installation and removal only of hardware components or only of software components. The identifier ICID.j, ICID.k of a hardware component being installed to the medical apparatus MA and/or the identifier RCID.j, RCID.k of a hardware component being removed from the medical apparatus MA comprise a model number of the component and/or a serial number of the hardware component. The identifier ICID.j, ICID.k of a software component being installed to the medical apparatus MA and/or the identifier RCID.j, RCID.k of a software component being removed from the medical apparatus MA comprise a version number of the software component.

In particular, if the action performed by the entity is the installation of a component, the identifier ICID.j, ICID.k of the component being installed to the medical apparatus MA is non-empty, and the identifier RCID.j, RCID.k of a component being removed from the medical apparatus MA is empty. In particular, if the action performed by the entity is the removal of a component, the identifier ICID.j, ICID.k of a component being installed to the medical apparatus MA is empty, and the identifier RCID.j, RCID.k of the component being removed from the medical apparatus MA is non-empty. In particular, if the action performed by the entity is the exchange of a component, the identifier ICID.j, ICID.k of a component being installed to the medical apparatus MA and the identifier RCID.j, RCID.k of the component being removed from the medical apparatus MA are both non-empty.

In the embodiment displayed in FIG. 18, the step of receiving REC-FDS a further medical data set comprises the step of receiving REC-AID an identifier AID.1 of the medical apparatus MA being accessed with the interface BCU.IF, and the step of receiving REC-PID an identifier PID.1 of the entity accessing the medical apparatus MA. In this embodiment, the entity accessing the medical apparatus MA and installing, removing or exchanging a component is logged on to the medical apparatus MA using some log-in credentials, and the identifier PID.1 of the entity accessing the medical apparatus MA can be determined based on the log-in credentials.

The embodiment displayed in FIG. 17 furthermore comprises the step of deter mining DET-CHG a change of the medical apparatus MA, wherein a change can be the installation of a component, the removal of a component, and/or the exchange of a component of the medical apparatus MA. For example, the calculation unit BCU.CU can create a list of the components of the medical apparatus MA on a regular basis, and compare the current list with a previous version of the list for detecting changes. Alternatively, the installation and/or the removal of a component can start a software routine which determines the change of the medical apparatus MA. In particular, if the component is a hardware component, the hardware component can comprise a memory (for example an EPROM) that can be read-out by the medical apparatus MA, the memory storing the model number and the serial number of the respective hardware component. In particular, of the component is a software component, the software component can comprise a configuration file comprising the version number of the software. Alternatively, a software component being executed by the medical apparatus MA can output its version number if called with a certain command line argument or execution argument.

Furthermore the embodiment displayed in FIG. 17 comprises the step of deter mining DET-TS a timestamp TS.1, wherein the timestamp corresponds to the time of the installation, the removal or the exchange of the component.

Figure 19:
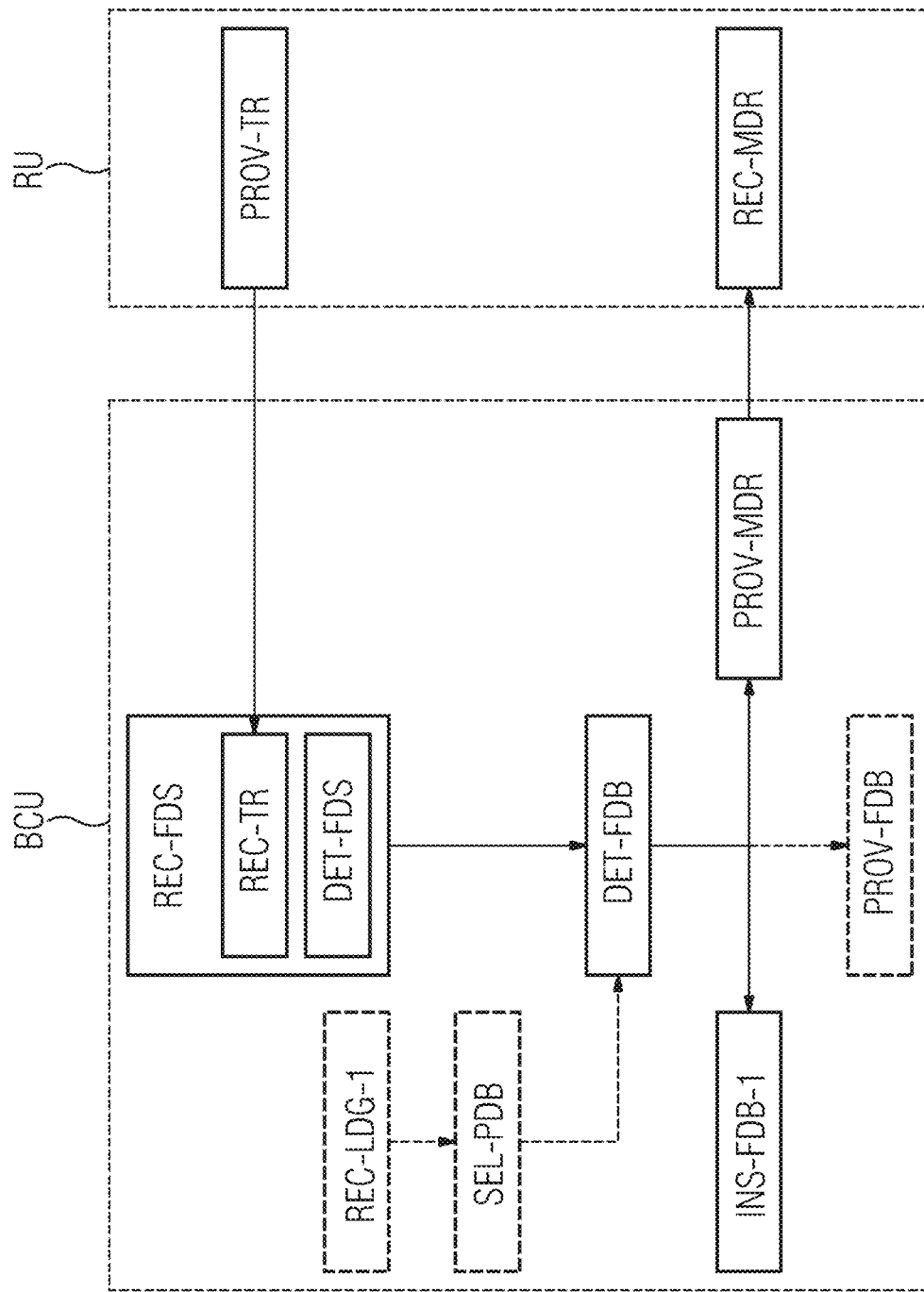
FIG. 19 displays an embodiment of the method for inserting a further data block into a first ledger, which can be used for logging a transfer of a medical data record.
Figure 20:
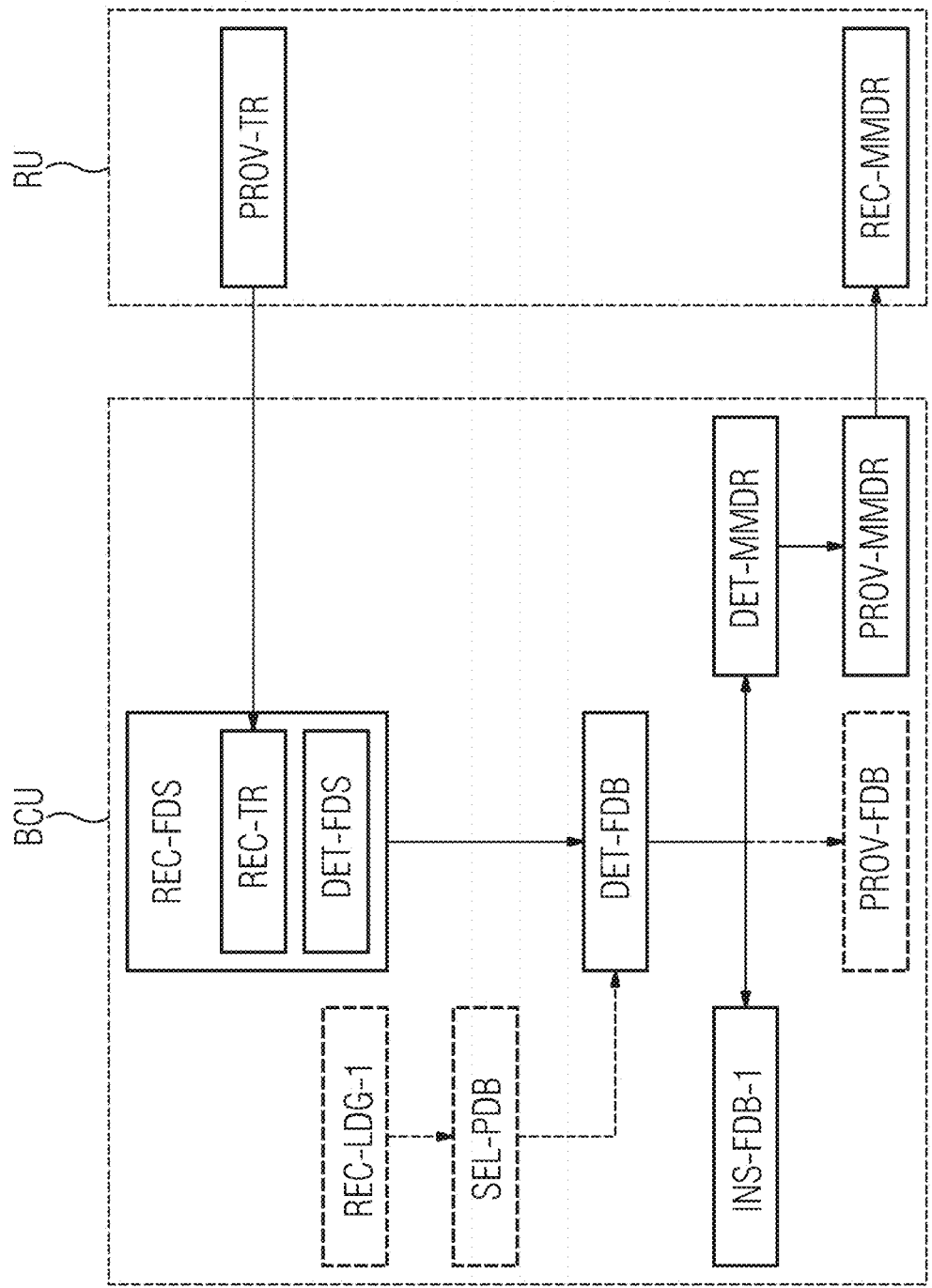
FIG. 20 displays a further embodiment of the method for inserting a further data block into a first ledger, which can be used for logging a transfer of a medical data record.
Figure 21:
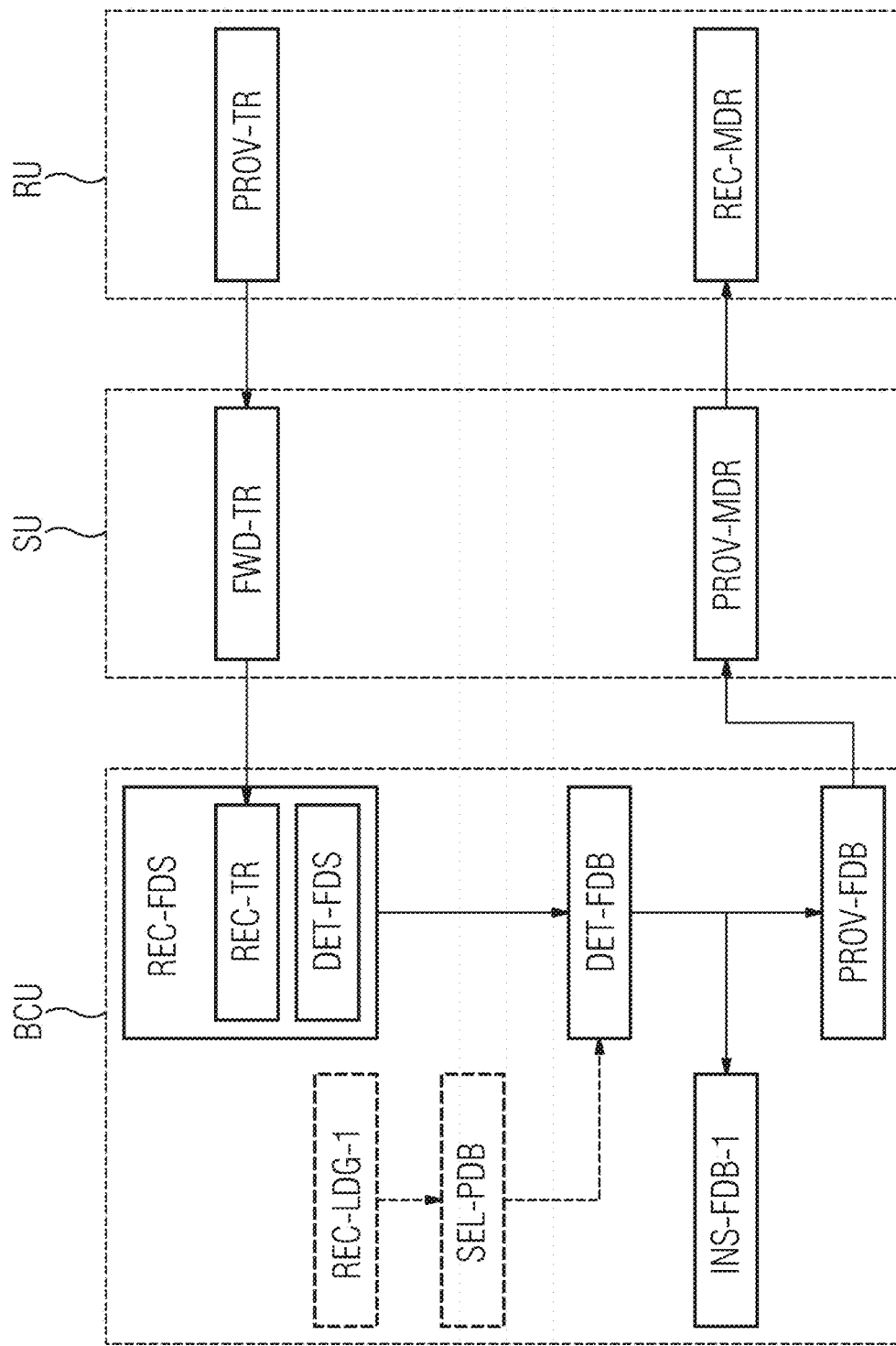
FIG. 21 displays a further embodiment of the method for inserting a further data block into a first ledger, which can be used for logging a transfer of a medical data record.

The embodiment displayed in FIG. 17 furthermore comprises a step of determining DET-FDB the further data block FDB, which is not displayed in FIG. 17. In particular the step of determining DET-FDS the further medical dataset FDS is executed such that the further medical dataset FDS complies with the format of the medical datasets MDS.j, MDS.k already contained in the data blocks DB.i, DB.j, DB.k already present in the first ledger LDG. FIG. 19, FIG. 20 and FIG. 21 display embodiments of the method for inserting a further data FDB into a first ledger LDG, wherein the method can be used for logging the transfer of a medical data record MDR.j, MDR.k from a first entity to a second entity.

The displayed embodiments of the method for inserting a further data block FDB into a first ledger LDG comprises all steps of the method for inserting a further data block FDB into a first ledger LDG displayed in FIG. 1. Optionally these embodiments can also comprise the additional steps displayed in FIG. 3. All method steps contained in these embodiments may comprise all advantageous enhancement and alternatives described either in the description of FIG. 1 or in the description of FIG. 3.

Figure 22:
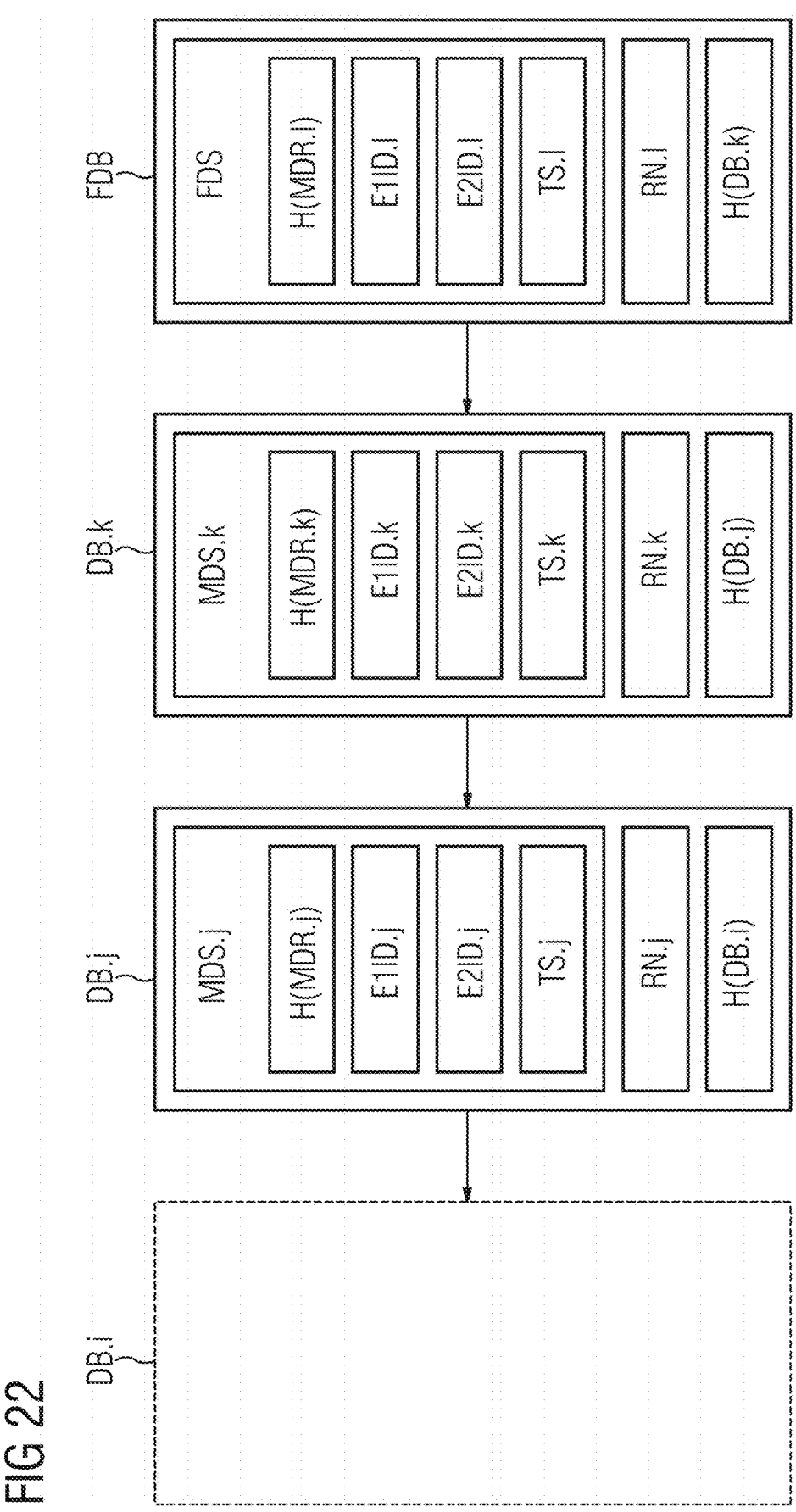
FIG. 22 displays an embodiment of a first ledger used for logging the transfer of a medical data record.

FIG. 22 displays data blocks DB.j, DB.k contained in the first ledger LDG used in one of the methods displayed in the FIG. 19, FIG. 20 and FIG. 21. In particular, the further data block FDB has the same structure as the displayed data blocks DB.j, DB.k, and in particular, the further data block FDB can be identical with one of the displayed data blocks DB.j, DB.k.

Each of the displayed data blocks DB.j, DB.k comprises a medical data set MDS.j, MDS.k, a nonce RN.j, RN.k, and a hash H(DB.i), H(DB.j) of the respective parent data block DB.i, DB.j.

The medical data sets MDS.j, MDS.k log the transfer of a medical data record MDR.j, MDR.k from a first entity to a second entity. So in the embodiment displayed in FIG. 21, the medical data set MDS.j, MDS.k comprises a hash H (MDR.j), H(MDR.k) of the medical data record MDR.j, MDR.k being transferred, an identifier E1ID.j, E1ID.k of the first entity involved in the transfer of the medical data record MDR.j, MDR.k, an identifier E2/D.j, E2/D.k of the second entity involved in the transfer of the medical data record MDR.j, MDR.k and a timestamp TS.j, TS.k corresponding to the time of the transfer of the medical data record MDR.j, MDR.k from the first entity to the second entity.

In this embodiment both the first entity and the second entity involved in the transfer of the medical data record MDR.j, MDR.k are persons, and the identifiers E1ID.j, E1ID.k of the first entity and the identifiers E2/D.j, E2/D.k of the second entity are the IDs of the persons in a central databank (e.g. a social insurance number). Alternatively, the identifiers E1ID.j, E1ID.k of the first entity and the identifiers E2/D.j, E2/D.k of the second entity can comprise personal data of the persons transferring the medical data record MDR.j, MDR.k, e.g. the name and/or the date of birth of the persons. Alternatively, identifiers E1ID.j, E1ID.k of the first entity and the identifiers E2/D.j, E2/D.k of the second entity involved in the transfer of the medical data record MDR.j, MDR.k can comprise a public key associated with the entities. Alternatively, the identifiers E1ID.j, E1ID.k of the first entity and the identifiers E2/D.j, E2/D.k of the second entity involved in the transfer of the medical data record MDR.j, MDR.k can be a signature signed with a private key associated with the first and/or second entity, in particular the signature can be created based on the medical data record MDR.j, MDR.k, the hash H(MDR.j), H(MDR.k) of the medical data record MDR.j, MDR.k, and/or on the timestamp TS.j, TS.k corresponding to the time of the access of the person or the general entity to the medical data record MDR.j, MDR.k.

In the embodiments displayed in FIG. 19, FIG. 20 and FIG. 3 the step of receiving REC-FDS a further medical data set FDS comprises the step of receiving REC-TR a transfer request directed at the medical data record MDR.1 with the interface BCU.IF of the block creation unit BCU, and the step of determining the further medical dataset FDS based on the transfer request with the calculation unit BCU.CU of the block creation unit BCU. In these embodiments the transfer request is issued by a receiving unit RU. In the displayed embodiments the transfer request comprises an identifier E2ID.1 of the second entity which receives the medical data record MDR.1 in the transfer of the medical data record MDR.1, and information about the medical data record MDR.1 to be transferred. In this embodiment, the information about the medical data record MDR.1 to be transferred is a hash H (MDR.1) of the medical data record MDR.1 to be accessed. Alternatively, the information about the medical data record MDR.1 to be transferred is a link to the medical data record MDR.1 to be transferred, in particular a unified resource locater (an acronym is "URL") pointing to the medical data record MDR.1 to be accessed. In particular, the URL of the medical data record MDR.1 to be transferred can comprise a hash H (MDR.1) of the medical data record MDR.1 to be transferred.

In these embodiments, the medical data record MDR.1 to be accessed is diagnostic data related to a patient. Diagnostic data can comprise one or more medical images of the patient (e.g. originating from X-ray fluoroscopy, angiography, computed tomography, magnetic resonance imaging, positron emission tomography, ultrasound imaging), diagnostic data can also comprise laboratory data (e.g. originating from laboratory diagnostic with respect to blood of a patient, urine of a patient, liquor of a patient or feces of a patient), diagnostic data can also comprise a medical diagnosis in a structured or un structured format. Alternatively, diagnostic data can also comprise a combination of several of the mentioned alternatives.

In the embodiments displayed in FIG. 19 and FIG. 20 the medical data record MDR.1 to be transferred is stored in a memory unit BCU.MU of the block creation unit BCU, in other words, the block creation unit BCU is related to the first entity or equivalent with the first entity. In this case the transfer request does not necessarily comprise the identifier E1ID.1 of the first entity involved in the transfer of the medical data record MDR.1, since identifier E1ID.1 of the first entity is known to the block creation unit BCU. In the embodiment displayed in FIG. 22 the medical data record MDR.1 to be transferred is stored in a memory unit of a sending unit SU, in other words, the sending unit SU is related to the first entity or equivalent with the first entity, whereas the block creation unit BCU is not related with the first entity and not identical with the first entity, so the block creation unit BCU is only a observer of the transfer of the medical data record MDR.1. In this case, the transfer request furthermore comprises the identifier E1ID.1 of the first entity involved in the transfer of the medical data record MDR.1.

In all embodiments displayed in FIG. 19, FIG. 20 and FIG. 21 in the step of determining DET-FDS the further medical dataset FDS based on the transfer re quest and based on the medical data record MDR.1 the further medical dataset FDS is determined such that the further medical dataset FDS comprises the hash H (MDR.1) of the medical data record MDR.1 being transferred, the identifier E1ID.1 of the first entity and the identifier E2ID.1 of the second entity involved in the transfer of the medical data record MDR.1 and the timestamp TS.1 corresponding to the time of the access to the medical data record MDR.1. In particular, the step of determining the further medical dataset FDS can comprise calculating the hash H (MDR.1) of the medical data record MDR.1 being transferred by applying a hash function on the medical data record MDR.1.

Alternatively, the further medical data set FDS can furthermore comprise personal data related to the patient (e.g. the name of the patient, the sex of the patient, the age of the patient, the size of the patient, the weight of the patient, or any combination thereof). The further medical data set FDS may also be defined with respect to a plurality of transfer requests to medical data records involving the same first entity and the same first entity, or involving different first entities, or involving different second entities; in this case the further medical data dataset FDS comprises the respective data for all of the transfer requests.

In particular the step of determining DET-FDS the further medical dataset FDS is executed such that the further medical dataset FDS complies with the format of the medical datasets MDS.j, MDS.k already contained in the data blocks DB.i, DB.j, DB.k already present in the first ledger LDG. In particular, also the medical datasets MDS.j, MDS.k comprise the hashes H(MDR.j), H(MDR.k) of the medical data records MDR.j, MDR.k having been accessed, the identifiers E1ID.j, E1ID.k of the first entities and the identifiers E2/D.j, E2/D.k of the second entities having been involved in the transfer of the respective medical data record MDR.j, MDR.k and the timestamp TS.j, TS.k corresponding to the time of the transfer of the medical data records MDR.j, MDR.k.

The methods displayed in FIG. 19, FIG. 20 and FIG. 21 furthermore comprises the step of providing PROV-FDB the further data block FDB with the interface BCU.IF of the block creation unit BCU. In this embodiment, the step of providing PROV-FDB the further data block FDB is executed after the step of inserting INS-FDB-1 the further data block into the first ledger LDG. Alter natively, the step of providing PROV-FDB the further data block FDB can also be executed before the step of inserting INS-FDB-1 the further data block FDB into the first ledger LDG.

Alternatively, the step of providing PROV-FDB the further data block FDB can also be executed parallel to the step of inserting INS-FDB-1 the further data block FDB into the first ledger LDG. In other words, the steps of providing PROV-FDB the further data block FDB is independent of the step of inserting INS-FDB-1 the further data block FDB into the first ledger LDG.

The method displayed in FIG. 19 furthermore comprises the step of providing PROV-MDR the medical data record MDR.1 by the interface BCU.IF of the block creation unit BCU and the step of receiving REC-MDR the medical data record MDR.1 by the receiving unit RU. The steps of providing PROV-MDR the medical data record MDR.1 and of receiving the medical data record MDR.1 can be part of a step of transmitting the medical data record MDR.1 from the block creation unit BCU to the receiving unit. As the step of providing PROV-FDB the further data block FDB the step of providing PROV-MDR the medical data record MDR.1 can be executed before, after or in parallel to the step of inserting INS-FDB-1 into the first ledger LDG. Furthermore, in this embodiment the step of providing PROV-MDR the medical data record MDR.1 is executed after the step of determining DET-FDB the further data block FDB. Alternatively, the step of providing PROV-MDR the medical data record MDR.1 can be executed before or in parallel to the step of determining DET-FDB the further data block FDB. The method displayed in FIG. 20 furthermore comprises the steps of determining DET-MMDR a modified medical data record with the calculation unit BCU.CU of the block creation unit BCU, the step of providing PROV-MMDR the modified medical data record with the interface BCU.IF of the block creation unit BCU and the step of receiving REC-MMDR the modified medical data record by the receiving unit RU.

In the displayed embodiment, the medical data record MDR.1 comprises a medical image, and the modified medical data record comprises a modified medical image. In particular, the modified medical data record can be identical to the medical data record MDR.1 with exception of the medical image. In this embodiment, the modified medical image is the medical image equipped with a watermark, wherein the watermark comprises the identifier E2ID.1 of the second entity involved in the transfer of the medical data record MDR.1. So the step of determining DET-MMDR comprises equipping the medical image with the watermark. In embodiment of the method displayed in FIG. 21 the block creation unit BCU is the observer of the transfer of the medical data record MDR.1 from the sending unit SU to the receiving unit. The embodiment of the method displayed in FIG. 21 furthermore comprise the step of forwarding FWD-TR the transfer request by the sending unit. In particular, a transfer request provided by the requesting unit is forwarded to the block creation unit. The method furthermore comprises the step of providing PROV-MDR the medical data record MDR.1 by the sending unit SU and the step of receiving REC-MDR the medical data record MDR.1 by the receiving unit. In the displayed embodiment, the step of providing PROV-MDR the medical data record MDR.1 by the sending unit SU is executed after the step or as a reaction to the step of providing PROV-FDB the further data block. In particular, the step of providing PROV-MDR the medical data record MDR.1 by the sending unit SU can also be executed after the step or as a reaction to the step inserting INS-FDB-1 the further data block FDB into the first ledger LDG. By this order of steps it is ensured that the actual transfer of the medical data record MDR.1 does only take place after the transfer has been recorded in the first ledger.

Figure 23:
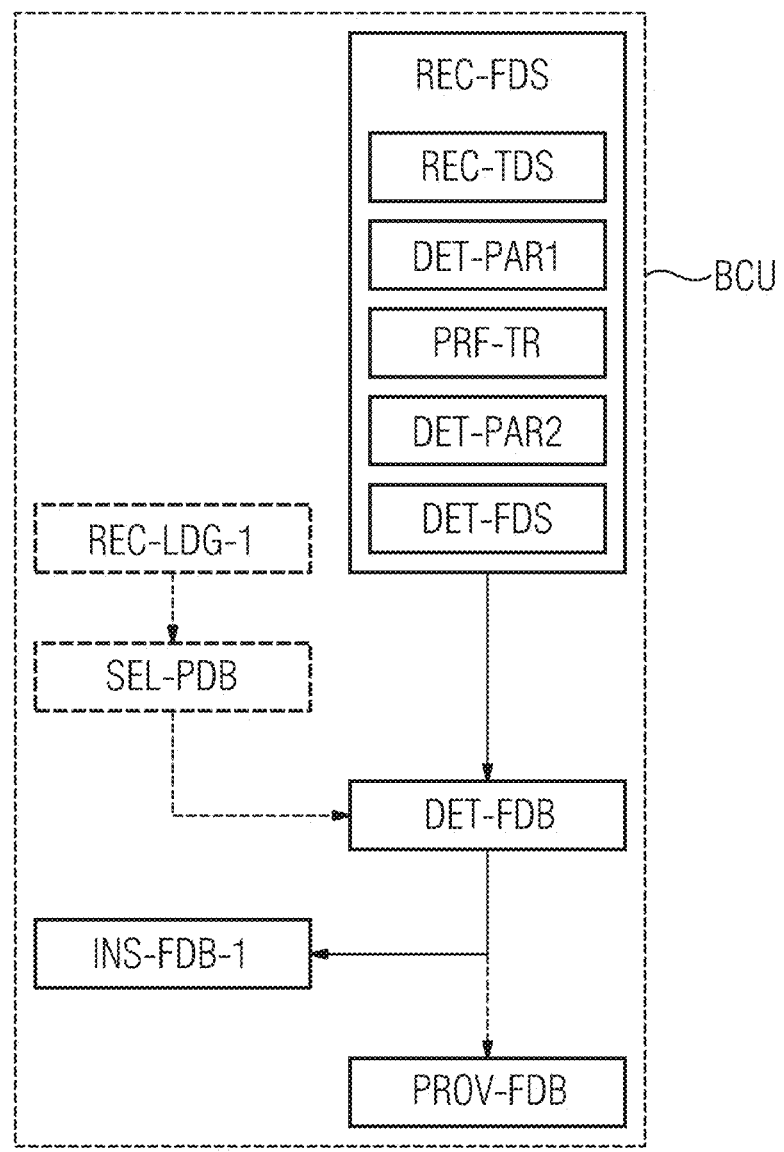
FIG. 23 displays an embodiment of the method for inserting a further data block into a first ledger, which relates to the admission process of a medical apparatus.

FIG. 23 displays a first embodiment of the method for inserting a further data block FDB into a first ledger LDG, wherein the further data block FDB comprises a further medical data set FDS, and wherein the further medical dataset FDS corresponds to the admission process of a medical apparatus MA.

Figure 24:
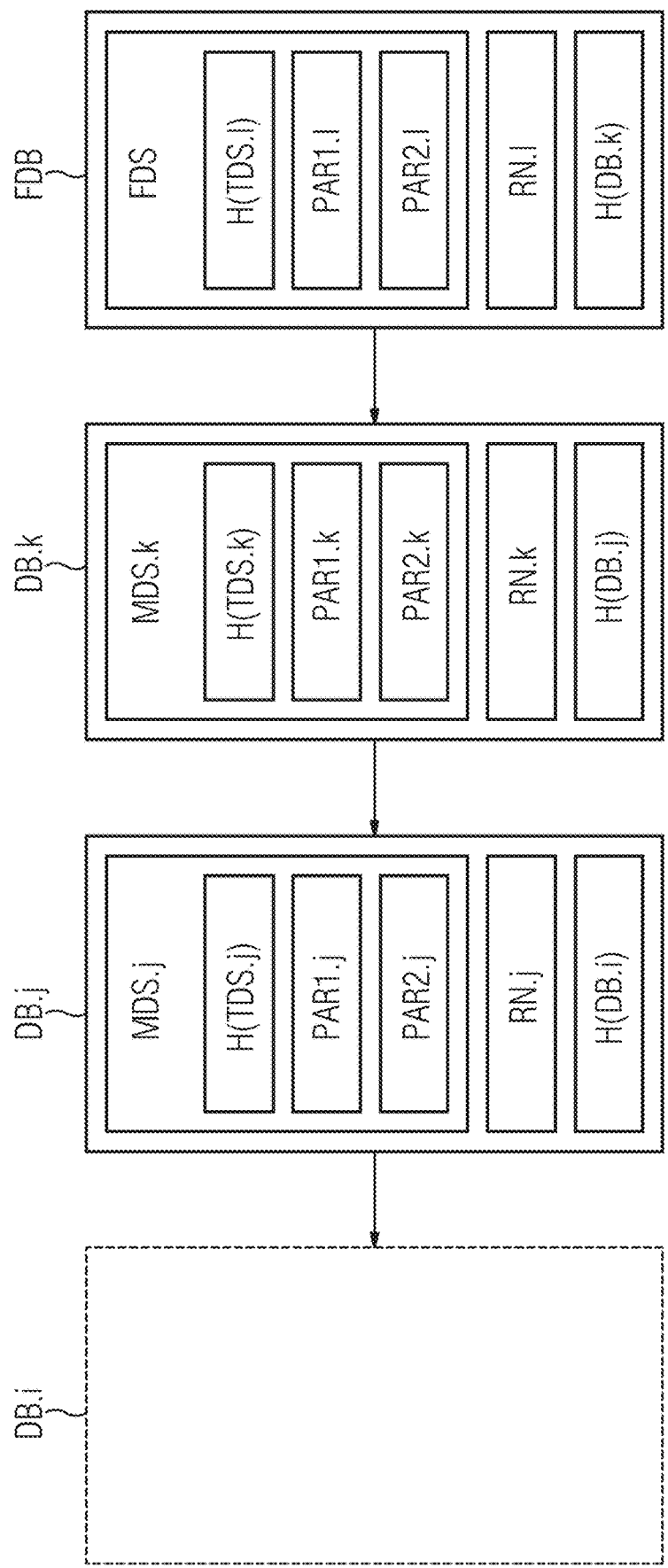
FIG. 24 displays an embodiment of a first ledger related to the admission process of a medical apparatus.

FIG. 24 displays the first ledger LDG after including the further data block FDB with the method displayed in FIG. 23. The displayed embodiment of the method for inserting a further data block FDB into a first ledger LDG comprises all steps of the method for inserting a further data block FDB into a first ledger LDG displayed in FIG. 1. Optionally these embodiments can also comprise the additional steps displayed in FIG. 3. All method steps contained in this embodiment may comprise all advantageous enhancement and alternatives described either in the description of FIG. 1 or in the description of FIG. 3.

In the embodiment displayed in FIG. 23 the medical apparatus MA comprises an artificial intelligence algorithm, in particular an artificial neural network and the further data set FDS contained in the further data block FDB relates to a training step of the artificial neural network. In this embodiment the artificial neural network gets as input a medical image, e.g. originating from a computed tomography apparatus or a magnetic resonance apparatus, and calculates as an output a label of the medical image, in this case an automatic segmentation of the medical image. Another example for such a label is a diagnostic information, e.g. a probability whether the displayed patient has a certain disease, or the probability for a certain structure in the medical image to be a malicious.

FIG. 24 displays data blocks DB.j, DB.k contained in the first ledger LDG used in the method displayed in FIG. 23. In particular, the further data block FDB has the same structure as the displayed data blocks DB.j, DB.k, and in particular, the further data block FDB can be identical with one of the displayed data blocks DB.j, DB.k.

Each of the displayed data blocks DB.j, DB.k comprises a medical data set MDS.j, MDS.k, a nonce RN.j, RN.k, and a hash H(DB.i), H(DB.j) of the respective parent data block DB.i, DB.j.

The medical data sets MDS.j, MDS.k log training steps of the artificial intelligence algorithms, wherein a training step comprises the training of the artificial intelligence algorithm with a training data set TDS.j, TDS.k. So in the embodiment displayed in FIG. 21, the medical data set MDS.j, MDS.k comprises a hash H(TDS.j), H (TDS.k) of the training data set TDS.j, TDS.k used for the training of the artificial intelligence algorithm. Furthermore the medical data sets MDS.j, MDS.k comprise a first parameter PAR1.k, PAR1.1 and a second parameter PAR2.$k$, PAR2.1, wherein the first parameter PAR1.k, PAR1.1 is a parameter of the artificial intelligence algorithm before being trained with the training data set TDS.j, TDS.k, and wherein the second parameter PAR2.$k$, PAR2.1 is a parameter of the artificial intelligence algorithm after being trained with the training data set TDS.j, TDS.k. In particular, before being trained with the training data set TDS.j, TDS.k means that no other training step is performed between extracting the first parameter PAR1.k, PAR1.1 and the training with the training data set TDS.j, TDS.k. In particular, after being trained with the training data set TDS.j, TDS.k means that no other training step is performed between training with the training data set TDS.j, TDS.k and extracting the second parameter PAR1.k, PAR1.1.

In this embodiment a training data set TDS.j, TDS.k comprises a medical training image and a segmentation of the medical training image, where the segmentation of the medical image can be created manually by a medical expert or automatically with another algorithm based on the medical training image. Furthermore, in this embodiment both the first parameter PAR1.k, PAR1.1 and the second parameter PAR2.$k$, PAR2.1 are vectors comprising all edge weights of the artificial neural network being trained.

In the embodiment displayed in FIG. 23 the step of receiving REC-FDS a further medical data set FDS comprises the step of receiving REC-TDS the training dataset TDS.1 with the interface BCU.IF, the step of determining DET-PAR1 a first parameter PAR1.1 of the artificial intelligence algorithm with the calculation unit BCU.CU, the step of performing PRF-TR a training step of the artificial intelligence algorithm based on the training dataset TDS.1 with the calculation unit BCU.CU, the step of determining DET-PAR2 a second parameter PAR2.1 of the artificial intelligence algorithm with the calculation unit BCU.CU, and the step of determining DET-FDS the further medical dataset FDS based on the training dataset TDS.1 and based on the first and the second parameter PAR1.1, PAR2.1 with the calculation unit BCU.CU.

In this embodiment the training dataset TDS.1 used in the step of performing PRF-TR a training step comprises a medical image and a segmentation of the medical image. The first parameter PAR1.1 comprises a vector of all edge weights of the artificial neural network directly before performing PRF-TR the training step, and the second parameter PAR2.1 comprises a vector of all edge weights of the artificial neural network directly after performing PRF-TR the training step.

The step of determining DET-PAR1 a first parameter PAR1.1 of the artificial intelligence algorithm and the step of determining DET-PAR2 a second parameter PAR1.1 of the artificial intelligence algorithm each include iterating through the ordered set of edges of the artificial intelligence algorithm, the ordering of the edges given by the artificial intelligence algorithm, and for each edge of the ordered set of edges of the artificial intelligence algorithm, including the respective weight into the vector of edge weights.

In this embodiment the step of performing PRF-TS the training step comprises using the medical training image contained in the training data set TDS.1 as an input of the artificial neural network and calculating an output of the artificial neural network being the result of the application of the artificial neural network on the input data. The step of performing PRF-TS the training step furthermore comprises comparing the output with the segmentation of the medical image contained in the training data set TDS.1, e.g. by calculating the sum of squared deviations between the output and the segmentation of the medical image contained in the training data set TDS.1. Furthermore, the step of performing PRF-TS the training step comprises an adjustment of parameters of the neural network based on the comparison, e.g. adjusting the edge weights of the neural network by using a backpropagation algorithm based on the sum of squared deviations.

Furthermore, in this embodiment the step of determining DET-FDS the further medical dataset FDS based on the training dataset TDS.1 and based on the first and the second parameter PAR1.1, PAR2.1 comprises calculating a hash H (TDS.1) of the training dataset TDS.1 and constructing the further medical dataset FDS comprising the hash H (TDS.1) of the training dataset TDS.1 and comprising the first and the second parameter PAR1.1, PAR2.1. Alternatively, the further medical dataset FDS can be determined such that the further medical dataset FDS directly comprises the training dataset TDS.1, or a link the training dataset TDS.1. Alternatively, the further medical dataset FDS can also not comprise the first parameter and the second parameter PAR1.1, PAR2.1, but a link to the first parameter and the second parameter PAR1.1, PAR2.1 and/or a hash of the first parameter and the second parameter PAR1.1, PAR2.1.

Figure 25:
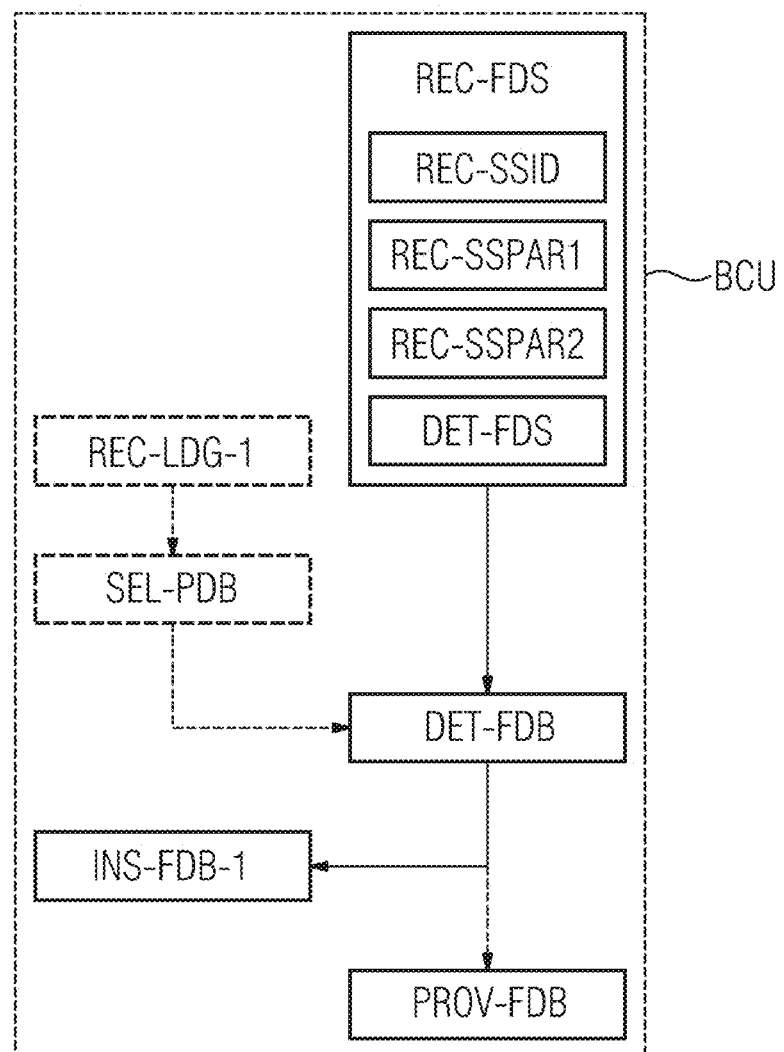
FIG. 25 displays a further embodiment of the method for inserting a further data block into a first ledger, which relates to the admission process of a medical apparatus.

FIG. 25 displays a second embodiment of the method for inserting a further data block FDB into a first ledger LDG, wherein the further data block FDB comprises a further medical data set FDS, and wherein the further medical dataset FDS corresponds to the admission process of a medical apparatus MA.

Figure 26:
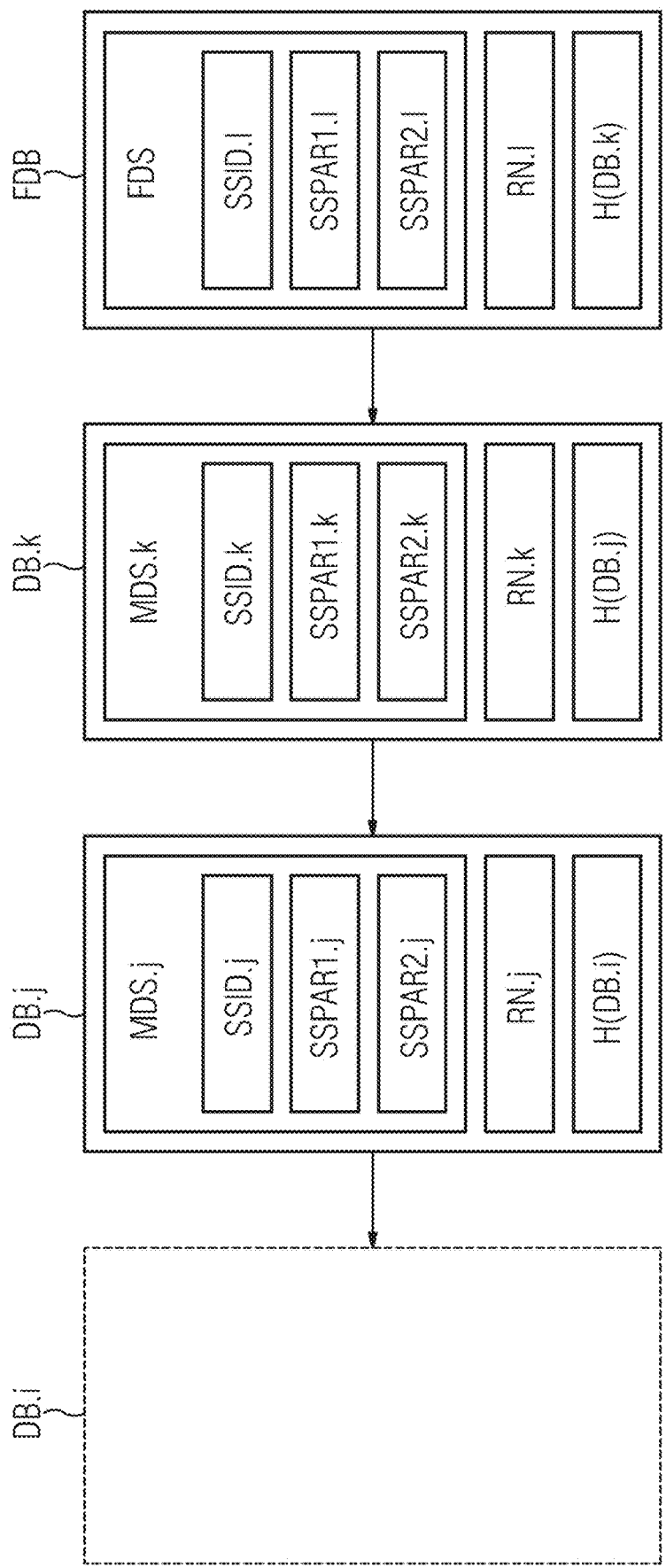
FIG. 26 displays a further embodiment of a first ledger related to the admission process of a medical apparatus.

FIG. 26 displays the first ledger LDG after including the further data block FDB with the method displayed in FIG. 25. The displayed embodiment of the method for inserting a further data block FDB into a first ledger LDG comprises all steps of the method for inserting a further data block FDB into a first ledger LDG displayed in FIG. 1. Optionally these embodiments can also comprise the additional steps displayed in FIG. 3. All method steps contained in this embodiment may comprise all advantageous enhancement and alternatives described either in the description of FIG. 1 or in the description of FIG. 3.

In the embodiment displayed in FIG. 25, the medical apparatus MA is a drug counteracting hypertension, and the medical data sets MDS.k, MDS.1 log the effect of the drug of certain patients, including patients suffering from hypertension and patients not suffering from hypertension. Alternatively, the described methods can also be used for studies concerning other diagnostic and therapeutic medical apparatus MAes.

FIG. 26 displays data blocks DB.j, DB.k contained in the first ledger LDG used in the method displayed in FIG. 24. In particular, the further data block FDB has the same structure as the displayed data blocks DB.j, DB.k, and in particular, the further data block FDB can be identical with one of the displayed data blocks DB.j, DB.k.

Each of the displayed data blocks DB.j, DB.k comprises a medical data set MDS.j, MDS.k, a nonce RN.j, RN.k, and a hash H(DB.i), H(DB.j) of the respective parent data block DB.i, DB.j.

The medical data sets MDS.j, MDS.k log in this embodiment log a single element of a medical study. So in the embodiment displayed in FIG. 25, the medical data set MDS.j, MDS.k comprises a an identifier SSID.j, SSID.k of a certain study subject (in this case, a patient suffering or not suffering from hypertension), a first parameter SSPAR1.j, SSPAR1.k of the study subject, and a second parameter SSPAR2.$k$, SSPAR2.$k$ of the study subject.

In this embodiment, the identifiers SSID.j, SSID.k of the study subject or patients relate to the fingerprint of the right index finger of the study subjects. In particular, they comprise a link to the stored fingerprint of the right index finger. By using the fingerprint of the right index finger a study subject can be uniquely identifier. Alternatively, of course it is possible to use other identifiers of persons, e.g. their social insurance number, an ID, or identifiers based on biometrical parameters, or their DNA.

Furthermore, in this embodiment the first parameter SSPAR1.j, SSPAR1.k and the second parameter SSPAR2.$j$, SSPAR2.$k$ corresponds to the blood pressure of the respective patient or study subject. In particular, the first parameter SSPAR1.j, SSPAR1.$k$ corresponds to the blood pressure of the patient before a treatment with the drug counteracting hypertension, and the second parameter SSPAR2.$j$, SSPAR2.$k$ corresponds to the blood pressure of the patient after the treatment with the drug counteracting hypertension. In this example treatment with the drug counteracting hypertension is a single application of the drug counteracting hypertension with a given dosage. Alternatively, treatment with the drug counteracting hypertension can be a multiple application of the drug counteracting hypertension with given dosages in given time intervals. The term "before a treatment" corresponds to a given time interval, e.g. 30 minutes, before the application of the drug, the term "after the treatment" corresponds to a given time interval, e.g. 3 hours, after the application of the drug.

In the embodiment displayed in FIG. 25, the step of receiving REC-FDS a further medical data set FDS comprises the step of receiving REC-SSID the identifier SSID.1 of the person being subject of the medical study with the interface BCU.IF, the step of receiving REC-SSPAR1 the first patient parameter SSPAR1.1 corresponding to the person before the medical study with the inter face BCU.IF, the step of receiving REC-SSPAR2 the second patient parameter SSPAR2.1 corresponding to the person after the medical study with the inter face, and the step of determining DET-FDS the further medical dataset FDS based on the identifier SSID.l of the person being subject of the medical study and based on the first patient parameter REC-SSPAR1 and the second patient parameter REC-SSPAR2 with the calculation unit.

In particular, the steps of receiving REC-SSID the identifier SSID.l, of receiving REC-SSPAR1 the first patient parameter SSPAR1.1 and of receiving REC-SSPAR2 the second patient parameter SSPAR2.1 can be independent of each other. This means that the order of the steps to be executed can be changed. In particular, it is possible that the step of receiving REC-SSPAR1 the first patient parameter SSPAR1.1 are executed in parallel.

Alternatively, it is also possible to receive other data related to the study with the interface BCU.IF, e.g. dosage information about the drug, variants of the drug being used, a parameter that describes whether the drug being used is the actual drug or a placebo drug, and to include this data and/or links to this data and/or hashes of this data into the further data block. Alternatively, it is also possible to include further patient parameter corresponding to the patient into the further data set FDS, e.g. corresponding to different measurement times, to document a broader picture of the reaction of the person to the medical study it is subject of.

Figure 27:
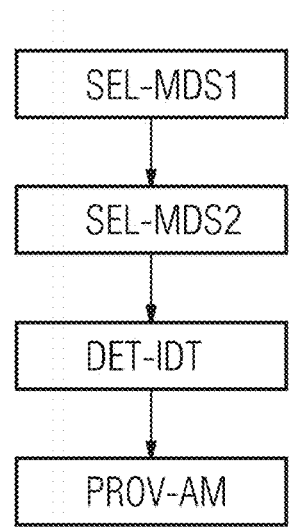
FIG. 27 displays a flowchart of a method for using a first ledger related to the admission process of a medical apparatus.

FIG. 27 displays a flowchart of an embodiment of the method for using a first ledger LDG, wherein a further data block FDB was included into the first ledger LDG according to the method displayed in FIG. 25. The displayed embodiment comprises the step of selecting SEL-MDS1 a first medical dataset contained in the first ledger LDG with a calculation unit, wherein the first medical dataset comprises an identifier SSID.j, SSID.k, SSID.l of a first person. The displayed embodiment furthermore comprises the step of selecting SEL-MDS2 a second medical dataset contained in the first ledger LDG with the calculation unit, wherein the second medical dataset is different from the first medical dataset, and wherein the second medical dataset comprises an identifier SSID.j, SSID.k, SSID.l of a second person. The displayed embodiment furthermore comprises the step of determining DET-IDT whether the first person and the second person are identical based on the identifier SSID.j, SSID.k, SSID.l of the first person and the identifier SSID.j, SSID.k, SSID.l of the second person with the calculation unit. The displayed embodiment furthermore comprises the step of, in the case of the first person and the second person being identical, providing PROV-AM an alert message with an inter face. In particular, the first ledger LDG used in the displayed embodiment is the first ledger LDG displayed in FIG. 4. The step of selecting SEL-MDS1 the first medical dataset MDS.j, MDS.k, FMDS comprises of the steps of selecting a first data block DB.j, DB.k, FDB of the first ledger LDG, wherein the first data block DB.i, DB.j, DB.k, FDB comprises the first medical dataset MDS.j, MDS.k, FMDS, and the step of extracting the first medical dataset MDS., MDS.k, FMDS from the first data block DB.i, DB.j, DB.k, FDB. The step of selecting SEL-MDS2 the second medical dataset MDS.j, MDS.k, FMDS comprises of the steps of selecting a second data block DB.j, DB.k, FDB of the first ledger LDG, wherein the second data block DB.i, DB.j, DB.k, FDB comprises the second medical dataset MDS.j, MDS.k, FMDS, and the step of extracting the second medical dataset MDS.j, MDS.k, FMDS from the second data block DB.i, DB.j, DB.k, FDB.

In the displayed embodiment, the identifier SSID.j, SSID.k, SSID.l of the first person corresponds to a fingerprint of the right index finger of the first person, and the identifier SSID.j, SSID.k, SSID.1 of the second person corresponds to a fingerprint of the right index finger of the second person. Alternatively other identifiers can be used, e.g. based on biometrical parameters of the first and the second person, based on the DNA sequence of the first and the second person, or based on an ID or a social insurance number of the first and the second person. Here the fingerprint is not stored within the medical dataset MDS.j, MDS.k, FMDS, but within the medical dataset MDS.j, MDS.k, FMDS a link is stored to the respective fingerprint stored outside. Optionally, also a hash value of the fingerprint can be stored.

In the step of determining DET-IDT whether the first person and the second person are identical based on the identifier SSID.j, SSID.k, SSID.1 of the first person and the identifier SSID.j, SSID.k, SSID.1 of the second person, in this embodiment the respective fingerprints of the first person and the second person are compared. In particular, a first fingerprint is considered to be equivalent with a second fingerprint if a certain number of landmarks of the first fingerprint can also be found in the second fingerprint, and the first person is determined as being identical with the second person, if the respective fingerprints are equivalent. If alternatively the identifier SSID.j, SSID.k, SSID.l is based on a DNA sequence, the first person is determined as being identical with the second person if the respective DNA sequences can be matched up to a certain level of errors. If alternatively the identifier SSID.j, SSID.k, SSID.l is based on a biometrical parameter, the first person is determined as being identical with the second person of the relative deviation between the respective biometrical parameters is below a given threshold.

Figure 28:
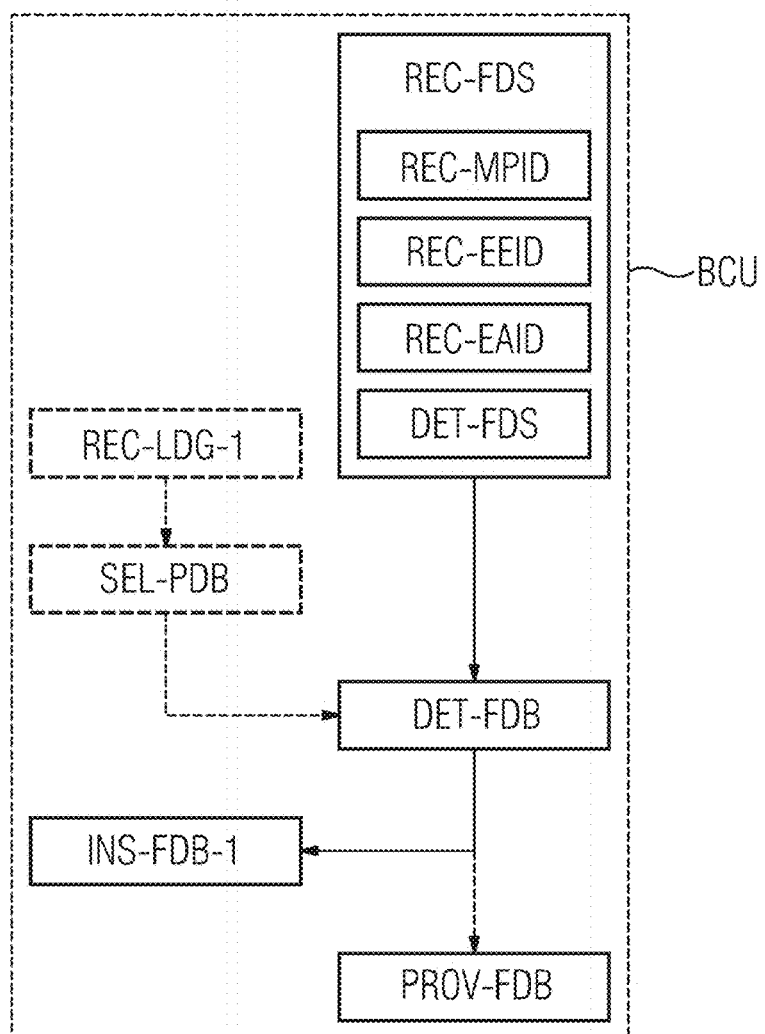
FIG. 28 displays an embodiment of the method for inserting a further data block into a first ledger, which can be used for documenting an educational action of a medical professional.
Figure 29:
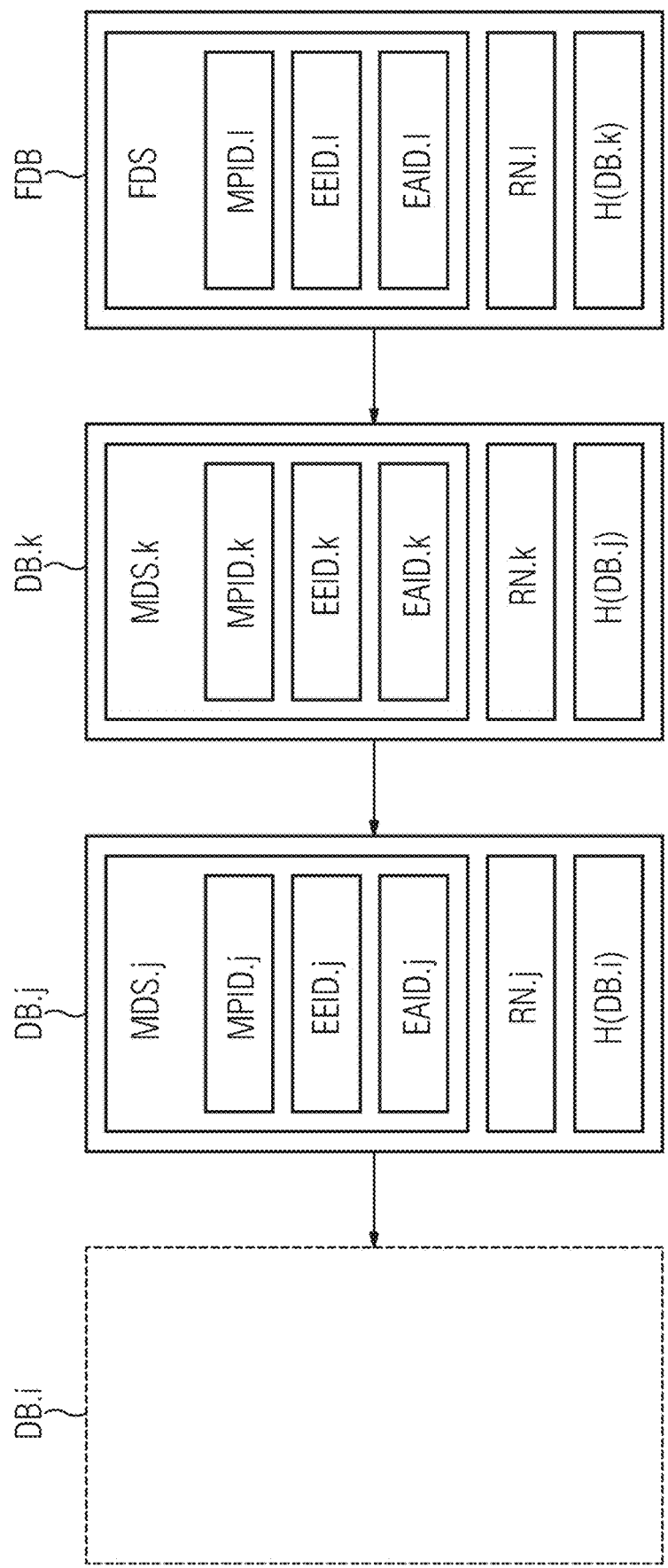
FIG. 29 displays an embodiment of a first ledger used for documenting an educational action of a medical professional.

FIG. 28 displays a first embodiment of the method for inserting a further data block FDB into a first ledger LDG, wherein the further data block FDB comprises a further medical data set FDS, wherein the further medical dataset FDSS relates to an educational action of a medical professional, and wherein the further medical dataset comprises an identifier MPID.l of the medical professional and an identifier EAID.l of the educational action. FIG. 29 displays a part of the first ledger LDG after including the further data block FDB with the method displayed in FIG. 28. The displayed embodiment of the method for inserting a further data block FDB into a first ledger LDG comprises all steps of the method for inserting a further data block FDB into a first ledger LDG displayed in FIG. 1. Optionally these embodiments can also comprise the additional steps displayed in FIG. 3. All method steps contained in this embodiment may comprise all advantageous enhancement and alternatives described either in the description of FIG. 1 or in the description of FIG. 3.

In the embodiment displayed in FIG. 28 the medical professional is a physician trained by an education entity, wherein the education entity is for ex ample an experienced medical physician. In particular, the medical professional performs medical actions like interventions, diagnostic procedures or therapeutic methods under the supervision of the experienced medical physician. In particular, the experienced medical physician has to confirm that the physician being trained by him has successfully executed the educational action.

FIG. 29 displays data blocks DB.j, DB.k contained in the first ledger LDG used in the method displayed in FIG. 28. In particular, the further data block FDB has the same structure as the displayed data blocks DB.j, DB.k, and in particular, the further data block FDB can be identical with one of the displayed data blocks DB.j, DB.k.

Each of the displayed data blocks DB.j, DB.k comprises a medical data set MDS.j, MDS.k, a nonce RN.j, RN.k, and a hash H(DB.i), H(DB.j) of the respective parent data block DB.i, DB.j.

The medical data sets MDS.j, MDS.k log educational actions of medical professionals, wherein there is an identifier EAID.j, EAID.k for each educational action. The identifier EAID.j, EAID.k can be the name of the educational action (for example the label of the intervention executed under the supervision of the experienced physician), or an ID related to the educational action from a catalogue of educational actions. In the displayed embodiment the medical data sets MDS.j, MDS.k comprise an identifier MPID.j, MPID.k of the medical professional, an identifier EEID.j, EEID.k of the educational entity and the identifier EAID.j, EAID.k of the educational action. Alternatively, the medical data sets MDS.j, MDS.k can also comprise a hash value based on one of these identifiers or on any combination of these identifiers.

In particular, in the displayed embodiment the identifier MPID.j, MPID.k of the medical professional is a combination of the name and the date of birth of the medical professional, and the identifier EEID.j, EEID.k of the educational entity comprises a signature signing the identifier MPID.j, MPID.k of the medical professional and the identifier EAID.j, EAID.k of the educational action. Alternatively, the identifier MPID.j, MPID.k of the medical professional can be an ID of the medical professional in a regional, national or international register of medical professionals. In particular, the identifier EEID.j, EEID.k of the educational entity furthermore comprises an ID of the educational entity in a regional, national or international register of educational entities. If the educational entity is an experienced physician, the regional, national or international register of medical professionals can be identical with the regional, national or international register of educational entities.

In the embodiment displayed in FIG. 28 the step of receiving REC-FDS a further medical data set FDS comprises the step of receiving REC-MPID the identifier MPID.l of the medical professional with the interface BCU.IF, the step of receiving the identifier EEID.l of the educational entity with the inter face BCU.IF, the step of receiving the identifier EAID.l of the educational action and the step of determining DET-FDS the further dataset based on the identifier MPID.l of the medical professional, based on the identifier EEID.l of the educational entity and based on the identifier EAID.l of the educational action with the with the calculation unit BCU.CU.

In this embodiment the identifier MPID.l of the medical professional has the same properties as the identifier MPID.j, MPID.k of the medical professionals already contained in the first ledger LDG. Furthermore, in this embodiment the identifier EEID.l of the educational entity has the same properties as the identifiers EEID.j, EEID.k of the educational entities already contained in the first ledger LDG. Furthermore, in this embodiment the identifier EAID.l of the educational action has the same properties as the identifiers EAID.j, EAID.k of the educational actions already contained in the first ledger LDG. Alternatively to the step of receiving the identifier EEID.l of the educational entity the method for inserting a further data block FDB into the first ledger can comprise the step of determining the identifier EEID.l of the educational entity based on the identifier MPID.l of the medical professional and on the identifier EAID.l of the educational action by the calculation unit BCU.CU. In particular, this step of determining can comprise calculating a signature by signing the identifier MPID.l of the medical professional and the identifier EAID.l with a private key of the educational entity.

FIG. 29 displays a second embodiment of the method for inserting a further data block FDB into a first ledger LDG, wherein the further data block FDB comprises a further medical data set FDS, wherein the further medical dataset FDSS relates to an educational action of a medical professional, and wherein the further medical dataset comprises an identifier MPID.l of the medical professional and an identifier EAID.l of the educational action. FIG. 31 displays a part of the first ledger LDG after including the further data block FDB with the method displayed in FIG. 30. The displayed embodiment of the method for inserting a further data block FDB into a first ledger LDG comprises all steps of the method for inserting a further data block FDB into a first ledger LDG displayed in FIG. 1. Optionally these embodiments can also comprise the additional steps displayed in FIG. 3. All method steps contained in this embodiment may comprise all advantageous enhancement and alternatives described either in the description of FIG. 1 or in the description of FIG. 3.

In the embodiment displayed in FIG. 28 the medical professional is a physician being trained with synthetically generated medical data records, and wherein the success of the training is assessed based on a comparison of a synthetically generated first medical information, and a second medical information generated by the physician by performing diagnosis of a synthetically generated medical data record. In particular, the synthetically generated medical data record is a synthetically generated imaging data set, in particular a synthetically generated computed tomography imaging data set similar to a computed tomography imaging data set of a lung of a patient.

Figure 30:
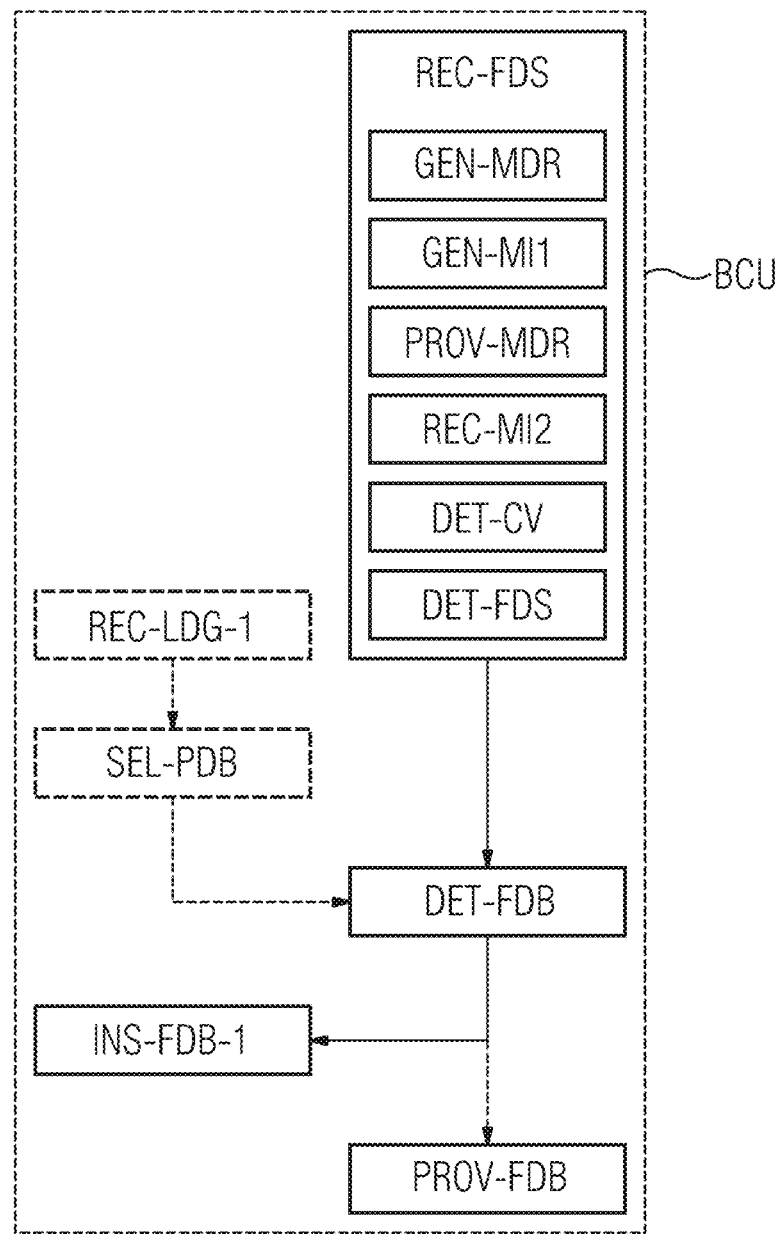
FIG. 30 displays a further embodiment of the method for inserting a further data block into a first ledger, which can be used for documenting an educational action of a medical professional.
Figure 31:
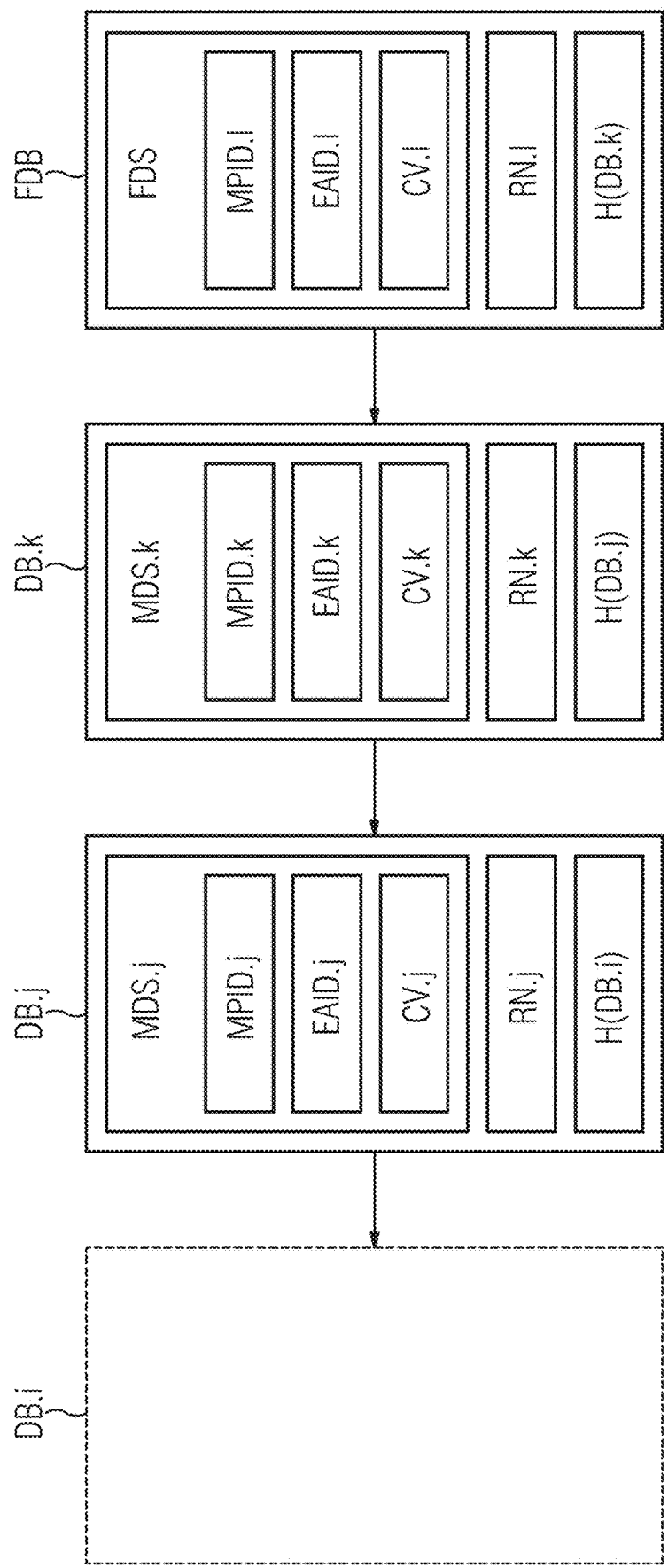
FIG. 31 displays a further embodiment of a first ledger used for documenting an educational action of a medical professional, FIG. 32 displays a flowchart of an embodiment of a method for using a first ledger for verifying the experience of a medical professional.

FIG. 31 displays data blocks DB.j, DB.k contained in the first ledger LDG used in the method displayed in FIG. 30. In particular, the further data block FDB has the same structure as the displayed data blocks DB.j, DB.k, and in particular, the further data block FDB can be identical with one of the displayed data blocks DB.j, DB.k.

Each of the displayed data blocks DB.j, DB.k comprises a medical data set MDS.j, MDS.k, a nonce RN.j, RN.k, and a hash H(DB.i), H(DB.j) of the respective parent data block DB.i, DB.j.

The medical data sets MDS.j, MDS.k log educational actions of medical professionals, wherein there is an identifier EAID.j, EAID.k for each educational action. In this embodiment, the identifier EAID.j, EAID.k of an educational action comprises data related to a synthetically generated imaging dataset.

In particular, the identifier EAID.j, EAID.k can comprise the type of the synthetically generated imaging dataset (e.g. whether it is a computed tomography imaging dataset, a magnetic resonance imaging dataset, or a fluoroscopy imaging dataset) and a description of the region of interest depicted by the synthetically generated imaging dataset (e.g. "lung", "chest", "abdomen", "head"). Advantageously the identifier can also comprise the first medical information, e.g. whether the synthetically generated imaging dataset comprises a certain features (e.g. a tumor). Alternatively the identifier EAID.j, EAID.k of the educational action can also comprise the synthetically generated imaging dataset itself, a link to the synthetically generated imaging dataset, and/or a hash of the synthetically generated imaging dataset.

In the displayed embodiment the medical data sets MDS.j, MDS.k furthermore comprise identifiers MPID.j, MPID.k of the medical professionals. In the displayed embodiment the medical data sets MDS.j, MDS.k furthermore comprise comparison values CV.j, CV.k, wherein the comparison values are based on a comparison of the first medical first medical information and the second medical information.

In particular, in the displayed embodiment the identifier MPID.j, MPID.k of the medical professional is a combination of the name and the date of birth of the medical professional. Alternatively, the identifier MPID.j, MPID.k of the medical professional can be an ID of the medical professional in a regional, national or international register of medical professionals.

In the displayed embodiment, the first medical information and the second medical information are segmentations of objects within the synthetically generated imaging dataset, in particular segmentations of one or more tumors depicted in the synthetically generated imaging dataset. In particular, the first medical information is generated together with the synthetically generated imaging dataset, and is the ground truth segmentation, and the second medical information is a segmentation generated by the medical professional. In particular, in this embodiment the comparison value is a distance measure of the first medical information and the second medical information, in particular the ratio of pixels or voxels in the synthetically generated imaging dataset that are assigned to different segments in the first medical information and the second medical information.

In the embodiment displayed in FIG. 30 the step of receiving REC-FDS the further medical dataset FDS comprises the step of generating GEN-MDR a medical data record with the calculation unit BCU.CU, the step of generating GEN-MI1 a first medical information with the calculation unit BCU.CU, in particular generating GEN-MI1 the first medical information based on the medical data record. Alternatively, the step of generating GEN-MI1 the first medical information can be executed before the step of generating GEN-MDR a medical data record, in particular, generating GEN-MDR the medical data record can be based on the first medical information. The step of receiving REC-FDS the further medical dataset FDS furthermore comprises the step of providing PROV-MDR the medical data record with the interface BCU.IF to the medical professional, the step of receiving REC-MI2 the second medical information with the interface BCU.IF from the medical professional, the step of determining DET-CV the comparison value CV.l based on the first medical information and based on the second medical information, and the step of determining DET-FDS the further data set based on the comparison value CV.l.

In the displayed embodiment the medical data record is a synthetically generated medical imaging dataset corresponding to a certain part of the human body. For example, the medical data record can be a synthetically generated computer tomography dataset corresponding to a lung of the human body.

In this embodiment the medical data record is generated by a first generative adversarial network or by a second generative adversarial network, wherein the first generative adversarial network was trained with computed tomography datasets of the certain part of the human body without a tumor, and wherein the second generative adversarial network was trained with computed tomography datasets of the certain part of the human body comprising a tumor. In other words, the first generative adversarial network generates medical data records being synthetically generated imaging datasets without tumors, and the second generative adversarial network generates medical data records with tumors. Alternatively it is only possible to use the second generative adversarial network if the focus of the training is only on segmentation, and not on recognizing whether there are tumors in a synthetically generated imaging dataset. The first medical information is determined with another neural network, taking as input imaging datasets and generating as output segmentations of the imaging datasets.

The another neural network can be trained on real imaging datasets with associated segmentations, or on synthetically generated imaging datasets with associated segmentations. The segmentations for the training of the another neural network can be determined by experienced medical professionals. Alternatively it is also possible to use a second generative adversarial network which takes as an input a given segmentation as first medical information, and determines a synthetically generated imaging dataset associated with the given segmentation.

In the displayed embodiment the step of receiving REC-MI2 the second medical information comprises receiving of an identifier MPID.l of the medical professional that created the second medical information. Alternatively, there can be a separate step of receiving REC-MPID the identifier MPID.l of the medical professional that created the second medical information.

In the step of determining DET-CV the comparison value CV.l a distance measure between the first medical information and the second medical information is calculated, wherein both the first medical information and the second medical information are segmentations of the synthetically generated medical imaging dataset. In this embodiment, a segmentation assigns to each pixel or voxel of the synthetically generated medical imaging dataset the value 0 or 1, so a segmentation itself is an image with the same dimension as the synthetically generated medical imaging dataset. In particular, a pixel or a voxel of the synthetically generated medical imaging dataset will be assigned with the value 1, if corresponds to the image of a tumor in the synthetically generated medical imaging dataset, otherwise it will be assigned with the value 0.

The comparison value being used in this embodiment is the ratio of pixels or voxels in the synthetically generated imaging dataset that are assigned to different segments in the first medical information and the second medical information: Image available on "Original document".

Here, $MI<(½)>±$ is the i-th value of the first or second medical information (in other words, $MI<(½)>±=0$ or 1), and N is the total number of voxels in the synthetically generated imaging dataset. Alternatively, other distance measure can be used, e.g. the mean squared deviation or a Hamming distance.

Within the step of determining DET-FDS the further dataset FDS, in this embodiment the identifier EAID.l of the educational action is determined. In particular, in this embodiment the synthetically generated imaging dataset, the first medical information and the second medical information can be stored within a Webserver, and the identifier EAID.l of the educational action can comprise a link to the synthetically generated imaging dataset, a link to the first medical information and/or a link to the second medical information. Furthermore, to ensure the integrity of the data stored outside of the first ledger LDG, the identifier EAID.l of the educational action can additionally comprise a hash of the synthetically generated imaging dataset, a hash of the first medical information and/or a hash of the second medical information.

Figure 32:
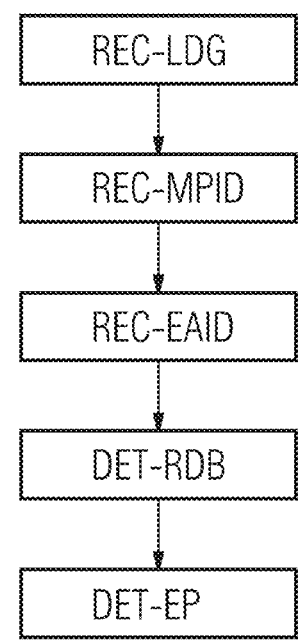

FIG. 32 displays a flowchart of an embodiment of a method for using a first ledger LDG after inserting a further data block FDB for verifying the experience of a medical professional. The first steps of the displayed embodiments are the step of receiving REC-LDG the first ledger LDG with an interface CN1.IF, CN2.IF, the step of receiving REC-MPID an identifier MPID.j, MPID.k, MPID.l of the medical professional with the interface CN1.IF, CN2.IF, and the step of receiving REC-EAID an identifier of an educational action EAID.j, EAID.k, EAID.l with the interface CN1.IF, CN2.IF. These three steps can be executed in an arbitrary order, alternatively two of these three steps or all of these three steps can be executed in parallel.

The first ledger LDG being received within the step of receiving REC-LDG the first ledger is partially displayed in FIG. 4, in particular, the first ledger LDG comprises data blocks DB.i, DB.j, DB.k and a further data block FDB, each of the data blocks DB.i, DB.j, DB.k and the further data block FDB comprising a medical dataset MDS.j, MDS.k or a further medical data set FDS.

Each of the medical datasets MDS.j, MDS.k and the further medical data set FDS comprises an identifier MPID.j, MPID.k, MPID.l of a medical professional, an identifier EAID.j, EAID.k, EAID.l of an educational action, and a comparison value CV.j, CV.k, CV.l.

In this embodiment, an educational action is the diagnosis of a synthetically generated imaging dataset by a medical professional, wherein a comparison value is determined based on a first medical information being the actual segmentation of the synthetically generated imaging dataset and a second medical information being a segmentation of the synthetically generated imaging dataset determined by the medical professional. Alternatively, the method can also be used for determining whether a given medical professional has executed a stipulated number of a medical intervention, e.g. a number of knee arthroplasties. In a further alternative, the method can also be used for determining whether a given medical professional has gathered a stipulated amount of training credits (e.g. CME credits) in a given timespan.

Alternatively, the first ledger LDG can also comprise data blocks without medical data sets of the described structure. In this case the described method is only applied to the subset of data blocks of the first ledger comprising the medical datasets MDS.j, MDS.k and the further medical data set FDS.

The next step of the described embodiment is determining DET-RDB the relevant data blocks of the first ledger LDG with a calculation unit CN1.CU, CN2.CU, wherein a relevant data block is a data block DB.i, DB.j, DB.k, FDB of the first ledger LDB comprising a relevant medical dataset, and wherein a relevant medical dataset MDS.j, MDS.k, FDS is a medical dataset comprising the identifier of the medical professional and the identifier of the educational action. Alternatively, there can be additional requirements for a data block DB.i, DB.j, DB.k, FDB being a relevant data block, e.g. that a relevant data block was created in a given timespan, or that a relevant data block comprises a comparison value CV.j, CV.k, CV.l with a certain property (e.g. being larger than a given threshold).

The next step of the described embodiment is determining DET-EP an education parameter based on the relevant data blocks with the calculation unit CN1.CU, CN2.CU. In the described embodiment, the MDS.j, MDS.k, FDS comprise a comparison value CV.j, CV.k, CV.l being the ratio of pixels or voxels in the synthetically generated imaging dataset that are assigned to different segments in the first medical information and the second medical information. The education parameter is then the number of relevant data blocks with a comparison value CV.j, CV.k, CV.l below a given threshold (e.g. here 0.1) and the total number of relevant data blocks. Alternatively, the education parameter can also be the total number of relevant data blocks, e.g. if determining whether a given medical professional has executed a stipulated number of a medical intervention. Alternatively, the education parameter can also be a sum of credits contained in the relevant data blocks.

Wherever not already described explicitly, individual embodiments, or their individual embodiments and features, described in relation to the drawings can be combined or exchanged with one another without limiting or widening the scope of the described invention, whenever such a combination or exchange is meaningful and in the sense of this invention. Advantageous which are described with respect to one embodiment of the present invention or with respect to one figure are, wherever applicable, also advantages of other embodiments of the present invention.

The invention claimed is:

1. A method for inserting a further data block into a first ledger, the first ledger including a plurality of data blocks, the method comprising:
   receiving a medical dataset via an interface, the medical dataset being a log of an access of an entity to a medical apparatus and the medical dataset including an identifier of the medical apparatus and an identifier of the entity accessing the medical apparatus, the access of the entity to the medical apparatus including an interaction of the entity with the medical apparatus;
   selecting a parent data block of the first ledger, the parent data block being selected based on a maximal sum of distances from the parent data block to each of a first origin data block and a second origin data block of the first ledger;
   determining the further data block via a processor, the further data block including the medical dataset and link information, and the link information including a hash of the parent data block of the first ledger;
   inserting the further data block into the first ledger via the processor; and
   granting remote access of the medical apparatus to the entity via the processor after the inserting the further data block into the first ledger, the interaction of the entity with the medical apparatus being a remote connection between the entity and the medical apparatus.

2. The method of claim 1, wherein the identifier of the medical apparatus is based on at least one of a model number of the medical apparatus and a serial number of the medical apparatus.

3. The method of claim 2, wherein the identifier of the entity includes a signature signed with a private key assigned to the entity.

4. The method of claim 3, wherein the signature is based on the identifier of the medical apparatus.

5. The method of claim 1, wherein the identifier of the entity includes a signature signed with a private key assigned to the entity.

6. The method of claim 5, wherein the signature is based on the identifier of the medical apparatus.

7. The method of claim 1, further comprising:
   sending a notification message to an owner of the medical apparatus via the interface,
   wherein the notification message is based on the identifier of the medical apparatus and the identifier of the entity accessing the medical apparatus.

8. The method of claim 1, further comprising:
   transferring cryptocurrency from a first account to a second account via the processor, wherein the first account is an account of an owner of the medical apparatus and wherein the second account is an account of the entity accessing the medical apparatus.

9. The method of claim 1, wherein the medical dataset includes a time of access of the entity to the medical apparatus, wherein at least one of
   the time of access corresponds to a time establishing a remote access to the medical apparatus by the entity, and
   the medical dataset includes a time of egress of the entity from the medical apparatus, wherein the time of egress corresponds to a time terminating the remote access to the medical apparatus.

10. The method of claim 1, wherein each of the plurality of data blocks of the first ledger includes a medical dataset and a link information, the link information including a hash of at least one of the plurality of data blocks of the first ledger.

11. The method of claim 1, wherein the determining of the further data block includes execution of a consensus algorithm.

12. The method of claim 1, wherein the first ledger is at least one of a blockchain, a blocktree and a tangle.

13. The method of claim 1, further comprising:
   receiving a second ledger via a second processor;
   transmitting the further data block, via the interface, to the second processor; and
   verifying the link information based on the second ledger, via the second processor, and, upon the verifying indicating a positive verification, inserting the further data block into the second ledger via the second processor.

14. The method of claim 1, further comprising:
   checking an authentication of the entity accessing the medical apparatus,
   wherein the granting remote access to the entity accessing the medical apparatus occurs in response to the checking positively authenticating the entity.

15. The method of claim 14, further comprising:
   denying remote access to the entity accessing the medical apparatus in response to the checking not authenticating the entity.

16. The method of claim 1, wherein the first origin data block and the second origin data block do not include link information.

17. A system for inserting a further data block into a first ledger, wherein the first ledger includes a plurality of data blocks, the system comprising:
   an interface, configured to receive a medical dataset, the medical dataset being a log of an access of an entity to a medical apparatus and the medical dataset including an identifier of the medical apparatus and an identifier of the entity accessing the medical apparatus, the access of the entity to the medical apparatus including interaction of the entity with the medical apparatus; and
   a processor, configured to cause the system to
      select a parent data block of the first ledger, the parent data block being selected based on a maximal sum of distances from the parent data block to each of a first origin data block and a second origin data block of the first ledger,
      determine the further data block, the further data block including the medical dataset and link information, and the link information including a hash of at least one of the plurality of data blocks of the first ledger,
      insert the further data block into the first ledger, and
      grant remote access to the entity accessing the medical apparatus after inserting the further data block into the first ledger, the interaction of the entity with the medical apparatus being a remote connection between the entity and the medical apparatus.

18. The system of claim 17, wherein the identifier of the medical apparatus is based on at least one of a model number of the medical apparatus and a serial number of the medical apparatus.

19. The system of claim 17, wherein the processor is further configured to cause the system to:
   check an authentication of the entity accessing the medical apparatus,
   wherein the granting remote access to the entity accessing the medical apparatus occurs in response to the checking positively authenticating the entity.

20. The system of claim 19, wherein the processor is further configured to cause the system to:
 deny remote access to the entity accessing the medical apparatus in response to the checking not authenticating the entity.

\* \* \* \* \*